(12) United States Patent
Whitelock et al.

(10) Patent No.: US 10,385,143 B2
(45) Date of Patent: Aug. 20, 2019

(54) METHOD FOR PRODUCTION OF HEPARIN AND HEPARAN SULFATE

(71) Applicant: NEWSOUTH INNOVATIONS PTY LIMITED, Sydney (AU)

(72) Inventors: John M Whitelock, New South Wales (AU); Megan S Lord, West Pennant Hills (AU)

( * ) Notice: Subject to any disclaimer, the term of this patent is extended or adjusted under 35 U.S.C. 154(b) by 0 days.

(21) Appl. No.: 15/322,411

(22) PCT Filed: Apr. 28, 2016

(86) PCT No.: PCT/AU2016/050301
§ 371 (c)(1),
(2) Date: Dec. 27, 2016

(87) PCT Pub. No.: WO2016/172766
PCT Pub. Date: Nov. 3, 2016

(65) Prior Publication Data
US 2018/0044442 A1    Feb. 15, 2018

(30) Foreign Application Priority Data

Apr. 30, 2015 (AU) ............................... 2015901556
Oct. 21, 2015 (AU) ............................... 2015904325

(51) Int. Cl.
| C08B 37/00 | (2006.01) |
| A61K 31/727 | (2006.01) |
| C07K 14/47 | (2006.01) |
| C12P 21/00 | (2006.01) |
| C12P 19/26 | (2006.01) |
| A61K 38/00 | (2006.01) |

(52) U.S. Cl.
CPC ........ *C08B 37/0075* (2013.01); *A61K 31/727* (2013.01); *C07K 14/4725* (2013.01); *C08B 37/0003* (2013.01); *C12P 19/26* (2013.01); *C12P 21/005* (2013.01); *A61K 38/00* (2013.01); *C07K 2319/02* (2013.01); *C07K 2319/20* (2013.01); *C12N 2510/00* (2013.01); *C12N 2510/02* (2013.01)

(58) Field of Classification Search
None
See application file for complete search history.

(56) References Cited

U.S. PATENT DOCUMENTS 5,486,599 A    1/1996 Saunders et al.

OTHER PUBLICATIONS

Alliel et al., "Complete amino acid sequence of a human platelet proteoglycan" 236(1) FEBS Letters 123-126 (1988).*
Stevens et al., "Isolation and Characterization of a cDNA That Encodes the Peptide Core of the Secretory Granule Proteoglycan of Human Promyelocytic Leukemia HL-60 Cells" 263(15) The Journal of Biological Chemistry 7287-7291 (1988).*
Parthasarathy et al., "Influence of glucose on production and N-sulfation of heparan sulfate in cultured adipocyte cells" 213 Molecular and Cellular Biochemistry 1-9 (2000).*
Kolset et al., "Serglycin—Structure and biology" 65 Cellular and Molecular Life Sciences 1073-1085 (2008).*
Lord, M.S., et al. "Bioengineered heparin: is there a future for this form of the successful therapeutic?" Bioengineered, 2014, vol. 5, pp. 222-226.
Whitelock, J., et al. "Recombinant heparan sulfate for use in tissue engineering applications" Journal of Chemical Technology and Biotechnology, 2008, vol. 83, pp. 496-504.
Gasimli, L., et al. "Bioengineering murine mastocytoma cells to produce anticoagulant heparin" Glycobiology, 2014, vol. 24, pp. 272-280.
Montgomery, R.I., et al. "Stable heparin-producing cell lines derived from the Furth murine mastocytoma" Proceedings of the National Academy of Science U S A, 1992, vol. 89, pp. 11327-11331.
Baik, J.Y., et al. "Toward a bioengineered heparin: challenges and strategies for metabolic engineering of mammalian cells" Bioengineered, 2012, vol. 3, pp. 227-231.
Datta, P., et al. "Bioengineered Chinese hamster ovary cells with Golgi-targeted 3-O-sulfotransferase-1 biosynthesize heparan sulfate with an antithrombin-binding site" Journal of Biological Chemistry, 2013, vol. 288, pp. 37308-37318.
Mackenzie, Susan "International Search Report and Written Opinion—Application No. PCT/AU2016/050301" Australian patent office as ISA; Jul. 25, 2016; pp. 1-10.
Elin Ronnberg, et al., "Mast Cell Proteoglycans," Journal of Histochemistry & Cytochemistry, vol. 60; pp. 950-962; 2012.
Annette Biederbick, et al., "Serglycin proteoglycan is sorted into zymogen granules of rat pancreatic acinar cells," European Journal of Cell Biology; vol. 82; pp. 19-29; Jan. 2003.

(Continued)

*Primary Examiner* — Nancy J Leith
(74) *Attorney, Agent, or Firm* — Thomas G. Peterson; Maynard Cooper & Gale

(57) ABSTRACT

This present disclosure relates to a method of producing a proteoglycan having anticoagulant activity, comprising of and providing a cell transfected with a recombinant nucleic acid encoding a core protein having one or more glycosaminoglycan attachment sites; and incubating the cell under conditions to promote the production of a proteoglycan comprising the core protein linked to heparin and/or HS and optionally other glycosaminoglycan chains, and to heparin or heparan sulphate isolated from such proteoglycans that have significant anti-coagulant activity. The invention also relates to a recombinant proteoglycan comprising a core protein and heparin and/or heparan sulfate, to a cell capable of producing a proteoglycan comprising the core protein and heparin and/or heparan sulfate, and to a method of treating or preventing blood coagulation, or a condition associated with blood coagulation, using the recombinant proteoglycan comprising a core protein and heparin and/or heparan sulfate and/or the heparin and/or heparan sulfate isolated from such proteoglycans.

28 Claims, 8 Drawing Sheets
Specification includes a Sequence Listing.

(56) References Cited

OTHER PUBLICATIONS

Marta Busse, et al., "Contributio of EXT1, EXT2, and EXTL3 to Heparan Sulfate Chain Elongation" the Journal of Biological Chemistry; vol. 282, No. 45 pp. 32802-32810; Nov. 9, 2007.
Barbara P. Schnick, et al., Synthesis, secretion and subcellular localization of seglycin proteoglycan in human endothelial cells; Blood, vol. 97, No. 2; pp. 449-458; Jan. 15, 2001.
Megan S. Lord, et al., "Optimization of bioengineered heparin/heparan sulfate production for therapeutic applications," Bioengineered; vol. 8, No. 5; pp. 661-664; 2017.

* cited by examiner

```
                          SEQUENCE LISTING

<160> NUMBER OF SEQ ID NOS: 23

<210> SEQ ID NO 1
<211> LENGTH: 18
<212> TYPE: PRT
<213> ORGANISM: Homo sapiens

<400> SEQUENCE: 1

Ser Gly Ser Gly Phe Gly Ser Gly Ser Gly Ser Gly Ser Gly Ser Gly
1               5                   10                  15

Ser Gly

<210> SEQ ID NO 2
<211> LENGTH: 131
<212> TYPE: PRT
<213> ORGANISM: Homo sapiens

<400> SEQUENCE: 2

Tyr Pro Thr Arg Arg Ala Arg Tyr Gln Trp Val Arg Cys Asn Pro Asp
1               5                   10                  15

Ser Asn Ser Ala Asn Cys Leu Glu Lys Gly Pro Met Phe Glu Leu
            20                  25                  30

Leu Pro Gly Glu Ser Asn Lys Ile Pro Arg Leu Arg Thr Asp Leu Phe
        35                  40                  45

Pro Lys Thr Arg Ile Gln Asp Leu Asn Arg Ile Phe Pro Leu Ser Glu
    50                  55                  60

Asp Tyr Ser Gly Ser Gly Phe Gly Ser Gly Ser Gly Ser Gly Ser Gly
65                  70                  75                  80

Ser Gly Ser Gly Phe Leu Thr Glu Met Glu Gln Asp Tyr Gln Leu Val
                85                  90                  95
```

Asp Glu Ser Asp Ala Phe His Asp Asn Leu Arg Ser Leu Asp Arg Asn
               100                 105                 110

Leu Pro Ser Asp Ser Gln Asp Leu Gly Gln His Gly Leu Glu Glu Asp
        115                 120                 125

Phe Met Leu
        130

<210> SEQ ID NO 3
<211> LENGTH: 158
<212> TYPE: PRT
<213> ORGANISM: Homo sapiens

<400> SEQUENCE: 3

Met Met Gln Lys Leu Leu Lys Cys Ser Arg Leu Val Leu Ala Leu Ala
1               5                   10                  15

Leu Ile Leu Val Leu Glu Ser Ser Val Gln Gly Tyr Pro Thr Arg Arg
            20                  25                  30

Ala Arg Tyr Gln Trp Val Arg Cys Asn Pro Asp Ser Asn Ser Ala Asn
        35                  40                  45

Cys Leu Glu Glu Lys Gly Pro Met Phe Glu Leu Leu Pro Gly Glu Ser
    50                  55                  60

Asn Lys Ile Pro Arg Leu Arg Thr Asp Leu Phe Pro Lys Thr Arg Ile
65                  70                  75                  80

Gln Asp Leu Asn Arg Ile Phe Pro Leu Ser Glu Asp Tyr Ser Gly Ser
                85                  90                  95

Gly Phe Gly Ser Gly Ser Gly Ser Gly Ser Gly Ser Gly Ser Gly Phe
            100                 105                 110

Leu Thr Glu Met Glu Gln Asp Tyr Gln Leu Val Asp Glu Ser Asp Ala
        115                 120                 125

Phe His Asp Asn Leu Arg Ser Leu Asp Arg Asn Leu Pro Ser Asp Ser
    130                 135                 140

Gln Asp Leu Gly Gln His Gly Leu Glu Glu Asp Phe Met Leu
145                 150                 155

<210> SEQ ID NO 4
<211> LENGTH: 477
<212> TYPE: DNA
<213> ORGANISM: Homo sapiens

<400> SEQUENCE: 4
atgatgcaga agctactcaa atgcagtcgg cttgtcctgg ctcttgccct catcctggtt    60
ctggaatcct cagttcaagg ttatcctacg cggagagcca ggtaccaatg ggtgcgctgc   120
aatccagaca gtaattctgc aaactgcctt gaagaaaaag gaccaatgtt cgaactactt   180
ccaggtgaat ccaacaagat cccccgtctg aggactgacc tttttccaaa gacgagaatc   240
caggacttga atcgtatctt cccactttct gaggactact ctggatcagg cttcggctcc   300
ggctccggct ctggatcagg atctggagat ggcttcctaa cggaaatgga acaggattac   360
caactagtag acgaaagtga tgctttccat gacaacctta ggtctcttga caggaatctg   420
ccctcagaca gccaggactt gggtcaacat ggattagaag aggattttat gttataa     477

<210> SEQ ID NO 5
<211> LENGTH: 153
<212> TYPE: PRT
<213> ORGANISM: Rattus norvegicus

<400> SEQUENCE: 5

```
Tyr Pro Ala Arg Arg Ala Arg Tyr Gln Trp Val Arg Cys Lys Pro Asp
1               5                   10                  15

Gly Ile Phe Ala Asn Cys Ile Glu Glu Lys Gly Pro Arg Phe Asp Leu
            20                  25                  30

Ile Ala Glu Glu Ser Asn Val Gly Pro Pro Met Thr Asp Pro Val Leu
            35                  40                  45

Met Arg Gly Phe Pro Asn Asp Phe Phe Pro Ile Ser Asp Asp Tyr Ser
    50                  55                  60

Gly Ser Gly Ser Gly Ser Gly Ser Gly Ser Gly Ser Gly Ser Gly Ser
65              70                  75                  80

Gly Ser Gly Ser Gly Ser Gly Ser Gly Ser Gly Ser Gly Ser Gly Ser
                85                  90                  95

Gly Ser Gly Ser Gly Ser Gly Ser Gly Ser Gly Ser Gly Ser Gly Ser
                100                 105                 110

Leu Ala Asp Met Glu Trp Glu Tyr Gln Pro Thr Asp Glu Asn Asn Ile
                115                 120                 125

Val Tyr Phe Asn Tyr Gly Pro Phe Asp Arg Met Leu Thr Glu Gln Asn
            130                 135                 140

Gln Glu Gln Pro Gly Asp Phe Ile Ile
145                 150

<210> SEQ ID NO 6
<211> LENGTH: 179
<212> TYPE: PRT
<213> ORGANISM: Rattus norvegicus

<400> SEQUENCE: 6

Met Arg Gln Val Pro Val Gly Thr Arg Leu Val Leu Ala Leu Ala Phe
1               5                   10                  15

Val Leu Val Trp Gly Ser Ser Val Gln Gly Tyr Pro Ala Arg Arg Ala
            20                  25                  30

Arg Tyr Gln Trp Val Arg Cys Lys Pro Asp Gly Ile Phe Ala Asn Cys
        35                  40                  45

Ile Glu Glu Lys Gly Pro Arg Phe Asp Leu Ile Ala Glu Glu Ser Asn
50                  55                  60

Val Gly Pro Pro Met Thr Asp Pro Val Leu Met Arg Gly Phe Pro Asn
65              70                  75                  80

Asp Phe Phe Pro Ile Ser Asp Asp Tyr Ser Gly Ser Gly Ser Gly Ser
                85                  90                  95

Gly Ser Gly Ser Gly Ser Gly Ser Gly Ser Gly Ser Gly Ser Gly Ser
                100                 105                 110

Gly Ser Gly Ser Gly Ser Gly Ser Gly Ser Gly Ser Gly Ser Gly Ser
                115                 120                 125

Gly Ser Gly Ser Gly Ser Gly Ser Leu Ala Asp Met Glu Trp
                130                 135                 140

Glu Tyr Gln Pro Thr Asp Glu Asn Asn Ile Val Tyr Phe Asn Tyr Gly
145                 150                 155                 160

Pro Phe Asp Arg Met Leu Thr Glu Gln Asn Gln Glu Gln Pro Gly Asp
                165                 170                 175

Phe Ile Ile

<210> SEQ ID NO 7
<211> LENGTH: 127
<212> TYPE: PRT
<213> ORGANISM: Mus musculus
```

```
<400> SEQUENCE: 7

Tyr Pro Ala Arg Arg Ala Arg Tyr Gln Trp Val Arg Cys Lys Pro Asn
1               5                   10                  15

Gly Phe Phe Ala Asn Cys Ile Glu Glu Lys Gly Pro Gln Phe Asp Leu
            20                  25                  30

Ile Asp Glu Ser Asn Asn Ile Gly Pro Pro Met Asn Asn Pro Val Leu
        35                  40                  45

Met Glu Gly Pro Ser Lys Asp Phe Ile Ser Asn Tyr Asp Asp Tyr Gly
    50                  55                  60

Ser Gly Ser Gly Ser Gly Ser Gly Ser Gly Ser Gly Ser Gly Ser Gly
65                  70                  75                  80

Ser Gly Ser Gly Phe Leu Gly Asp Met Glu Trp Glu Tyr Gln Pro Thr
                85                  90                  95

Asp Glu Ser Asn Ile Val Tyr Phe Asn Tyr Lys Pro Phe Asp Arg Ile
            100                 105                 110

Leu Thr Glu Gln Asn Gln Asp Gln Pro Glu Asp Asp Phe Ile Ile
        115                 120                 125

<210> SEQ ID NO 8
<211> LENGTH: 152
<212> TYPE: PRT
<213> ORGANISM: Mus musculus

<400> SEQUENCE: 8

Met Gln Val Pro Val Gly Ser Arg Leu Val Leu Ala Leu Ala Phe Val
1               5                   10                  15

Leu Val Trp Gly Ser Ser Val Gln Gly Tyr Pro Ala Arg Ala Arg
            20                  25                  30

Tyr Gln Trp Val Arg Cys Lys Pro Asn Gly Phe Phe Ala Asn Cys Ile
        35                  40                  45

Glu Glu Lys Gly Pro Gln Phe Asp Leu Ile Asp Glu Ser Asn Asn Ile
    50                  55                  60

Gly Pro Pro Met Asn Asn Pro Val Leu Met Glu Gly Pro Ser Lys Asp
65                  70                  75                  80

Phe Ile Ser Asn Tyr Asp Asp Tyr Gly Ser Gly Ser Gly Ser Gly Ser
                85                  90                  95

Gly Ser Gly Ser Gly Ser Gly Ser Gly Ser Gly Ser Gly Phe Leu Gly
            100                 105                 110

Asp Met Glu Trp Glu Tyr Gln Pro Thr Asp Glu Ser Asn Ile Val Tyr
        115                 120                 125

Phe Asn Tyr Lys Pro Phe Asp Arg Ile Leu Thr Glu Gln Asn Gln Asp
    130                 135                 140

Gln Pro Glu Asp Asp Phe Ile Ile
145                 150

<210> SEQ ID NO 9
<211> LENGTH: 18
<212> TYPE: PRT
<213> ORGANISM: Artificial Sequence
<220> FEATURE:
<223> OTHER INFORMATION: variant of GAG attachment site from human
      serglycin
<220> FEATURE:
<221> NAME/KEY: X
<222> LOCATION: (5)..(6)
<223> OTHER INFORMATION: any amino acid

<400> SEQUENCE: 9
```

```
Ser Gly Ser Gly Xaa Xaa Ser Gly Ser Gly Ser Gly Ser Gly
1               5                   10                  15

Ser Gly
```

<210> SEQ ID NO 10
<211> LENGTH: 4
<212> TYPE: PRT
<213> ORGANISM: Homo sapiens

<400> SEQUENCE: 10

```
Ser Gly Ser Gly
1
```

<210> SEQ ID NO 11
<211> LENGTH: 14
<212> TYPE: PRT
<213> ORGANISM: Artificial Sequence
<220> FEATURE:
<223> OTHER INFORMATION: variant of GAG attachment site from human
      perlecan
<220> FEATURE:
<221> NAME/KEY: X
<222> LOCATION: (4)..(6)
<223> OTHER INFORMATION: any amino acid
<220> FEATURE:
<221> NAME/KEY: X
<222> LOCATION: (10)..(11)
<223> OTHER INFORMATION: any amino acid

<400> SEQUENCE: 11

```
Ser Gly Asp Xaa Xaa Xaa Ser Gly Asp Xaa Xaa Ser Gly Asp
1               5                   10
```

<210> SEQ ID NO 12
<211> LENGTH: 48
<212> TYPE: PRT
<213> ORGANISM: Rattus norvegicus

<400> SEQUENCE: 12

```
Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly Ser Gly
                20                  25                  30

Ser Gly Ser Gly Ser Gly Ser Gly Ser Gly Ser Gly Ser Gly Ser Gly
            35                  40                  45
```

<210> SEQ ID NO 13
<211> LENGTH: 20
<212> TYPE: PRT
<213> ORGANISM: Mus musculus

<400> SEQUENCE: 13

```
Ser Gly Ser Gly Ser Gly Ser Gly Ser Gly Ser Gly Ser Gly Ser Gly
1               5                   10                  15

Ser Gly Ser Gly
            20
```

<210> SEQ ID NO 14
<211> LENGTH: 14
<212> TYPE: PRT
<213> ORGANISM: Homo sapiens

<400> SEQUENCE: 14

```
Ser Gly Asp Asp Leu Gly Ser Gly Asp Leu Gly Ser Gly Asp
1               5                   10
```

<210> SEQ ID NO 15
<211> LENGTH: 14
<212> TYPE: PRT
<213> ORGANISM: Mus musculus

<400> SEQUENCE: 15

Ser Gly Asp Gly Leu Gly Ser Gly Asp Val Gly Ser Gly Asp
1               5                   10

<210> SEQ ID NO 16
<211> LENGTH: 27
<212> TYPE: PRT
<213> ORGANISM: Homo sapiens

<400> SEQUENCE: 16

Met Met Gln Lys Leu Leu Lys Cys Ser Arg Leu Val Leu Ala Leu Ala
1               5                   10                  15

Leu Ile Leu Val Leu Glu Ser Ser Val Gln Gly
            20                  25

<210> SEQ ID NO 17
<211> LENGTH: 26
<212> TYPE: PRT
<213> ORGANISM: Rattus norvegicus

<400> SEQUENCE: 17

Met Arg Gln Val Pro Val Gly Thr Arg Leu Val Leu Ala Leu Ala Phe
1               5                   10                  15

Val Leu Val Trp Gly Ser Ser Val Gln Gly
            20                  25

<210> SEQ ID NO 18
<211> LENGTH: 25
<212> TYPE: PRT
<213> ORGANISM: Mus musculus

<400> SEQUENCE: 18

Met Gln Val Pro Val Gly Ser Arg Leu Val Leu Ala Leu Ala Phe Val
1               5                   10                  15

Leu Val Trp Gly Ser Ser Val Gln Gly
            20                  25

<210> SEQ ID NO 19
<211> LENGTH: 22
<212> TYPE: PRT
<213> ORGANISM: Homo sapiens

<400> SEQUENCE: 19

Met Gly Trp Arg Ala Pro Gly Ala Leu Leu Leu Ala Leu Leu Leu His
1               5                   10                  15

Gly Arg Leu Leu Ala Val
            20

<210> SEQ ID NO 20
<211> LENGTH: 17
<212> TYPE: PRT
<213> ORGANISM: Homo sapiens

<400> SEQUENCE: 20

Met Arg Ala Trp Ile Phe Phe Leu Leu Cys Leu Ala Gly Arg Ala Leu
1               5                   10                  15

Ala

<210> SEQ ID NO 21
<211> LENGTH: 4391
<212> TYPE: PRT
<213> ORGANISM: Homo sapiens

<400> SEQUENCE: 21

```
Met Gly Trp Arg Ala Pro Gly Ala Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
        35                  40                  45

Thr His Ser Tyr Leu Ser Asp Asp Glu Tyr Met Leu Ala Asp Ser Ile
    50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
        115                 120                 125

Asp Gln Val Val Ser Val Val Phe Ile Lys Glu Leu Asp Gly Trp Val
    130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
        195                 200                 205

Tyr Asn Glu Cys Val Ala Leu Glu Tyr Arg Cys Asp Arg Arg Pro Asp
    210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
        275                 280                 285

Glu Ala Ala Cys Arg Asn Gly His Cys Ile Pro Arg Asp Tyr Leu Cys
    290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
        355                 360                 365
```

```
Gly Pro Thr Gln Phe Arg Cys Val Ser Thr Asn Met Cys Ile Pro Ala
    370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Arg Glu Ser Ile
                405                 410                 415

Gln Ala Ser Arg Gly Gln Thr Val Thr Phe Thr Cys Val Ala Ile Gly
                420                 425                 430

Val Pro Thr Pro Ile Ile Asn Trp Arg Leu Asn Trp Gly His Ile Pro
            435                 440                 445

Ser His Pro Arg Val Thr Val Thr Ser Glu Gly Gly Arg Gly Thr Leu
        450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu His Ser Ala Ala Cys Leu Pro Cys Phe Cys Phe Gly Ile Thr Ser
        515                 520                 525

Val Cys Gln Ser Thr Arg Arg Phe Arg Asp Gln Ile Arg Leu Arg Phe
    530                 535                 540

Asp Gln Pro Asp Asp Phe Lys Gly Val Asn Val Thr Met Pro Ala Gln
545                 550                 555                 560

Pro Gly Thr Pro Pro Leu Ser Ser Thr Gln Leu Gln Ile Asp Pro Ser
                565                 570                 575

Leu His Glu Phe Gln Leu Val Asp Leu Ser Arg Arg Phe Leu Val His
            580                 585                 590

Asp Ser Phe Trp Ala Leu Pro Glu Gln Phe Leu Gly Asn Lys Val Asp
        595                 600                 605

Ser Tyr Gly Gly Ser Leu Arg Tyr Asn Val Arg Tyr Glu Leu Ala Arg
610                 615                 620

Gly Met Leu Glu Pro Val Gln Arg Pro Asp Val Val Leu Val Gly Ala
625                 630                 635                 640

Gly Tyr Arg Leu Leu Ser Arg His Thr Pro Thr Gln Pro Gly Ala
                645                 650                 655

Leu Asn Gln Arg Gln Val Gln Phe Ser Glu Glu His Trp Val His Glu
            660                 665                 670

Ser Gly Arg Pro Val Gln Arg Ala Glu Leu Leu Gln Val Leu Gln Ser
        675                 680                 685

Leu Glu Ala Val Leu Ile Gln Thr Val Tyr Asn Thr Lys Met Ala Ser
    690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
                725                 730                 735

Tyr Ser Gly Leu Ser Cys Glu Ser Cys Asp Ala His Phe Thr Arg Val
            740                 745                 750

Pro Gly Gly Pro Tyr Leu Gly Thr Cys Ser Gly Cys Ser Cys Asn Gly
        755                 760                 765

His Ala Ser Ser Cys Asp Pro Val Tyr Gly His Cys Leu Asn Cys Gln
    770                 775                 780

His Asn Thr Glu Gly Pro Gln Cys Asn Lys Cys Lys Ala Gly Phe Phe
```

-continued

```
            785                 790                 795                 800
Gly Asp Ala Met Lys Ala Thr Ala Thr Ser Cys Arg Pro Cys Pro Cys
                    805                 810                 815
Pro Tyr Ile Asp Ala Ser Arg Arg Phe Ser Asp Thr Cys Phe Leu Asp
                    820                 825                 830
Thr Asp Gly Gln Ala Thr Cys Asp Ala Cys Ala Pro Gly Tyr Thr Gly
                    835                 840                 845
Arg Arg Cys Glu Ser Cys Ala Pro Gly Tyr Glu Gly Asn Pro Ile Gln
            850                 855                 860
Pro Gly Gly Lys Cys Arg Pro Val Asn Gln Glu Ile Val Arg Cys Asp
865                 870                 875                 880
Glu Arg Gly Ser Met Gly Thr Ser Gly Glu Ala Cys Arg Cys Lys Asn
                    885                 890                 895
Asn Val Val Gly Arg Leu Cys Asn Glu Cys Ala Asp Gly Ser Phe His
                    900                 905                 910
Leu Ser Thr Arg Asn Pro Asp Gly Cys Leu Lys Cys Phe Cys Met Gly
                    915                 920                 925
Val Ser Arg His Cys Thr Ser Ser Trp Ser Arg Ala Gln Leu His
            930                 935                 940
Gly Ala Ser Glu Glu Pro Gly His Phe Ser Leu Thr Asn Ala Ala Ser
945                 950                 955                 960
Thr His Thr Thr Asn Glu Gly Ile Phe Ser Pro Thr Pro Gly Glu Leu
                    965                 970                 975
Gly Phe Ser Ser Phe His Arg Leu Leu Ser Gly Pro Tyr Phe Trp Ser
                    980                 985                 990
Leu Pro Ser Arg Phe Leu Gly Asp Lys Val Thr Ser Tyr Gly Gly Glu
            995                 1000                1005
Leu Arg Phe Thr Val Thr Gln Arg Ser Gln Pro Gly Ser Thr Pro
            1010                1015                1020
Leu His Gly Gln Pro Leu Val Val Leu Gln Gly Asn Asn Ile Ile
            1025                1030                1035
Leu Glu His His Val Ala Gln Glu Pro Ser Pro Gly Gln Pro Ser
            1040                1045                1050
Thr Phe Ile Val Pro Phe Arg Glu Gln Ala Trp Gln Arg Pro Asp
            1055                1060                1065
Gly Gln Pro Ala Thr Arg Glu His Leu Leu Met Ala Leu Ala Gly
            1070                1075                1080
Ile Asp Thr Leu Leu Ile Arg Ala Ser Tyr Ala Gln Gln Pro Ala
            1085                1090                1095
Glu Ser Arg Val Ser Gly Ile Ser Met Asp Val Ala Val Pro Glu
            1100                1105                1110
Glu Thr Gly Gln Asp Pro Ala Leu Glu Val Glu Gln Cys Ser Cys
            1115                1120                1125
Pro Pro Gly Tyr Arg Gly Pro Ser Cys Gln Asp Cys Asp Thr Gly
            1130                1135                1140
Tyr Thr Arg Thr Pro Ser Gly Leu Tyr Leu Gly Thr Cys Glu Arg
            1145                1150                1155
Cys Ser Cys His Gly His Ser Glu Ala Cys Glu Pro Glu Thr Gly
            1160                1165                1170
Ala Cys Gln Gly Cys Gln His His Thr Glu Gly Pro Arg Cys Glu
            1175                1180                1185
Gln Cys Gln Pro Gly Tyr Tyr Gly Asp Ala Gln Arg Gly Thr Pro
            1190                1195                1200
```

```
Gln Asp Cys Gln Leu Cys Pro Cys Tyr Gly Asp Pro Ala Ala Gly
1205                1210                1215

Gln Ala Ala His Thr Cys Phe Leu Asp Thr Asp Gly His Pro Thr
1220                1225                1230

Cys Asp Ala Cys Ser Pro Gly His Ser Gly Arg His Cys Glu Arg
1235                1240                1245

Cys Ala Pro Gly Tyr Tyr Gly Asn Pro Ser Gln Gly Gln Pro Cys
1250                1255                1260

Gln Arg Asp Ser Gln Val Pro Gly Pro Ile Gly Cys Asn Cys Asp
1265                1270                1275

Pro Gln Gly Ser Val Ser Gln Cys Asp Ala Ala Gly Gln Cys
1280                1285                1290

Gln Cys Lys Ala Gln Val Glu Gly Leu Thr Cys Ser His Cys Arg
1295                1300                1305

Pro His His Phe His Leu Ser Ala Ser Asn Pro Asp Gly Cys Leu
1310                1315                1320

Pro Cys Phe Cys Met Gly Ile Thr Gln Gln Cys Ala Ser Ser Ala
1325                1330                1335

Tyr Thr Arg His Leu Ile Ser Thr His Phe Ala Pro Gly Asp Phe
1340                1345                1350

Gln Gly Phe Ala Leu Val Asn Pro Gln Arg Asn Ser Arg Leu Thr
1355                1360                1365

Gly Glu Phe Thr Val Glu Pro Val Pro Glu Gly Ala Gln Leu Ser
1370                1375                1380

Phe Gly Asn Phe Ala Gln Leu Gly His Glu Ser Phe Tyr Trp Gln
1385                1390                1395

Leu Pro Glu Thr Tyr Gln Gly Asp Lys Val Ala Ala Tyr Gly Gly
1400                1405                1410

Lys Leu Arg Tyr Thr Leu Ser Tyr Thr Ala Gly Pro Gln Gly Ser
1415                1420                1425

Pro Leu Ser Asp Pro Asp Val Gln Ile Thr Gly Asn Asn Ile Met
1430                1435                1440

Leu Val Ala Ser Gln Pro Ala Leu Gln Gly Pro Glu Arg Arg Ser
1445                1450                1455

Tyr Glu Ile Met Phe Arg Glu Glu Phe Trp Arg Arg Pro Asp Gly
1460                1465                1470

Gln Pro Ala Thr Arg Glu His Leu Leu Met Ala Leu Ala Asp Leu
1475                1480                1485

Asp Glu Leu Leu Ile Arg Ala Thr Phe Ser Ser Val Pro Leu Val
1490                1495                1500

Ala Ser Ile Ser Ala Val Ser Leu Glu Val Ala Gln Pro Gly Pro
1505                1510                1515

Ser Asn Arg Pro Arg Ala Leu Glu Val Glu Glu Cys Arg Cys Pro
1520                1525                1530

Pro Gly Tyr Ile Gly Leu Ser Cys Gln Asp Cys Ala Pro Gly Tyr
1535                1540                1545

Thr Arg Thr Gly Ser Gly Leu Tyr Leu Gly His Cys Glu Leu Cys
1550                1555                1560

Glu Cys Asn Gly His Ser Asp Leu Cys His Pro Glu Thr Gly Ala
1565                1570                1575

Cys Ser Gln Cys Gln His Asn Ala Ala Gly Glu Phe Cys Glu Leu
1580                1585                1590
```

```
Cys Ala Pro Gly Tyr Tyr Gly Asp Ala Thr Ala Gly Thr Pro Glu
1595                1600                1605

Asp Cys Gln Pro Cys Ala Cys Pro Leu Thr Asn Pro Glu Asn Met
1610                1615                1620

Phe Ser Arg Thr Cys Glu Ser Leu Gly Ala Gly Gly Tyr Arg Cys
1625                1630                1635

Thr Ala Cys Glu Pro Gly Tyr Thr Gly Gln Tyr Cys Glu Gln Cys
1640                1645                1650

Gly Pro Gly Tyr Val Gly Asn Pro Ser Val Gln Gly Gly Gln Cys
1655                1660                1665

Leu Pro Glu Thr Asn Gln Ala Pro Leu Val Val Glu Val His Pro
1670                1675                1680

Ala Arg Ser Ile Val Pro Gln Gly Gly Ser His Ser Leu Arg Cys
1685                1690                1695

Gln Val Ser Gly Ser Pro Pro His Tyr Phe Tyr Trp Ser Arg Glu
1700                1705                1710

Asp Gly Arg Pro Val Pro Ser Gly Thr Gln Gln Arg His Gln Gly
1715                1720                1725

Ser Glu Leu His Phe Pro Ser Val Gln Pro Ser Asp Ala Gly Val
1730                1735                1740

Tyr Ile Cys Thr Cys Arg Asn Leu His Gln Ser Asn Thr Ser Arg
1745                1750                1755

Ala Glu Leu Leu Val Thr Glu Ala Pro Ser Lys Pro Ile Thr Val
1760                1765                1770

Thr Val Glu Glu Gln Arg Ser Gln Ser Val Arg Pro Gly Ala Asp
1775                1780                1785

Val Thr Phe Ile Cys Thr Ala Lys Ser Lys Ser Pro Ala Tyr Thr
1790                1795                1800

Leu Val Trp Thr Arg Leu His Asn Gly Lys Leu Pro Thr Arg Ala
1805                1810                1815

Met Asp Phe Asn Gly Ile Leu Thr Ile Arg Asn Val Gln Leu Ser
1820                1825                1830

Asp Ala Gly Thr Tyr Val Cys Thr Gly Ser Asn Met Phe Ala Met
1835                1840                1845

Asp Gln Gly Thr Ala Thr Leu His Val Gln Ala Ser Gly Thr Leu
1850                1855                1860

Ser Ala Pro Val Val Ser Ile His Pro Pro Gln Leu Thr Val Gln
1865                1870                1875

Pro Gly Gln Leu Ala Glu Phe Arg Cys Ser Ala Thr Gly Ser Pro
1880                1885                1890

Thr Pro Thr Leu Glu Trp Thr Gly Gly Pro Gly Gly Gln Leu Pro
1895                1900                1905

Ala Lys Ala Gln Ile His Gly Gly Ile Leu Arg Leu Pro Ala Val
1910                1915                1920

Glu Pro Thr Asp Gln Ala Gln Tyr Leu Cys Arg Ala His Ser Ser
1925                1930                1935

Ala Gly Gln Gln Val Ala Arg Ala Val Leu His Val His Gly Gly
1940                1945                1950

Gly Gly Pro Arg Val Gln Val Ser Pro Glu Arg Thr Gln Val His
1955                1960                1965

Ala Gly Arg Thr Val Arg Leu Tyr Cys Arg Ala Ala Gly Val Pro
1970                1975                1980

Ser Ala Thr Ile Thr Trp Arg Lys Glu Gly Gly Ser Leu Pro Pro
```

-continued

```
            1985                1990                1995
Gln Ala Arg Ser Glu Arg Thr Asp Ile Ala Thr Leu Leu Ile Pro
            2000                2005                2010
Ala Ile Thr Thr Ala Asp Ala Gly Phe Tyr Leu Cys Val Ala Thr
            2015                2020                2025
Ser Pro Ala Gly Thr Ala Gln Ala Arg Met Gln Val Val Val Leu
            2030                2035                2040
Ser Ala Ser Asp Ala Ser Pro Pro Gly Val Lys Ile Glu Ser Ser
            2045                2050                2055
Ser Pro Ser Val Thr Glu Gly Gln Thr Leu Asp Leu Asn Cys Val
            2060                2065                2070
Val Ala Gly Ser Ala His Ala Gln Val Thr Trp Tyr Arg Arg Gly
            2075                2080                2085
Gly Ser Leu Pro Pro His Thr Gln Val His Gly Ser Arg Leu Arg
            2090                2095                2100
Leu Pro Gln Val Ser Pro Ala Asp Ser Gly Glu Tyr Val Cys Arg
            2105                2110                2115
Val Glu Asn Gly Ser Gly Pro Lys Glu Ala Ser Ile Thr Val Ser
            2120                2125                2130
Val Leu His Gly Thr His Ser Gly Pro Ser Tyr Thr Pro Val Pro
            2135                2140                2145
Gly Ser Thr Arg Pro Ile Arg Ile Glu Pro Ser Ser Ser His Val
            2150                2155                2160
Ala Glu Gly Gln Thr Leu Asp Leu Asn Cys Val Val Pro Gly Gln
            2165                2170                2175
Ala His Ala Gln Val Thr Trp His Lys Arg Gly Gly Ser Leu Pro
            2180                2185                2190
Ala Arg His Gln Thr His Gly Ser Leu Leu Arg Leu His Gln Val
            2195                2200                2205
Thr Pro Ala Asp Ser Gly Glu Tyr Val Cys His Val Val Gly Thr
            2210                2215                2220
Ser Gly Pro Leu Glu Ala Ser Val Leu Val Thr Ile Glu Ala Ser
            2225                2230                2235
Val Ile Pro Gly Pro Ile Pro Pro Val Arg Ile Glu Ser Ser Ser
            2240                2245                2250
Ser Thr Val Ala Glu Gly Gln Thr Leu Asp Leu Ser Cys Val Val
            2255                2260                2265
Ala Gly Gln Ala His Ala Gln Val Thr Trp Tyr Lys Arg Gly Gly
            2270                2275                2280
Ser Leu Pro Ala Arg His Gln Val Arg Gly Ser Arg Leu Tyr Ile
            2285                2290                2295
Phe Gln Ala Ser Pro Ala Asp Ala Gly Gln Tyr Val Cys Arg Ala
            2300                2305                2310
Ser Asn Gly Met Glu Ala Ser Ile Thr Val Thr Val Thr Gly Thr
            2315                2320                2325
Gln Gly Ala Asn Leu Ala Tyr Pro Ala Gly Ser Thr Gln Pro Ile
            2330                2335                2340
Arg Ile Glu Pro Ser Ser Ser Gln Val Ala Glu Gly Gln Thr Leu
            2345                2350                2355
Asp Leu Asn Cys Val Val Pro Gly Gln Ser His Ala Gln Val Thr
            2360                2365                2370
Trp His Lys Arg Gly Gly Ser Leu Pro Val Arg His Gln Thr His
            2375                2380                2385
```

```
Gly Ser Leu Leu Arg Leu Tyr Gln Ala Ser Pro Ala Asp Ser Gly
    2390            2395            2400

Glu Tyr Val Cys Arg Val Leu Gly Ser Ser Val Pro Leu Glu Ala
    2405            2410            2415

Ser Val Leu Val Thr Ile Glu Pro Ala Gly Ser Val Pro Ala Leu
    2420            2425            2430

Gly Val Thr Pro Thr Val Arg Ile Glu Ser Ser Ser Gln Val
    2435            2440            2445

Ala Glu Gly Gln Thr Leu Asp Leu Asn Cys Leu Val Ala Gly Gln
    2450            2455            2460

Ala His Ala Gln Val Thr Trp His Lys Arg Gly Gly Ser Leu Pro
    2465            2470            2475

Ala Arg His Gln Val His Gly Ser Arg Leu Arg Leu Leu Gln Val
    2480            2485            2490

Thr Pro Ala Asp Ser Gly Glu Tyr Val Cys Arg Val Val Gly Ser
    2495            2500            2505

Ser Gly Thr Gln Glu Ala Ser Val Leu Val Thr Ile Gln Gln Arg
    2510            2515            2520

Leu Ser Gly Ser His Ser Gln Gly Val Ala Tyr Pro Val Arg Ile
    2525            2530            2535

Glu Ser Ser Ser Ala Ser Leu Ala Asn Gly His Thr Leu Asp Leu
    2540            2545            2550

Asn Cys Leu Val Ala Ser Gln Ala Pro His Thr Ile Thr Trp Tyr
    2555            2560            2565

Lys Arg Gly Gly Ser Leu Pro Ser Arg His Gln Ile Val Gly Ser
    2570            2575            2580

Arg Leu Arg Ile Pro Gln Val Thr Pro Ala Asp Ser Gly Glu Tyr
    2585            2590            2595

Val Cys His Val Ser Asn Gly Ala Gly Ser Arg Glu Thr Ser Leu
    2600            2605            2610

Ile Val Thr Ile Gln Gly Ser Gly Ser Ser His Val Pro Ser Val
    2615            2620            2625

Ser Pro Pro Ile Arg Ile Glu Ser Ser Ser Pro Thr Val Val Glu
    2630            2635            2640

Gly Gln Thr Leu Asp Leu Asn Cys Val Val Ala Arg Gln Pro Gln
    2645            2650            2655

Ala Ile Ile Thr Trp Tyr Lys Arg Gly Gly Ser Leu Pro Ser Arg
    2660            2665            2670

His Gln Thr His Gly Ser His Leu Arg Leu His Gln Met Ser Val
    2675            2680            2685

Ala Asp Ser Gly Glu Tyr Val Cys Arg Ala Asn Asn Asn Ile Asp
    2690            2695            2700

Ala Leu Glu Ala Ser Ile Val Ile Ser Val Ser Pro Ser Ala Gly
    2705            2710            2715

Ser Pro Ser Ala Pro Gly Ser Ser Met Pro Ile Arg Ile Glu Ser
    2720            2725            2730

Ser Ser Ser His Val Ala Glu Gly Glu Thr Leu Asp Leu Asn Cys
    2735            2740            2745

Val Val Pro Gly Gln Ala His Ala Gln Val Thr Trp His Lys Arg
    2750            2755            2760

Gly Gly Ser Leu Pro Ser His His Gln Thr Arg Gly Ser Arg Leu
    2765            2770            2775
```

-continued

Arg Leu His His Val Ser Pro Ala Asp Ser Gly Glu Tyr Val Cys
2780                2785                2790

Arg Val Met Gly Ser Ser Gly Pro Leu Glu Ala Ser Val Leu Val
2795                2800                2805

Thr Ile Glu Ala Ser Gly Ser Ser Ala Val His Val Pro Ala Pro
2810                2815                2820

Gly Gly Ala Pro Pro Ile Arg Ile Glu Pro Ser Ser Ser Arg Val
2825                2830                2835

Ala Glu Gly Gln Thr Leu Asp Leu Lys Cys Val Val Pro Gly Gln
2840                2845                2850

Ala His Ala Gln Val Thr Trp His Lys Arg Gly Gly Asn Leu Pro
2855                2860                2865

Ala Arg His Gln Val His Gly Pro Leu Leu Arg Leu Asn Gln Val
2870                2875                2880

Ser Pro Ala Asp Ser Gly Glu Tyr Ser Cys Gln Val Thr Gly Ser
2885                2890                2895

Ser Gly Thr Leu Glu Ala Ser Val Leu Val Thr Ile Glu Pro Ser
2900                2905                2910

Ser Pro Gly Pro Ile Pro Ala Pro Gly Leu Ala Gln Pro Ile Tyr
2915                2920                2925

Ile Glu Ala Ser Ser Ser His Val Thr Glu Gly Gln Thr Leu Asp
2930                2935                2940

Leu Asn Cys Val Val Pro Gly Gln Ala His Ala Gln Val Thr Trp
2945                2950                2955

Tyr Lys Arg Gly Gly Ser Leu Pro Ala Arg His Gln Thr His Gly
2960                2965                2970

Ser Gln Leu Arg Leu His Leu Val Ser Pro Ala Asp Ser Gly Glu
2975                2980                2985

Tyr Val Cys Arg Ala Ala Ser Gly Pro Gly Pro Glu Gln Glu Ala
2990                2995                3000

Ser Phe Thr Val Thr Val Pro Pro Ser Glu Gly Ser Ser Tyr Arg
3005                3010                3015

Leu Arg Ser Pro Val Ile Ser Ile Asp Pro Pro Ser Ser Thr Val
3020                3025                3030

Gln Gln Gly Gln Asp Ala Ser Phe Lys Cys Leu Ile His Asp Gly
3035                3040                3045

Ala Ala Pro Ile Ser Leu Glu Trp Lys Thr Arg Asn Gln Glu Leu
3050                3055                3060

Glu Asp Asn Val His Ile Ser Pro Asn Gly Ser Ile Ile Thr Ile
3065                3070                3075

Val Gly Thr Arg Pro Ser Asn His Gly Thr Tyr Arg Cys Val Ala
3080                3085                3090

Ser Asn Ala Tyr Gly Val Ala Gln Ser Val Val Asn Leu Ser Val
3095                3100                3105

His Gly Pro Pro Thr Val Ser Val Leu Pro Glu Gly Pro Val Trp
3110                3115                3120

Val Lys Val Gly Lys Ala Val Thr Leu Glu Cys Val Ser Ala Gly
3125                3130                3135

Glu Pro Arg Ser Ser Ala Arg Trp Thr Arg Ile Ser Ser Thr Pro
3140                3145                3150

Ala Lys Leu Glu Gln Arg Thr Tyr Gly Leu Met Asp Ser His Ala
3155                3160                3165

Val Leu Gln Ile Ser Ser Ala Lys Pro Ser Asp Ala Gly Thr Tyr

-continued

```
                3170                3175                3180
Val Cys Leu Ala Gln Asn Ala Leu Gly Thr Ala Gln Lys Gln Val
    3185                3190                3195
Glu Val Ile Val Asp Thr Gly Ala Met Ala Pro Gly Ala Pro Gln
    3200                3205                3210
Val Gln Ala Glu Glu Ala Glu Leu Thr Val Glu Ala Gly His Thr
    3215                3220                3225
Ala Thr Leu Arg Cys Ser Ala Thr Gly Ser Pro Ala Pro Thr Ile
    3230                3235                3240
His Trp Ser Lys Leu Arg Ser Pro Leu Pro Trp Gln His Arg Leu
    3245                3250                3255
Glu Gly Asp Thr Leu Ile Ile Pro Arg Val Ala Gln Gln Asp Ser
    3260                3265                3270
Gly Gln Tyr Ile Cys Asn Ala Thr Ser Pro Ala Gly His Ala Glu
    3275                3280                3285
Ala Thr Ile Ile Leu His Val Glu Ser Pro Pro Tyr Ala Thr Thr
    3290                3295                3300
Val Pro Glu His Ala Ser Val Gln Ala Gly Glu Thr Val Gln Leu
    3305                3310                3315
Gln Cys Leu Ala His Gly Thr Pro Pro Leu Thr Phe Gln Trp Ser
    3320                3325                3330
Arg Val Gly Ser Ser Leu Pro Gly Arg Ala Thr Ala Arg Asn Glu
    3335                3340                3345
Leu Leu His Phe Glu Arg Ala Ala Pro Glu Asp Ser Gly Arg Tyr
    3350                3355                3360
Arg Cys Arg Val Thr Asn Lys Val Gly Ser Ala Glu Ala Phe Ala
    3365                3370                3375
Gln Leu Leu Val Gln Gly Pro Pro Gly Ser Leu Pro Ala Thr Ser
    3380                3385                3390
Ile Pro Ala Gly Ser Thr Pro Thr Val Gln Val Thr Pro Gln Leu
    3395                3400                3405
Glu Thr Lys Ser Ile Gly Ala Ser Val Glu Phe His Cys Ala Val
    3410                3415                3420
Pro Ser Asp Gln Gly Thr Gln Leu Arg Trp Phe Lys Glu Gly Gly
    3425                3430                3435
Gln Leu Pro Pro Gly His Ser Val Gln Asp Gly Val Leu Arg Ile
    3440                3445                3450
Gln Asn Leu Asp Gln Ser Cys Gln Gly Thr Tyr Ile Cys Gln Ala
    3455                3460                3465
His Gly Pro Trp Gly Lys Ala Gln Ala Ser Ala Gln Leu Val Ile
    3470                3475                3480
Gln Ala Leu Pro Ser Val Leu Ile Asn Ile Arg Thr Ser Val Gln
    3485                3490                3495
Thr Val Val Val Gly His Ala Val Glu Phe Glu Cys Leu Ala Leu
    3500                3505                3510
Gly Asp Pro Lys Pro Gln Val Thr Trp Ser Lys Val Gly Gly His
    3515                3520                3525
Leu Arg Pro Gly Ile Val Gln Ser Gly Gly Val Val Arg Ile Ala
    3530                3535                3540
His Val Glu Leu Ala Asp Ala Gly Gln Tyr Arg Cys Thr Ala Thr
    3545                3550                3555
Asn Ala Ala Gly Thr Thr Gln Ser His Val Leu Leu Leu Val Gln
    3560                3565                3570
```

```
Ala Leu Pro Gln Ile Ser Met Pro Gln Glu Val Arg Val Pro Ala
    3575                3580                3585

Gly Ser Ala Ala Val Phe Pro Cys Ile Ala Ser Gly Tyr Pro Thr
    3590                3595                3600

Pro Asp Ile Ser Trp Ser Lys Leu Asp Gly Ser Leu Pro Pro Asp
    3605                3610                3615

Ser Arg Leu Glu Asn Asn Met Leu Met Leu Pro Ser Val Arg Pro
    3620                3625                3630

Gln Asp Ala Gly Thr Tyr Val Cys Thr Ala Thr Asn Arg Gln Gly
    3635                3640                3645

Lys Val Lys Ala Phe Ala His Leu Gln Val Pro Glu Arg Val Val
    3650                3655                3660

Pro Tyr Phe Thr Gln Thr Pro Tyr Ser Phe Leu Pro Leu Pro Thr
    3665                3670                3675

Ile Lys Asp Ala Tyr Arg Lys Phe Glu Ile Lys Ile Thr Phe Arg
    3680                3685                3690

Pro Asp Ser Ala Asp Gly Met Leu Leu Tyr Asn Gly Gln Lys Arg
    3695                3700                3705

Val Pro Gly Ser Pro Thr Asn Leu Ala Asn Arg Gln Pro Asp Phe
    3710                3715                3720

Ile Ser Phe Gly Leu Val Gly Gly Arg Pro Glu Phe Arg Phe Asp
    3725                3730                3735

Ala Gly Ser Gly Met Ala Thr Ile Arg His Pro Thr Pro Leu Ala
    3740                3745                3750

Leu Gly His Phe His Thr Val Thr Leu Leu Arg Ser Leu Thr Gln
    3755                3760                3765

Gly Ser Leu Ile Val Gly Asp Leu Ala Pro Val Asn Gly Thr Ser
    3770                3775                3780

Gln Gly Lys Phe Gln Gly Leu Asp Leu Asn Glu Glu Leu Tyr Leu
    3785                3790                3795

Gly Gly Tyr Pro Asp Tyr Gly Ala Ile Pro Lys Ala Gly Leu Ser
    3800                3805                3810

Ser Gly Phe Ile Gly Cys Val Arg Glu Leu Arg Ile Gln Gly Glu
    3815                3820                3825

Glu Ile Val Phe His Asp Leu Asn Leu Thr Ala His Gly Ile Ser
    3830                3835                3840

His Cys Pro Thr Cys Arg Asp Arg Pro Cys Gln Asn Gly Gly Gln
    3845                3850                3855

Cys His Asp Ser Glu Ser Ser Tyr Val Cys Val Cys Pro Ala
    3860                3865                3870

Gly Phe Thr Gly Ser Arg Cys Glu His Ser Gln Ala Leu His Cys
    3875                3880                3885

His Pro Glu Ala Cys Gly Pro Asp Ala Thr Cys Val Asn Arg Pro
    3890                3895                3900

Asp Gly Arg Gly Tyr Thr Cys Arg Cys His Leu Gly Arg Ser Gly
    3905                3910                3915

Leu Arg Cys Glu Glu Gly Val Thr Val Thr Thr Pro Ser Leu Ser
    3920                3925                3930

Gly Ala Gly Ser Tyr Leu Ala Leu Pro Ala Leu Thr Asn Thr His
    3935                3940                3945

His Glu Leu Arg Leu Asp Val Glu Phe Lys Pro Leu Ala Pro Asp
    3950                3955                3960
```

| | | | | | | | | | | | |
|---|---|---|---|---|---|---|---|---|---|---|---|
| Gly | Val | Leu | Leu | Phe | Ser | Gly | Gly | Lys | Ser | Gly | Pro | Val | Glu | Asp |
| | 3965 | | | | | 3970 | | | | 3975 | |
| Phe | Val | Ser | Leu | Ala | Met | Val | Gly | Gly | His | Leu | Glu | Phe | Arg | Tyr |
| | 3980 | | | | | 3985 | | | | 3990 | |
| Glu | Leu | Gly | Ser | Gly | Leu | Ala | Val | Leu | Arg | Ser | Ala | Glu | Pro | Leu |
| | 3995 | | | | | 4000 | | | | 4005 | |
| Ala | Leu | Gly | Arg | Trp | His | Arg | Val | Ser | Ala | Glu | Arg | Leu | Asn | Lys |
| | 4010 | | | | | 4015 | | | | 4020 | |
| Asp | Gly | Ser | Leu | Arg | Val | Asn | Gly | Gly | Arg | Pro | Val | Leu | Arg | Ser |
| | 4025 | | | | | 4030 | | | | 4035 | |
| Ser | Pro | Gly | Lys | Ser | Gln | Gly | Leu | Asn | Leu | His | Thr | Leu | Leu | Tyr |
| | 4040 | | | | | 4045 | | | | 4050 | |
| Leu | Gly | Gly | Val | Glu | Pro | Ser | Val | Pro | Leu | Ser | Pro | Ala | Thr | Asn |
| | 4055 | | | | | 4060 | | | | 4065 | |
| Met | Ser | Ala | His | Phe | Arg | Gly | Cys | Val | Gly | Glu | Val | Ser | Val | Asn |
| | 4070 | | | | | 4075 | | | | 4080 | |
| Gly | Lys | Arg | Leu | Asp | Leu | Thr | Tyr | Ser | Phe | Leu | Gly | Ser | Gln | Gly |
| | 4085 | | | | | 4090 | | | | 4095 | |
| Ile | Gly | Gln | Cys | Tyr | Asp | Ser | Ser | Pro | Cys | Glu | Arg | Gln | Pro | Cys |
| | 4100 | | | | | 4105 | | | | 4110 | |
| Gln | His | Gly | Ala | Thr | Cys | Met | Pro | Ala | Gly | Glu | Tyr | Glu | Phe | Gln |
| | 4115 | | | | | 4120 | | | | 4125 | |
| Cys | Leu | Cys | Arg | Asp | Gly | Phe | Lys | Gly | Asp | Leu | Cys | Glu | His | Glu |
| | 4130 | | | | | 4135 | | | | 4140 | |
| Glu | Asn | Pro | Cys | Gln | Leu | Arg | Glu | Pro | Cys | Leu | His | Gly | Gly | Thr |
| | 4145 | | | | | 4150 | | | | 4155 | |
| Cys | Gln | Gly | Thr | Arg | Cys | Leu | Cys | Leu | Pro | Gly | Phe | Ser | Gly | Pro |
| | 4160 | | | | | 4165 | | | | 4170 | |
| Arg | Cys | Gln | Gln | Gly | Ser | Gly | His | Gly | Ile | Ala | Glu | Ser | Asp | Trp |
| | 4175 | | | | | 4180 | | | | 4185 | |
| His | Leu | Glu | Gly | Ser | Gly | Gly | Asn | Asp | Ala | Pro | Gly | Gln | Tyr | Gly |
| | 4190 | | | | | 4195 | | | | 4200 | |
| Ala | Tyr | Phe | His | Asp | Asp | Gly | Phe | Leu | Ala | Phe | Pro | Gly | His | Val |
| | 4205 | | | | | 4210 | | | | 4215 | |
| Phe | Ser | Arg | Ser | Leu | Pro | Glu | Val | Pro | Glu | Thr | Ile | Glu | Leu | Glu |
| | 4220 | | | | | 4225 | | | | 4230 | |
| Val | Arg | Thr | Ser | Thr | Ala | Ser | Gly | Leu | Leu | Leu | Trp | Gln | Gly | Val |
| | 4235 | | | | | 4240 | | | | 4245 | |
| Glu | Val | Gly | Glu | Ala | Gly | Gln | Gly | Lys | Asp | Phe | Ile | Ser | Leu | Gly |
| | 4250 | | | | | 4255 | | | | 4260 | |
| Leu | Gln | Asp | Gly | His | Leu | Val | Phe | Arg | Tyr | Gln | Leu | Gly | Ser | Gly |
| | 4265 | | | | | 4270 | | | | 4275 | |
| Glu | Ala | Arg | Leu | Val | Ser | Glu | Asp | Pro | Ile | Asn | Asp | Gly | Glu | Trp |
| | 4280 | | | | | 4285 | | | | 4290 | |
| His | Arg | Val | Thr | Ala | Leu | Arg | Glu | Gly | Arg | Arg | Gly | Ser | Ile | Gln |
| | 4295 | | | | | 4300 | | | | 4305 | |
| Val | Asp | Gly | Glu | Glu | Leu | Val | Ser | Gly | Arg | Ser | Pro | Gly | Pro | Asn |
| | 4310 | | | | | 4315 | | | | 4320 | |
| Val | Ala | Val | Asn | Ala | Lys | Gly | Ser | Val | Tyr | Ile | Gly | Gly | Ala | Pro |
| | 4325 | | | | | 4330 | | | | 4335 | |
| Asp | Val | Ala | Thr | Leu | Thr | Gly | Gly | Arg | Phe | Ser | Ser | Gly | Ile | Thr |
| | 4340 | | | | | 4345 | | | | 4350 | |
| Gly | Cys | Val | Lys | Asn | Leu | Val | Leu | His | Ser | Ala | Arg | Pro | Gly | Ala |

```
                  4355                4360                4365
Pro  Pro   Pro Gln Pro Leu Asp   Leu Gln His Arg Ala   Gln Ala Gly
         4370                4375                4380

Ala Asn  Thr Arg Pro Cys Pro  Ser
    4385                4390

<210> SEQ ID NO 22
<211> LENGTH: 35
<212> TYPE: DNA
<213> ORGANISM: Artificial Sequence
<220> FEATURE:
<223> OTHER INFORMATION: forward amplification primer for human
      serglycin

<400> SEQUENCE: 22
atggatccac catgatgcag aagctactca aatgc                              35

<210> SEQ ID NO 23
<211> LENGTH: 36
<212> TYPE: DNA
<213> ORGANISM: Artificial Sequence
<220> FEATURE:
<223> OTHER INFORMATION: reverse amplification primer for human
      serglycin

<400> SEQUENCE: 23
atgaattcta acataaaatc ctcttctaat ccatgt                             36
```

METHOD FOR PRODUCTION OF HEPARIN AND HEPARAN SULFATE

CROSS-REFERENCE TO RELATED APPLICATIONS

This application is a national stage under 35 U.S.C. 371 of International Application PCT/AU2016/050301, filed on Apr. 28, 2016 (currently published). International Application PCT/AU2016/050301 cites the priority of Australian Patent Application No. 2015901556, filed Apr. 30, 2015 (expired) and Australian Patent Application No. 2015904325, filed Oct. 21, 2015 (expired).

TECHNICAL FIELD

The present invention relates to a method of producing a proteoglycan having anticoagulant activity, to a method of producing heparin and/or heparan sulfate, and to proteoglycans and heparin and/or heparan sulfate made by the method. The present invention also relates to a method of using the proteoglycans and heparin and/or heparan sulfate having anticoagulant activity.

BACKGROUND

Heparin is widely used as an anticoagulant. Heparin is used in an injectable form to prevent or treat blood coagulation in patients suffering from, or at risk of suffering from, blood clots. Heparin is also used to form an anticoagulant surface on various experimental and medical devices such as, for example, renal dialysis machines.

Heparin is a polysaccharide which is one of four main subgroups of glycosaminoglycans (GAGs). GAGs are long polysaccharides that are made up of repeating disaccharide units. Within the GAG family there are four main subgroups: (1) hyaluronic acid or hyaluronan (HA); (2) keratan sulfate (KS); (3) chondroitin/dermatan sulfate (CS/DS); and 4) heparan sulfate (HS)/heparin. These subfamilies differ in monosaccharide components, glycosyl linkages, and position and degree of saccharide functionalization. With the exception of HA, GAGs are found covalently attached to a protein core and together are known as proteoglycans.

HS and heparin comprise the disaccharide units $\alpha(1\rightarrow4)$ linked D-glucosamine (GlcN) and $(1\rightarrow4)$ linked uronic acid which is either $\alpha$-linkage L-iduronic acid (IdoA) or $\beta$-linkage D-glucuronic acid (GlcA). Heparin and HS are heterogeneous in nature not only due to differing disaccharide combinations but also their sulfate modifications. Possible modifications include 2-O-sulfation of uronic acid, and N-sulfation, N-acetylation, 3-O- and 6-O-sulfation of glucosamine.

Almost every mammalian cell produces GAGs which are incorporated into proteoglycans in a cell-associated glycocalyx that populates the extracellular matrix (ECM) to define tissue form and function. HS has been shown to modulate cell growth and development by regulating growth factors such as the fibroblast growth factor (FGF) family, platelet derived growth factor (PDGF), and vascular endothelial cell growth factor (VEGF). Heparin, however, is produced predominantly in mast cells.

GAG synthesis requires the precise and timed activity of many enzymes that are involved in GAG chain elongation, epimerisation of the glucuronic acid moiety and modification by sulfates at distinct sites in the chain, a process that is not template-driven and thus results in chain heterogeneity.

The initial product in the biosynthesis of HS and heparin is polysaccharide composed of alternating glucuronic acid (GlcUA) and N-acetylglucosamine (GlcNAc) residues which is covalently bonded to a protein core via a linkage tetrasaccharide covalently bonded to the protein via an oxygen moiety at a serine residue. The serine residue is part of a GAG attachment sequence. The attached polysaccharide is then modified by enzymes in the cell to form complex sulfated derivatives.

The first step in the synthesis of the HS and heparin chain is the formation of a linkage tetrasaccharide which is initiated by the coupling of a xylose to the serine residue of an attachment sequence via the action of xylosyltransferase (XylT), followed by the addition of two galactose molecules in sequence by galactosyltransferases (GalT) 1 and 2, respectively. The tetrasaccharide structure, which is also common to CS chains, is completed by the addition of GlcA by glucuronic acid transferase (GlcAT) 1. It is at this point in GAG biosynthesis that the HS/heparin biosynthetic pathway diverges from the CS/dermatan sulfate (DS) pathway by the addition of an N-acetylglucosamine (GlcNAc) instead of a N-acetyl galactosamine (GalNAc), though the exact mechanisms responsible in controlling this switch between the major GAG types is unknown.

The enzymes that are responsible for the addition of the GlcNAc to the non-reducing end of the linkage tetrasaccharide are known as the EXTL family of glycosyltransferases. The polymerization or elongation of the HS/heparin chains involves a complex being formed between EXT1 and EXT2 that sequentially add a GlcA followed by a GlcNAc moiety and this gives rise to the characteristic alternating copolymer of these two monosaccharides seen in all HS and heparin chains. The sulfation of HS/heparin is started when the acetyl group on some GlcNAc residues is removed and sulfated by one of the four isoforms of the N-deactylase N-sulfotransferase (NDST) enzymes. NDST2 has been shown to have specificity for modifying the GAG chains decorating serglycin making it a critical enzyme in the process of synthesizing mast cell heparin. After this sulfation step, further modification of the HS/heparin chains happens in close proximity to these regions leading to relatively highly sulfated domains or S domains. Most forms of HS contain approximately 30% of their sequence decorated with sulfate leaving approximately 70% as undecorated GlcA-GlcNAc sequences whereas heparin contains long stretches of highly sulfated disaccharides. Once the N-sulfate modification has taken place, some of the GlcA residues in these regions become epimerized to iduronic acid (IdoA) followed by the vast majority being sulfated at the C2 position. The glucuronyl C5-epimerase and hexuronyl 2 sulfotransferase enzymes both have only a single isomer and co-localize in the Golgi, and they have been shown to interact with each other as well as the interaction between C5-epimerase and 6-O-sulfotransferase. Sulfate groups can be added to the C6 position of either GlcNAc or GlcNS by one of three isoforms of the 6-O-sulfotransferase enzymes. These enzymes can act on both GlcNAc and GlcNS but have been shown to have a preference for modifying regions where there is a higher proportion of GlcNS flanked by 2 sulfate modification residues, which supports the synthesis of longer S domains.

The complexity of GAG synthesis, and the lack of information in relation to the conditions which influence attachment of GAG chains to the protein core, presents a challenge for the production of proteoglycans with heparin or HS chains.

Pharmaceutical-grade heparin is still derived from animal tissues such as porcine (pig) intestines or bovine (cattle) lungs. However, heparin obtained from these sources has been associated with some adverse events due to doping with oversulfated chondroitin sulfate (Guerrini et al. Nat. Biotechnol. 2008, 26, 669-675). In addition, isolation of heparin from animal tissue runs the risk of transmission from animals to humans of disease agents such as, for example, viruses, bacteria and TSE. Alternative methods of producing heparin such as chemical or chemo-enzymatic synthesis can produce well-defined structures but are yet to produce the heterogeneous population of structures present in animal-derived heparin.

What are needed are alternative methods for production of heparin and HS. The present disclosure provide novel methods for the production of heparin and/or HS that address the shortcomings of the prior art.

SUMMARY

A first aspect provides a method of producing a proteoglycan having anticoagulant activity, comprising
(a) providing a cell comprising a recombinant nucleic acid encoding a core protein having one or more glycosaminoglycan attachment sites; and
(b) incubating the cell under conditions to promote the production of a proteoglycan comprising the core protein linked to heparin and/or HS and optionally other glycosaminoglycan chains.

A second aspect provides a method of producing a proteoglycan having anticoagulant activity, the method comprising:
(a) providing a cell comprising a recombinant nucleic acid encoding a core protein having one or more glycosaminoglycan attachment sites; and
(b) incubating the cell in medium under conditions which permit expression of the core protein, wherein the medium comprises glucose at a concentration which promotes production of a proteoglycan comprising the core protein linked to heparin and/or HS and optionally other glycosaminoglycan chains.

A third aspect provides a method of producing a proteoglycan having anticoagulant activity, the method comprising:
(a) providing a cell comprising a recombinant nucleic acid encoding a core protein having one or more glycosaminoglycan attachment sites; and
(b) incubating the cell in medium under conditions which permit expression of the core protein, wherein the medium comprises:
  (i) glucose;
  (ii) glucose and sulfate;
  (iii) glucose and phosphate; or
  (iv) glucose, sulfate and phosphate,
at a concentration which promotes production of a proteoglycan comprising the core protein linked to heparin and/or HS and optionally other glycosaminoglycan chains.

A fourth aspect provides a method of producing a proteoglycan having anticoagulant activity, comprising:
(a) providing a cell comprising a recombinant nucleic acid encoding a core protein comprising serglycin, or a fragment thereof, and a glycosaminoglycan attachment site;
(b) incubating the cell under conditions to promote the production of a proteoglycan comprising the core protein linked to heparin and/or HS and optionally other glycosaminoglycan chains.

A fifth aspect provides a method of producing a proteoglycan having anticoagulant activity, comprising:
(a) providing a cell comprising a recombinant nucleic acid encoding a core protein comprising serglycin, or a fragment thereof, and a glycosaminoglycan attachment site;
(b) incubating the host cell in medium under conditions which permit expression of the core protein, or fragment thereof, wherein the medium comprises glucose at a concentration which promotes production of proteoglycan comprising the core protein linked to heparin and/or HS and optionally other glycosaminoglycan chains.

A sixth aspect provides a method of producing a proteoglycan having anticoagulant activity, comprising:
(a) providing a cell comprising a recombinant nucleic acid encoding a core protein comprising serglycin, or a fragment thereof, and a glycosaminoglycan attachment site;
(c) incubating the host cell in medium under conditions which permit expression of the core protein, or fragment thereof, wherein the medium comprises:
  (i) glucose;
  (ii) glucose and sulfate;
  (iii) glucose and phosphate; or
  (iv) glucose, sulfate and phosphate,
at a concentration which promotes production of a proteoglycan comprising the core protein linked to heparin and/or HS and optionally other glycosaminoglycan chains.

A seventh aspect provides a method of producing heparin and/or HS (HS), comprising:
(a) providing a cell comprising a recombinant nucleic acid encoding a core protein having one or more glycosaminoglycan attachment sites;
(b) incubating the cell under conditions to promote production of a proteoglycan comprising the core protein linked to heparin and/or HS and optionally other glycosaminoglycan chains; and
(c) isolating the heparin and/or HS.

An eighth aspect provides a method of producing heparin and/or HS, the method comprising:
(a) providing a cell comprising a recombinant nucleic acid encoding a core protein having one or more glycosaminoglycan attachment sites;
(b) incubating the cell in medium under conditions which permit expression of the core protein, wherein the medium comprises glucose at a concentration which promotes production of a proteoglycan comprising the core protein linked to heparin and/or HS and optionally other glycosaminoglycan chains; and
(c) isolating the heparin and/or HS.

A ninth aspect provides a method of producing heparin and/or HS, the method comprising:
(a) providing a cell comprising a recombinant nucleic acid encoding a core protein having one or more glycosaminoglycan attachment sites;
(b) incubating the cell in medium under conditions which permit expression of the core protein, wherein the medium comprises:
  (i) glucose;
  (ii) glucose and sulfate;
  (iii) glucose and phosphate; or
  (iv) glucose, sulfate and phosphate,
at a concentration which promotes production of a proteoglycan comprising the core protein linked to heparin and/or HS and optionally other glycosaminoglycan chains; and (c) isolating the heparin and/or HS.

A tenth aspect provides a method of producing heparin and/or HS, comprising:
- (a) providing a cell comprising a recombinant nucleic acid encoding a core protein comprising serglycin, or a fragment thereof, and a glycosaminoglycan attachment site;
- (b) incubating the cell under conditions to promote production of a proteoglycan comprising the core protein linked to heparin and/or HS and optionally other glycosaminoglycan chains; and
- (c) isolating the heparin and/or HS.

An eleventh aspect provides a method of producing heparin and/or HS having anticoagulant activity, comprising:
- (a) providing a cell comprising a recombinant nucleic acid encoding a core protein comprising serglycin, or a fragment thereof, and a glycosaminoglycan attachment site;
- (b) incubating the cell in medium under conditions which permit expression of the core protein, or fragment thereof, wherein the medium comprises glucose at a concentration which promotes production of proteoglycan comprising the core protein linked to heparin and/or HS and optionally other glycosaminoglycan chains; and
- (c) isolating the heparin and/or HS.

A twelfth aspect provides a method of producing heparin and/or HS having anticoagulant activity, comprising:
- (a) providing a cell comprising a recombinant nucleic acid encoding a core protein comprising serglycin, or a fragment thereof, and a glycosaminoglycan attachment site;
- (b) incubating the cell in medium under conditions which permit expression of the core protein, wherein the medium comprises:
  - (i) glucose;
  - (ii) glucose and sulfate;
  - (iii) glucose and phosphate; or
  - (iv) glucose, sulfate and phosphate,
  at a concentration which promotes production of a proteoglycan comprising the core protein linked to heparin and/or HS and optionally other glycosaminoglycan chains; and
- (c) isolating the heparin and/or HS.

A thirteenth aspect provides a proteoglycan produced by the method of the first to sixth aspect.

A fourteenth aspect provides heparin and/or HS produced by the method of the seventh to twelfth aspect.

A fifteenth aspect provides a cell comprising a recombinant nucleic acid encoding a core protein comprising a glycosaminoglycan attachment site, wherein the cell is capable of producing a proteoglycan comprising the core protein linked to heparin and/or HS and optionally other glycosaminoglycan chains.

A sixteenth aspect provides a cell comprising a recombinant nucleic acid encoding a core protein comprising serglycin, or a fragment thereof, and a glycosaminoglycan attachment site, wherein the cell is capable of producing a proteoglycan comprising the core protein linked to heparin and/or HS and optionally other glycosaminoglycan chains.

A seventeenth aspect provides a recombinant proteoglycan comprising a core protein linked to heparin and/or HS and optionally other glycosaminoglycan chains.

An eighteenth aspect provides a recombinant proteoglycan comprising serglycin, or a fragment thereof, linked to heparin and/or HS and optionally other glycosaminoglycan chains.

A nineteenth aspect provides a method of treating or preventing blood coagulation, comprising contacting the blood with an effective amount of the proteoglycan of the thirteenth, seventeenth or eighteenth aspect, or heparin and/or HS of the fourteenth aspect.

A twentieth aspect provides a method of treating or preventing blood coagulation, or a condition associated with blood coagulation, in a subject in need thereof, comprising administering an effective amount of the proteoglycan of the thirteenth, seventeenth or eighteenth aspect, or heparin and/or HS of the fourteenth aspect.

A twenty-first aspect provide a proteoglycan of the thirteenth, seventeenth or eighteenth aspect, or heparin and/or HS of the fourteenth aspect, for use in treating or preventing blood coagulation, or a condition associated with blood coagulation, in a subject in need thereof, or the use of a proteoglycan of the thirteenth, seventeenth or eighteenth aspect, or heparin and/or HS of the fourteenth aspect in the manufacture of a medicament for treating or preventing blood coagulation, or a condition associated with blood coagulation, in a subject in need thereof.

BRIEF DESCRIPTION OF THE FIGURES

FIG. 7 is a graph showing the ratio of absorbance for HS (clone 10E4) and CS (clone CS-56) to serglycin protein core as determined by ELISA. Data are presented as mean±S.D. (error bars) (n=3). * indicated significant differences ($p<0.05$) compared to 25 mM glucose analyzed by one-way ANOVA.

DETAILED DESCRIPTION

Figure 1:
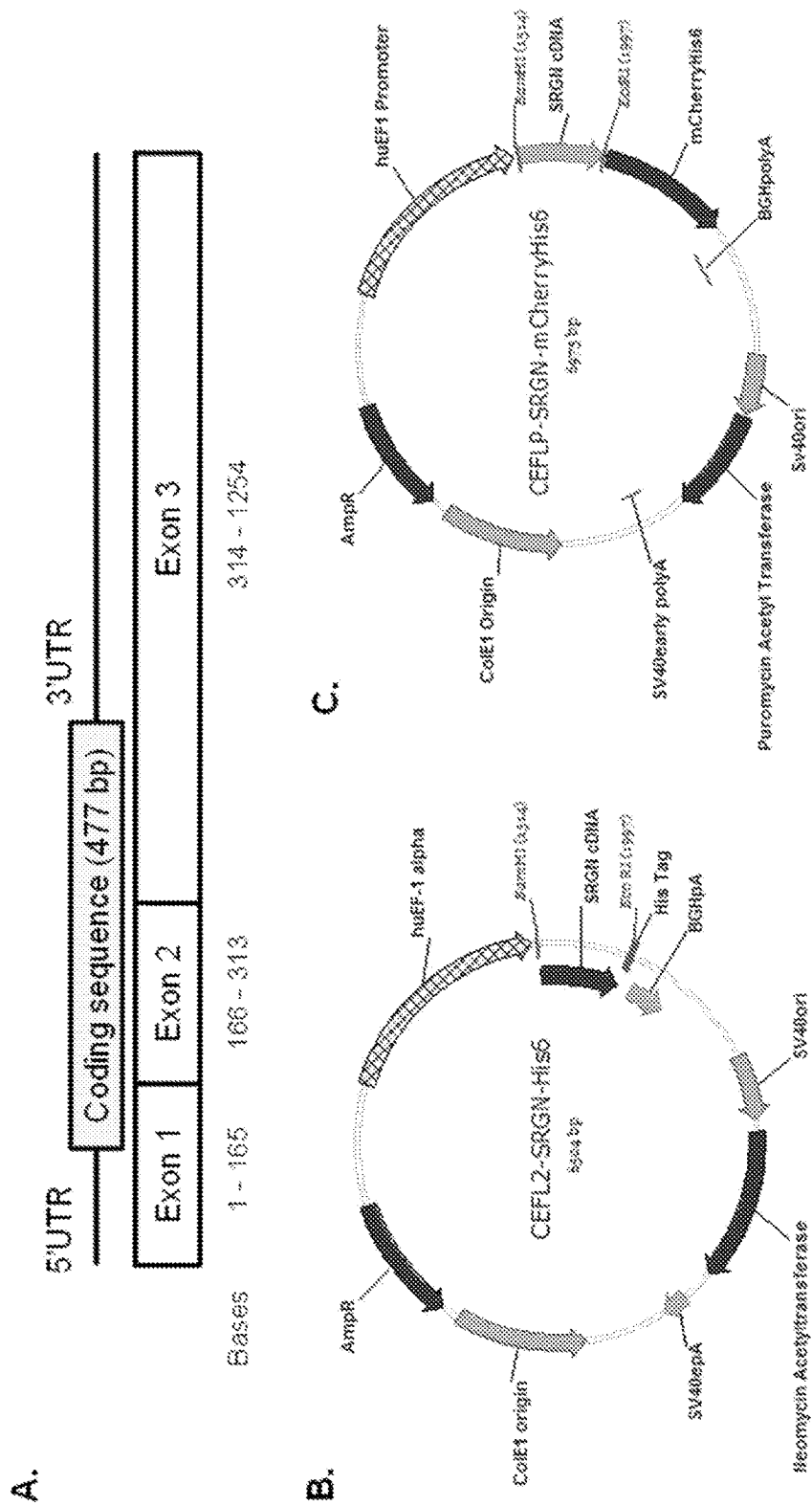
FIG. 1A shows a schematic representation of the serglycin gene encoded by 3 exons, of which the coding sequence (bases 87-563) encodes for the signal and mature peptides and spans regions of exons 1 and 3 and the entire exon 2.
FIG. 1B shows CEFL2-SRGN, an exemplary embodiment of a vector used to express serglycin (SRGN)
FIG. 1C shows CEFLP-SRGN, an exemplary embodiment of a vector used to express SRGN.

The present disclosure relates in one aspect to methods of production of a proteoglycan having anticoagulant activity by expressing a recombinant proteoglycan comprising a core protein linked to heparin and/or HS and optionally other GAG chains. The present disclosure provides various methods for such production.

In one embodiment of this aspect, the method of producing a proteoglycan having anticoagulant activity, comprises: (a) providing a cell comprising a nucleic acid, including a recombinant nucleic acid, encoding a core protein having one or more GAG attachment sites; and (b) incubating the cell under conditions to promote the production of a proteoglycan comprising the core protein linked to heparin and/or HS and optionally other GAG chains.

In certain embodiments, the cells are incubated in a medium under conditions which permit expression of the core protein, wherein the medium comprises glucose at a concentration which promotes production of a proteoglycan comprising the core protein linked to heparin and/or HS and optionally other GAG chains.

In certain embodiments, the cells are incubated in a medium under conditions which permit expression of the core protein, wherein the medium comprises: (i) glucose; (ii) glucose and sulfate; (iii) glucose and phosphate; or (iv) glucose, sulfate and phosphate, at a concentration(s) which promotes production of a proteoglycan comprising the core protein linked to heparin and/or HS and optionally other GAG chains.

In certain embodiments, the heparin and/or HS is the predominant GAG chain linked to the core protein. For example, the heparin and/or HS may make up 80% of the total amount of all GAG chains present on the core protein.

In another embodiment of this aspect, the method of producing a proteoglycan having anticoagulant activity, comprises: (a) providing a cell comprising a nucleic acid, including a recombinant nucleic acid, encoding a core protein comprising serglycin, or a fragment thereof, and a GAG attachment site; and (b) incubating the cell under conditions to promote the production of a proteoglycan comprising the core protein linked to heparin and/or HS and optionally other GAG chains.

In certain embodiments, the cells are incubated in a medium under conditions which permit expression of the core protein, wherein the medium comprises glucose at a concentration which promotes production of a proteoglycan comprising the core protein linked to heparin and/or HS and optionally other GAG chains.

In certain embodiments, the cells are incubated in a medium under conditions which permit expression of the core protein, wherein the medium comprises: (i) glucose; (ii) glucose and sulfate; (iii) glucose and phosphate; or (iv) glucose, sulfate and phosphate, at a concentration(s) which promotes production of a proteoglycan comprising the core protein linked to heparin and/or HS and optionally other GAG chains.

In certain embodiments, the heparin and/or HS is the predominant GAG chain linked to the core protein. For example, the heparin and/or HS may make up 80% of the total amount of all GAG chains present on the core protein.

HS may also be known in the art as heparin sulfate. As used herein, a "proteoglycan" is a molecule comprising a core protein to which is linked, typically covalently linked, one or more GAGs. When more than one GAG is linked to the core protein, the GAGs may be the same, or they may be different GAGs. As used herein, a "core protein" is a protein to which one or more GAG may be attached and which contains one or more attachment sites for a GAG and optionally other functional domains, including, but not limited to, a signal sequence and an affinity tag. As used herein, a "recombinant proteoglycan" is a proteoglycan in which the protein/polypeptide portion of the proteoglycan (for example, the core protein) is produced by a recombinant nucleic acid. As used herein, a "recombinant nucleic acid" is a nucleic acid prepared using recombinant DNA techniques. A "proteoglycan having anticoagulant activity" is a proteoglycan which prevents, at least to some extent, the coagulation of blood. The anticoagulant activity of the proteoglycan may be determined by any methods known in the art for determining the activity of heparin, such as, for example, through measuring the activated partial thromboplastin time assay (aPTT assay), which is the time it takes blood plasma to clot, or assays which measure the inhibitory action of heparin on isolated coagulation enzymes such as Factor Xa and thrombin. In a preferred embodiment, the anticoagulant activity of the proteoglycan is determined using the aPTT assay as described in Example 3.

It will be appreciated that the proteoglycan(s) of the present disclosure will typically have anticoagulant activity that is a fraction of the activity of a pharmaceutical heparin. In various embodiments, the proteoglycan has anticoagulant activity in the range of from, 1/50 to 1/1, 1/50 to 3/4, 1/50 to 1/2, 1/40 to 1/3, 1/40 to 1/5, 1/30 to 1/10, 1/25 to 1/10, 1/25 to 1/15, 1/30 to 1/15, 1/30 to 1/10, 1/30 to 1/5, of the activity of pharmaceutical grade heparin.

The methods above generally comprise providing a cell (which may also be referred to as a host cell) capable of synthesizing heparin and/or HS. As used herein, a "cell that is capable of synthesizing heparin and/or HS" is a cell that expresses, or is capable of expressing, the enzymes necessary to produce heparin and/or HS. The enzymes necessary to produce heparin and/or HS includes the enzymes necessary for: synthesis of heparin and/or HS GAG polymer; synthesis of the linkage tetrasaccharide (e.g. xyl-Gal-Gal-GlcA) which links the heparin/HS molecule to the core protein; and sulphation of the GAG polymer. Thus, a cell that is capable of synthesizing heparin and/or HS will typically comprise the transferases for synthesis of the linkage tetrasaccharide, the transferases for synthesis of the disaccharide polymer which forms the polysaccharide structure of heparin and HS, and the enzymes for modification of the heparin and/or HS polysaccharide structure (e.g. sulphation). A cell capable of synthesizing heparin will also be capable of synthesizing HS.

In another embodiment, the cell capable of synthesizing heparin and/or HS will also be capable of synthesizing a polypeptide (such as a core protein encoded by a nucleic acid), optionally synthesizing other GAGs and synthesizing proteoglycans by linking the heparin and/or HS, an optionally other GAGs, to the polypeptide.

Typically, the cell is a mammalian cell. More typically, the cell is a human cell.

Mammalian cells suitable for use as cells include cells such as, for example, human umbilical vein endothelial cells (HUVEC), human umbilical artery endothelial cells (HUAEC), human lung microvascular endothelial cells (HLMVEC), Human Aortic Endothelial Cells (HAoEC), Human Coronary Artery Endothelial Cells (HCAEC), Human Pulmonary Artery Endothelial Cells (HPAEC), human embryonic kidney (HEK), and other human derived cell lines. Mammalian cells lines suitable for use as host cells include HEK293 cells and derivatives thereof, and CHO cells. In a particular embodiment, the cell is an HEK293 cell or derivative thereof.

The methods described above comprise providing a cell capable of synthesizing heparin and/or HS comprising a nucleic acid, including a recombinant nucleic acid, encoding a core protein having one or more GAG attachment sites or a nucleic acid, including a recombinant nucleic acid, encoding a core protein comprising a fragment of a proteoglycan (for example, serglycin) having one or more GAG attachment site. In one embodiment, the cell capable of synthesizing heparin and/or HS is provided by introducing into a the cell a nucleic acid, including a recombinant nucleic acid, encoding a core protein having one or more GAG attachment sites or a recombinant nucleic acid encoding a core protein comprising a fragment of a proteoglycan (for example, serglycin) having one or more GAG attachment site. As used herein, "introducing into the cell", means facilitating uptake or absorption into the cell, as is understood by those skilled in the art. Typically, the nucleic acid or recombinant nucleic acid is introduced into the host cell by transforming or transfecting the host cell with the nucleic acid or recombinant nucleic acid. Methods for introducing nucleic acid into cells, and in particular, methods for introducing nucleic acid into mammalian cells, are well known in the art, and are described in, for example, Sambrook et al. (Cold Spring Harbor Laboratory, 3rd edition (2001); Cell Biology (Third Edition) A Laboratory Handbook, 2006, Elsevier Inc.).

The nucleic acid introduced into the cells encodes a core protein having one or more GAG attachment sites, such as for example, a core protein comprising serglycin, or a fragment thereof, and one or more GAG attachment site. As used herein, the phrase "a core protein comprising a proteoglycan, or a fragment thereof" means the core protein comprises the amino acid sequence of such proteoglycan, or a fragment of such amino acid sequence. As used herein, a "GAG attachment site" is an amino acid residue to which a GAG can be attached. Typically, the GAG attachment site is an amino acid residue to which a linkage tetrasaccharide is attached. The tetrasaccharide is then extended by synthesis of the heparin or HS polysaccharide (or other GAGs). Typically, the GAG attachment site is a serine residue. More typically, the GAG attachment site is a serine residue in a sequence comprising ser-gly (S-G), ser-gly-asp (S-G-D) or ser-gly-glu (S-G-E). Still more typically, the GAG attachment site is a serine residue in a ser-gly repeat sequence. In certain embodiments, the GAG attachment site is a serine residue in a ser-gly repeat sequence, wherein 2 to 30, 2-25, 2-20, 2-10, 5-25, 5-20, 10-20, 2-8, 24, or 10 ser-gly repeat sequences are present. The ser-gly repeat sequences may be contiguous or may be noncontiguous in that one or more amino acids appear in between one or more ser-gly sequences.

Examples of sequences comprising GAG attachment sites include the following:

| Sequence A | $(SG)_x(Xaa)_y(SG)_z$ | SEQ ID NO: 9 |
|---|---|---|
| Sequence B | $(SG)_z$ | |
| Sequence C | SGD | |
| Sequence D | $SGD(Xaa)_{y1}SGD(XAA)_{y2}SGD$ | SEQ ID NO: 11 |
| Sequence E | $(SG)_2FG(SG)_6$ (human serglycin) | SEQ ID NO: 1 |
| Sequence F | $(SG)_{24}$ (rat serglycin) | SEQ ID NO: 12 |
| Sequence G | $(SG)_{10}$ (mouse serglycin) | SEQ ID NO: 13 |
| Sequence H | SGDDLGSGDLGSGD (human perlecan) | SEQ ID NO: 14 |
| Sequence I | SGE (human perlecan) | |
| Sequence J | SGDGLGSGDVGSGD (mouse perlecan) | SEQ ID NO: 15 |
| Sequence K | SGSG | SEQ ID NO: 10 |
| Sequence L | $(SG)_2(Xaa)_2(SG)_6$ | SEQ ID NO: 9 |
| Sequence M | $SGD(Xaa)_3SGD(Xaa)_2SGD$ | SEQ ID NO: 11 |

For Sequence A, x is 1-15, such as 2-13, 2-10, 2-6 or 2, z is 1-30, such as 4-25, 6-20, 8-25, 10-20, 6-10, or 6 and y is 1-10, such as, 1-5 or 2 and the sum of x and z is from 2-30, 2-20, 2-10, 5-25, 5-20, 10-20, 2-8, 24, or 10.

For Sequence B, z is 1-30, such as 4-25, 6-20, 8-25, 10-20, 6-10, 10 or 24.

For Sequence D, y1 is 1 to 10, such as, 1-5 or 3 and y2 is 1 to 10, such as, 1-5 or 2.

The core protein may comprise one or more GAG attachment sites. Typically, the core protein comprises multiple GAG attachment sites.

In another embodiment, the nucleic acid, including a recombinant nucleic acid, introduced into the cells encodes a core protein having one or more GAG attachment sites and optionally at least one functional domain. Such functional domains include, but are not limited to, a signal sequence and an affinity tag. When a signal sequence is encoded, any signal sequence known in the art may be used, particularly signal sequences associated with a proteoglycan. Such signal sequence may be obtained from a HS proteoglycan. The signal sequence is typically positioned upstream from the GAG attachment sites. In certain aspects, the signal sequence and the core protein are from the same proteoglycan (for example, if the core protein is human serglycin, the signal sequence is from serglycin). In certain aspects, the signal sequence and the core protein are from a different proteoglycan (for example, if the core protein is human serglycin, the signal sequence is not from serglycin).

Representative signal sequences are shown below.

```
Human serglycin
                                          (SEQ ID NO: 16)
MMQKLLKCSR LVLALALILV LESSVQG Rat serglycin
                                          (SEQ ID NO: 17)
MRQVPVGTRL VLALAFVLVW GSSVQG Mouse serglycin
                                          (SEQ ID NO: 18)
MQVPVGSRLV LALAFVLVWG SSVQG Human perlecan
                                          (SEQ ID NO: 19)
MGWRAPGALL LALLLHGRLL AV HUMAN SECRETED PROTEIN ACIDIC AND RICH IN
CYSTEIN (SPARC)
                                          (SEQ ID NO: 20)
MRAWIFFLLC LAGRALA
```

In certain aspects, the sequence of the core protein, all or a portion of the at least one GAG attachment sites and the signal sequence, when present, are from the same proteoglycan (for example, if the core protein is human serglycin or a fragment thereof, all or a portion of the at least one GAG attachment sites and the signal sequence is from serglycin). In certain aspects, the sequence of the core protein, all or a portion of the at least one GAG attachment sites and the signal sequence, when present, are from a different proteoglycan (for example, if the core protein is human serglycin or a fragment thereof, all or a portion of the at least one GAG attachment sites and/or the signal sequence is not from serglycin).

When an affinity tag is encoded by the nucleic acid, any affinity tag known in the art may be used. Exemplary affinity tags are provided herein. Typically the affinity tag is position downstream of the nucleic acid portion encoding the proteoglycan portion and/or the GAG attachment sites. In certain embodiments, the affinity tag may be cleaved from the produced polypeptide after expression.

Nucleic Acids for Use in the Present Disclosure.

The nucleic acid, including a recombinant nucleic acid, encoding the core protein may vary depending on the nature of the core protein, the nature of the GAG attachment site, and the nature of the optional functional domains, among other things. At a minimum, the nucleic acid encoding the core protein comprises a sequence encoding a polypeptide comprising one or more GAG attachment sites.

In one embodiment, the nucleic acid encoding the core protein comprises a sequence encoding a proteoglycan comprising one or more GAG attachment sites, or a fragment of a proteoglycan comprising one or more GAG attachment sites. In another embodiment, the nucleic acid encoding the core protein comprises a sequence encoding a HS proteoglycan comprising one or more GAG attachment sites, or a fragment of a HS proteoglycan comprising one or more GAG attachment sites. Such nucleic acid encoding the core protein may further comprise a sequence encoding at least one of a signal sequence and an affinity tag.

In one embodiment, the core protein encoded by the nucleic acid is serglycin, or a fragment of serglycin.

In this regard, human serglycin comprises up to 8 GAG attachment sites in the sequence SGSGFGSGSGSGSGSGSG (SEQ ID NO: 1). Accordingly, in one embodiment, the core protein comprises the amino acid sequence SGSGFGSGSGSGSGSGSG (SEQ ID NO: 1). In one embodiment, the core protein comprises the mature amino acid sequence of human serglycin (SEQ ID NO: 2), or an amino acid sequence that comprises one or more GAG attachment sites and is at least 80%, 85%, 90%, 95%, 99% or 100% identical to the amino acid sequence of SEQ ID NO: 2. In some embodiments, the core protein comprises a signal sequence for secretion of the proteoglycan into the culture medium. Typically, the signal sequence is the signal sequence of serglycin. Thus, in one embodiment, the core protein comprises the amino acid sequence of the signal sequence and the mature protein of human serglycin (SEQ ID NO: 3), or an amino acid sequence that comprises one or more GAG attachment sites and is at least 80%, 85%, 90%, 95%, 99% or 100% identical to the amino acid sequence of SEQ ID NO: 3. It will be appreciate that a signal sequence that is not from serglycin may also be used.

The amino acid sequence of the mature protein of human serglycin is (with GAG attachment sites in bold):

```
                                          (SEQ ID NO: 2)
YPTRRARYQW VRCNPDSNSA NCLEEKGPMF ELLPGESNKI

PRLRTDLFPK TRIQDLNRIF PLSEDYSGSG FGSGSGSGSG

SGSGFLTEME QDYQLVDESD AFHDNLRSLD RNLPSDSQDL

GQHGLEEDFM L
```

The amino acid sequence of the full length protein of human serglycin is (with signal sequence underlined and GAG attachment sites in bold):

```
                                          (SEQ ID NO: 3)
MMQKLLKCSR LVLALALILV LESSVQGYPT RRARYQWVRC

NPDSNSANCL EEKGPMFELL PGESNKIPRL RTDLFPKTRI

QDLNRIFPLS EDYSGSGFGS GSGSGSGSGS GFLTEMEQDY

QLVDESDAFH DNLRSLDRNL PSDSQDLGQH GLEEDFML
```

The nucleotide sequence encoding the full length protein of human serglycin is:

```
                                          (SEQ ID NO: 4)
ATGATGCAGA AGCTACTCAA ATGCAGTCGG CTTGTCCTGG

CTCTTGCCCT CATCCTGGTT CTGGAATCCT CAGTTCAAGG

TTATCCTACG CGGAGAGCCA GGTACCAATG GGTGCGCTGC

AATCCAGACA GTAATTCTGC AAACTGCCTT GAAGAAAAAG

GACCAATGTT CGAACTACTT CCAGGTGAAT CCAACAAGAT

CCCCCGTCTG AGGACTGACC TTTTTCCAAA GACGAGAATC

CAGGACTTGA ATCGTATCTT CCCACTTTCT GAGGACTACT
```

```
-continued
CTGGATCAGG CTTCGGCTCC GGCTCCGGCT CTGGATCAGG

ATCTGGGAGT GGCTTCCTAA CGGAAATGGA ACAGGATTAC

CAACTAGTAG ACGAAAGTGA TGCTTTCCAT GACAACCTTA

GGTCTCTTGA CAGGAATCTG CCCTCAGACA GCCAGGACTT

GGGTCAACAT GGATTAGAAG AGGATTTTAT GTTATAA
```

In one embodiment, the nucleic acid encoding the core protein comprises a sequence encoding a polypeptide having an amino acid sequence of SEQ ID NO: 2, an optional signal sequence and an optional affinity tag. In one embodiment, the nucleic acid encoding the core protein comprises a sequence encoding a polypeptide having an amino acid sequence of SEQ ID NO: 3 and an optional affinity tag.

In one embodiment, the nucleic acid encoding the core protein comprises a sequence encoding a polypeptide having an amino acid sequence comprising a fragment of SEQ ID NO: 2 and one or more GAG attachment sites, an optional signal sequence and an optional affinity tag. In certain aspects, at least one GAG attachment site is contained in the fragment of SEQ ID NO: 2. In certain aspects, the fragment of SEQ ID NO: 2 is from 20 to 50 amino acids in length, from 20 to 40 amino acids in length or from 20 to 30 amino acids in length. In certain aspects, the fragment of SEQ ID NO: 2 comprises amino acids 67 to 84 of SEQ ID NO; 2. In certain aspects, the signal sequence has the sequence of one of SEQ ID NOS: 16 to 20. In certain aspects, the one or more GAG attachment sites have the sequence of one of Sequences A to M above. In certain aspects, the signal sequence has the sequence of SEQ ID NO: 16 and the one or more GAG attachment sites have the sequence of Sequence E (SEQ ID NO: 1).

As used herein, a "fragment of SEQ ID NO: X" refers to a portion of the specified amino acid sequence. In one aspect, the portion is identical to the amino acid sequence of the specified SEQ ID NO. In one aspect, the portion is not identical to the amino acid sequence of the specified SEQ ID NO: and contains one or more deletions, insertions or substitutions with respect to the amino acid sequence of the specified Sequence ID NO. In certain aspects, when a substitution is present, the substitution is a conservative amino acid substitution.

Conservative amino acid substitutions are well-known and may be made generally without altering the biological activity of the resulting protein or polypeptide. For example, such conservative substitutions are generally made by interchanging within the groups of polar residues, charged residues, hydrophobic residues, small residues, and the like. For example, certain amino acids may be substituted for other amino acids in a protein/polypeptide structure without appreciable alteration of the protein/polypeptide structure. In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein/polypeptide, which in part defines the activity of the protein/polypeptide.

Each amino acid has been assigned a hydropathic index on the basis of its hydrophobicity and charge characteristics (Kyte and Doolittle, 1982) as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein/polypeptide with similar structure and/or biological activity. In making such changes, the hydropathic indices of the substituted amino acids are within +/−2, +/−1 or +/−0.5.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of a protein/polypeptide. The following hydrophilicity values have been assigned to amino acid residues: arginine (+3.0); lysine (+3.0); aspartate (+3.0.+−0.1); glutamate (+3.0.+−0.1); serine (.+−.0.3); asparagine (+0.2); glutamine (+0.2) glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still result in a protein/polypeptide with similar structure and/or biological activity. In making such changes, the hydrophilicity values of the substituted amino acids are within +/−2, +/−1 or +/−0.5.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

In the present disclosure, the core protein functions as a scaffold to allow the attachment of certain GAG chains, such as heparin and/or HS. As such the exact structure of the core protein is not as critical, particularly when the GAG attachment sites are not changed. Therefore, the present disclosure contemplates that the various alterations to the amino acid sequence of the core protein may be made without appreciable loss of the ability of the expressed polypeptide to effectively be linked to GAG chains and as such the modifications are within the scope of the disclosure. In one embodiment, the site of GAG attachment is not altered in an amino acid sequence that is at least X % identical to a specified SEQ ID NO: or in a fragment that contains an addition, deletion or substitution with respect to a specified SEQ ID NO.

In one embodiment, the nucleic acid encoding the core protein comprises a sequence encoding a polypeptide having an amino acid sequence that is at least 80%, 85%, 90%, 95% or 99% identical to the amino acid sequence of SEQ ID NOS: 2 or 3, one or more GAG attachment sites, an optional signal sequence and an optional affinity tag. In certain aspects, at least one GAG attachment site is contained in the amino acid sequence that is at least 80%, 85%, 90%, 95% or 99% identical to the amino acid sequence of SEQ ID NOS: 2 or 3. In certain aspects, the signal sequence has the sequence of SEQ ID NOS: 16 to 20. In certain aspects, the one or more GAG attachment sites have the sequence of one of Sequences A to M above. In certain aspects, the signal sequence has the sequence of SEQ ID NO: 16 and the one or more GAG attachment sites have the sequence of Sequence E (SEQ ID NO: 1).

When referring to an amino acid sequence that is at least X % identical to a specified SEQ ID NO, the amino acid sequence may contain, deletions, insertions of substitutions relative to the specified SEQ ID NO. In certain aspects, when a substitution is present, the substitution is one based on the relative similarity of the amino acid side-chain that is substituted as described herein, such as a conservative amino acid substitution.

It will also be appreciated that serglycin from species other than human may be used for the core protein. In some other embodiments, the core protein may comprise:
(a) the mature amino acid sequence of rat serglycin (SEQ ID NO: 5), a fragment thereof comprising one or more GAG attachment sites, or an amino acid sequence that comprises one or more GAG attachment sites and is at least 80%, 85%, 90%, 95%, 99% or 100% identical to the amino acid sequence of mature rat serglycin; or
(b) the mature amino acid sequence of mouse serglycin (SEQ ID NO: 7), a fragment thereof comprising one or more GAG attachment sites, or an amino acid sequence that comprises one or more GAG attachment sites and is at least 80%, 85%, 90%, 95%, 99% or 100% identical to the amino acid sequence of mature mouse serglycin.

The amino acid sequence of the mature protein of rat serglycin is (with GAG attachment sites in bold):

```
                                         (SEQ ID NO: 5)
YPARRARYQW VRCKPDGIFA NCIEEKGPRF DLIAEESNVG

PPMTDPVLMR GFPNDFFPIS DDYSGSGSGS GSGSGSGSGS

GSGSGSGSGS GSGSGSGSGS GSGSGSGSGS GSLADMEWEY

QPTDENNIVY FNYGPFDRML TEQNQEQPGD FII
```

The amino acid sequence of the full length protein of rat serglycin (with signal sequence underlined and GAG attachment sites in bold) is:

```
                                         (SEQ ID NO: 6)
MRQVPVGTRL VLALAFVLVW GSSVQGYPAR RARYQWVRCK

PDGIFANCIE EKGPRFDLIA EESNVGPPMT DPVLMRGFPN

DFFPISDDYS GSGSGSGSGS GSGSGSGSGS GSGSGSGSGS

GSGSGSGSGS GSGSGSGSLA DMEWEYQPTD ENNIVYFNYG

PFDRMLTEQN QEQPGDFII
```

The amino acid sequence of the mature protein of mouse serglycin is (with GAG attachment sites in bold:

```
                                         (SEQ ID NO: 7)
YPARRARYQW VRCKPNGFFA NCIEEKGPQF DLIDESNNIG

PPMNNPVLME GPSKDFISNY DDYGSGSGSG SGSGSGSGSG

SGSGFLGDME WEYQPTDESN IVYFNYKPFD RILTEQNQDQ

PEDDFII
```

The amino acid sequence of the full length protein of mouse serglycin (with signal sequence underlined and GAG attachment sites in bold)) is:

```
                                         (SEQ ID NO: 8)
MQVPVGSRLV LALAFVLVWG SSVQGYPARR ARYQWVRCKP

NGFFANCIEE KGPQFDLIDE SNNIGPPMNN PVLMEGPSKD

FISNYDDYGS GSGSGSGSGS GSGSGSGSGF LGDMEWEYQP

TDESNIVYFN YKPFDRILTE QNQDQPEDDF II
```

In one embodiment, the nucleic acid encoding the core protein comprises a sequence encoding a polypeptide having an amino acid sequence of SEQ ID NO: 5, an optional signal sequence and an optional affinity tag. In one embodiment, the nucleic acid encoding the core protein comprises a sequence encoding a polypeptide having an amino acid sequence of SEQ ID NO: 6, an optional signal sequence and an optional affinity tag.

In one embodiment, the nucleic acid encoding the core protein comprises a sequence encoding a polypeptide having an amino acid sequence comprising a fragment of SEQ ID NO: 5 and one or more GAG attachment sites, an optional signal sequence and an optional affinity tag. In certain aspects, at least one GAG attachment site is contained in the fragment of SEQ ID NO: 5. In certain aspects, the fragment of SEQ ID NO: 5 is from 20 to 80 amino acids in length, from 20 to 60 amino acids in length, from 20 to 40 amino acids in length or from 20 to 30 amino acids in length. In certain aspects, the fragment of SEQ ID NO: 5 comprises amino acids 64 to 111 of SEQ ID NO; 5. In certain aspects, the signal sequence has the sequence of SEQ ID NOS: 16 to 20. In certain aspects, the one or more GAG attachment sites have the sequence of one of Sequences A to M above. In certain aspects, the signal sequence has the sequence of SEQ ID NO: 17 and the one or more GAG attachment sites have the sequence of Sequence F (SEQ ID NO: 12).

In one embodiment, the nucleic acid encoding the core protein comprises a sequence encoding a polypeptide having an amino acid sequence of SEQ ID NO: 7, an optional signal sequence and an optional affinity tag. In one embodiment, the nucleic acid encoding the core protein comprises a sequence encoding a polypeptide having an amino acid sequence of SEQ ID NO: 8, an optional signal sequence and an optional affinity tag.

In one embodiment, the nucleic acid encoding the core protein comprises a sequence encoding a polypeptide having an amino acid sequence comprising a fragment of SEQ ID NO: 7 and one or more GAG attachment sites, an optional signal sequence and an optional affinity tag. In certain aspects, at least one GAG attachment site is contained in the fragment of SEQ ID NO: 7. In certain aspects, the fragment of SEQ ID NO: 7 is from 20 to 80 amino acids in length, from 20 to 60 amino acids in length, from 20 to 40 amino acids in length or from 20 to 30 amino acids in length. In certain aspects, the fragment of SEQ ID NO: 7 comprises amino acids 65 to 84 of SEQ ID NO; 7. In certain aspects, the signal sequence has the sequence of SEQ ID NOS: 16 to 20. In certain aspects, the one or more GAG attachment sites have the sequence of one of Sequences A to M above. In certain aspects, the signal sequence has the sequence of SEQ ID NO: 18 and the one or more GAG attachment sites have the sequence of Sequence G (SEQ ID NO: 13).

In one embodiment, the nucleic acid encoding the core protein comprises a sequence encoding a polypeptide having an amino acid sequence that is at least 80%, 85%, 90%, 95% or 99% identical to the amino acid sequence of SEQ ID NOS: 5, 6, 7 or 8, one or more GAG attachment sites, an optional signal sequence and an optional affinity tag. In certain aspects, at least one GAG attachment site is contained in the amino acid sequence that is at least 80%, 85%, 90%, 95% or 99% identical to the amino acid sequence of SEQ ID NOS: 5, 6, 7 or 8. In certain aspects, the signal sequence has the sequence of SEQ ID NOS: 16 to 20. In certain aspects, the one or more GAG attachment sites have the sequence of one of Sequences A to M above.

In certain aspects, the signal sequence has the sequence of SEQ ID NO: 17 and the one or more GAG attachment sites have the sequence of Sequence F (SEQ ID NO: 12) when the sequence encodes a polypeptide having an amino acid sequence that is at least 80%, 85%, 90%, 95% or 99% identical to the amino acid sequence of SEQ ID NO: 5. In certain aspects, the one or more GAG attachment sites have the sequence of Sequence F (SEQ ID NO: 12) when the sequence encodes a polypeptide having an amino acid sequence that is at least 80%, 85%, 90%, 95% or 99% identical to the amino acid sequence of SEQ ID NO: 6.

In certain aspects, the signal sequence has the sequence of SEQ ID NO: 18 and the one or more GAG attachment sites have the sequence of Sequence G (SEQ ID NO: 13) when the sequence encodes a polypeptide having an amino acid sequence that is at least 80%, 85%, 90%, 95% or 99% identical to the amino acid sequence of SEQ ID NO: 7. In certain aspects, the one or more GAG attachment sites have the sequence of Sequence G (SEQ ID NO: 13) when the sequence encodes a polypeptide having an amino acid sequence that is at least 80%, 85%, 90%, 95% or 99% identical to the amino acid sequence of SEQ ID NO: 8.

In one embodiment, the core protein encoded by the nucleic acid is perlecan (SEQ ID NO: 21), or a fragment of perlecan comprising one or more GAG attachment sites. In this regard, human perlecan comprises GAG attachment sites in the sequence SGDDLGSGDLGSGD (SEQ ID NO: 9) or SGE (SEQ ID NO: 10). Accordingly, in one embodiment, the core protein comprises the amino acid sequence SGDDLGSGDLGSGD (SEQ ID NO: 9) or SGE (SEQ ID NO: 10). In one embodiment, the core protein comprises an amino acid sequence that comprises one or more GAG attachment sites and is at least 80%, 85%, 90%, 95%, 99% or 100% identical to the amino acid sequence of human perlecan, or a fragment of human perlecan. An example of the amino acid sequence of human perlecan is the amino acid sequence deposited under UNIPROT/SWISS-Prot Accession No. P98160.4 or GENBANK accession no. AAA52700.

The amino acid sequence of the full length protein of human perlecan (with signal sequence underlined) is:

```
                                          (SEQ ID NO: 21)
MGWRAPGALL LALLLHGRLL AVTHGLRAYD GLSLPEDIET

VTASQMRWTH SYLSDDEYML ADSISGDDLG SGDLGSGDFQ

MVYFRALVNF TRSIEYSPQL EDAGSREFRE VSEAVVDTLE

SEYLKIPGDQ VVSVVFIKEL DGWVFVELDV GSEGNADGAQ

IQEMLLRVIS SGSVASYVTS PQGFQFRRLG TVPQFPRACT

EAEFACHSYN ECVALEYRCD RRPDCRDMSD ELNCEEPVLG

ISPTFSLLVE TTSLPPRPET TIMRQPPVTH APQPLLPGSV

RPLPCGPQEA ACRNGHCIPR DYLCDGQEDC EDGSDELDCG

PPPPCEPNEF PCGNGHCALK LWRCDGDFDC EDRTDEANCP

TKRPEEVCGP TQFRCVSTNM CIPASFHCDE ESDCPDRSDE

FGCMPPQVVT PPRESIQASR GQTVTFTCVA IGVPTPIINW

RLNWGHIPSH PRVTVTSEGG RGTLIIRDVK ESDQGAYTCE

AMNARGMVFG IPDGVLELVP QRGPCPDGHF YLEHSAACLP

CFCFGITSVC QSTRRFRDQI RLRFDQPDDF KGVNVTMPAQ

PGTPPLSSTQ LQIDPSLHEF QLVDLSRRFL VHDSFWALPE

QFLGNKVDSY GGSLRYNVRY ELARGMLEPV QRPDVVLVGA
```
-continued
```
GYRLLSRGHT PTQPGALNQR QVQFSEEHWV HESGRPVQRA

ELLQVLQSLE AVLIQTVYNT KMASVGLSDI AMDTTVTHAT

SHGRAHSVEE CRCPIGYSGL SCESCDAHFT RVPGGPYLGT

CSGCSCNGHA SSCDPVYGHC LNCQHNTEGP QCNKCKAGFF

GDAMKATATS CRPCPCPYID ASRRFSDTCF LDTDGQATCD

ACAPGYTGRR CESCAPGYEG NPIQPGGKCR PVNQEIVRCD

ERGSMGTSGE ACRCKNNVVG RLCNECADGS FHLSTRNPDG

CLKCFCMGVS RHCTSSSWSR AQLHGASEEP GHFSLTNAAS

THTTNEGIFS PTPGELGFSS FHRLLSGPYF WSLPSRFLGD

KVTSYGGELR FTVTQRSQPG STPLHGQPLV VLQGNNIILE

HHVAQEPSPG QPSTFIVPFR EQAWQRPDGQ PATREHLLMA

LAGIDTLLIR ASYAQQPAES RVSGISMDVA VPEETGQDPA

LEVEQCSCPP GYRGPSCQDC DTGYTRTPSG LYLGTCERCS

CHGHSEACEP ETGACQGCQH HTEGPRCEQC QPGYYGDAQR

GTPQDCQLCP CYGDPAAGQA AHTCFLDTDG HPTCDACSPG

HSGRHCERCA PGYYGNPSQG QPCQRDSQVP GPIGCNCDPQ

GSVSSQCDAA GQCQCKAQVE GLTCSHCRPH HFHLSASNPD

GCLPCFCMGI TQQCASSAYT RHLISTHFAP GDFQGFALVN

PQRNSRLTGE FTVEPVPEGA QLSFGNFAQL GHESFYWQLP

ETYQGDKVAA YGGKLRYTLS YTAGPQGSPL SDPDVQITGN

NIMLVASQPA LQGPERRSYE IMFREEFWRR PDGQPATREH

LLMALADLDE LLIRATFSSV PLVASISAVS LEVAQPGPSN

RPRALEVEEC RCPPGYIGLS CQDCAPGYTR TGSGLYLGHC

ELCECNGHSD LCHPETGACS QCQHNAAGEF CELCAPGYYG

DATAGTPEDC QPCACPLTNP ENMFSRTCES LGAGGYRCTA

CEPGYTGQYC EQCGPGYVGN PSVQGGQCLP ETNQAPLVVE

VHPARSIVPQ GGSHSLRCQV SGSPPHYFYW SREDGRPVPS

GTQQRHQGSE LHFPSVQPSD AGVYICTCRN LHQSNTSRAE

LLVTEAPSKP ITVTVEEQRS QSVRPGADVT FICTAKSKSP

AYTLVWTRLH NGKLPTRAMD FNGILTIRNV QLSDAGTYVC

TGSNMFAMDQ GTATLHVQAS GTLSAPVVSI HPPQLTVQPG

QLAEFRCSAT GSPTPTLEWT GGPGGQLPAK AQIHGGILRL

PAVEPTDQAQ YLCRAHSSAG QQVARAVLHV HGGGGPRVQV

SPERTQVHAG RTVRLYCRAA GVPSATITWR KEGGSLPPQA

RSERTDIATL LIPAITTADA GFYLCVATSP AGTAQARMQV

VVLSASDASP PGVKIESSSP SVTEGQTLDL NCVVAGSAHA

QVTWYRRGGS LPPHTQVHGS RLRLPQVSPA DSGEYVCRVE

NGSGPKEASI TVSVLHGTHS GPSYTPVPGS TRPIRIEPSS

SHVAEGQTLD LNCVVPGQAH AQVTWHKRGG SLPARHQTHG

SLLRLHQVTP ADSGEYVCHV VGTSGPLEAS VLVTIEASVI

PGPIPPVRIE SSSSTVAEGQ TLDLSCVVAG QAHAQVTWYK
```

-continued

```
RGGSLPARHQ VRGSRLYIFQ ASPADAGQYV CRASNGMEAS

ITVTVTGTQG ANLAYPAGST QPIRIEPSSS QVAEGQTLDL

NCVVPGQSHA QVTWHKRGGS LPVRHQTHGS LLRLYQASPA

DSGEYVCRVL GSSVPLEASV LVTIEPAGSV PALGVTPTVR

IESSSSQVAE GQTLDLNCLV AGQAHAQVTW HKRGGSLPAR

HQVHGSRLRL LQVTPADSGE YVCRVVGSSG TQEASVLVTI

QQRLSGSHSQ GVAYPVRIES SSASLANGHT LDLNCLVASQ

APHTITWYKR GGSLPSRHQI VGSRLRIPQV TPADSGEYVC

HVSNGAGSRE TSLIVTIQGS GSSHVPSVSP PIRIESSSPT

VVEGQTLDLN CVVARQPQAI ITWYKRGGSL PSRHQTHGSH
LRLHQMSVAD SGEYVCRANN NIDALEASIV ISVSPSAGSP
SAPGSSMPIR IESSSSHVAE GETLDLNCVV PGQAHAQVTW
HKRGGSLPSH HQTRGSRLRL HHVSPADSGE YVCRVMGSSG
PLEASVLVTI EASGSSAVHV PAPGGAPPIR IEPSSSRVAE
GQTLDLKCVV PGQAHAQVTW HKRGGNLPAR HQVHGPLLRL
NQVSPADSGE YSCQVTGSSG TLEASVLVTI EPSSPGPIPA
PGLAQPIYIE ASSSHVTEGQ TLDLNCVVPG QAHAQVTWYK
RGGSLPARHQ THGSQLRLHL VSPADSGEYV CRAASGPGPE
QEASFTVTVP PSEGSSYRLR SPVISIDPPS STVQQGQDAS
FKCLIHDGAA PISLEWKTRN QELEDNVHIS PNGSIIITVG
TRPSNHGTYR CVASNAYGVA QSVVNLSVHG PPTVSVLPEG
PVWVKVGKAV TLECVSAGEP RSSARWTRIS STPAKLEQRT
YGLMDSHAVL QISSAKPSDA GTYVCLAQNA LGTAQKQVEV
IVDTGAMAPG APQVQAEEAE LTVEAGHTAT LRCSATGSPA
PTIHWSKLRS PLPWQHRLEG DTLIIPRVAQ QDSGQYICNA
TSPAGHAEAT IILHVESPPY ATTVPEHASV QAGETVQLQC
LAHGTPPLTF QWSRVGSSLP GRATARNELL HFERAAPEDS
GRYRCRVTNK VGSAEAFAQL LVQGPPGSLP ATSIPAGSTP
TVQVTPQLET KSIGASVEFH CAVPSDQGTQ LRWFKEGGQL
PPGHSVQDGV LRIQNLDQSC QGTYICQAHG PWGKAQASAQ
LVIQALPSVL INIRTSVQTV VVGHAVEFEC LALGDPKPQV
TWSKVGGHLR PGIVQSGGVV RIAHVELADA GQYRCTATNA
AGTTQSHVLL LVQALPQISM PQEVRVPAGS AAVFPCIASG
YPTPDISWSK LDGSLPPDSR LENNMLMLPS VRPQDAGTYV
CTATNRQGKV KAFAHLQVPE RVVPYFTQTP YSFLPLPTIK
DAYRKFEIKI TFRPDSADGM LLYNGQKRVP GSPTNLANRQ
PDFISFGLVG GRPEFRFDAG SGMATIRHPT PLALGHFHTV
TLLRSLTQGS LIVGDLAPVN GTSQGKFQGL DLNEELYLGG
YPDYGAIPKA GLSSGFIGCV RELRIQGEEI VFHDLNLTAH
GISHCPTCRD RPCQNGGQCH DSESSSYVCV CPAGFTGSRC
```

-continued

```
EHSQALHCHP EACGPDATCV NRPDGRGYTC RCHLGRSGLR
CEEGVTVTTP SLSGAGSYLA LPALTNTHHE LRLDVEFKPL
APDGVLLFSG GKSGPVEDFV SLAMVGGHLE FRYELGSGLA
VLRSAEPLAL GRWHRVSAER LNKDGSLRVN GGRPVLRSSP
GKSQGLNLHT LLYLGGVEPS VPLSPATNMS AHFRGCVGEV
SVNGKRLDLT YSFLGSQGIG QCYDSSPCER QPCQHGATCM
PAGEYEFQCL CRDGFKGDLC EHEENPCQLR EPCLHGGTCQ
GTRCLCLPGF SGPRCQQGSG HGIAESDWHL EGSGGNDAPG
QYGAYFHDDG FLAFPGHVFS RSLPEVPETI ELEVRTSTAS
GLLLWQGVEV GEAGQGKDFI SLGLQDGHLV FRYQLGSGEA
RLVSEDPIND GEWHRVTALR EGRRGSIQVD GEELVSGRSP
GPNVAVNAKG SVYIGGAPDV ATLTGGRFSS GITGCVKNLV
LHSARPGAPP PQPLDLQHRA QAGANTRPCP S
```

It will also be appreciate that perlecan from species other than human may be used for the core protein. In some other embodiments, the core protein may comprise the amino acid sequence of mouse perlecan (e.g. UniProt/Swiss-Prot accession no. Q05793.1), a fragment thereof comprising one or more GAG attachment sites, or an amino acid sequence that comprises one or more GAG attachment sites and is at least 80%, 85%, 90%, 95%, 99% or 100% identical to the amino acid sequence of mature mouse perlecan or a fragment thereof.

In one embodiment, the nucleic acid encoding the core protein comprises a sequence encoding a polypeptide having an amino acid sequence of SEQ ID NO: 21 and an optional affinity tag. In one embodiment, the nucleic acid encoding the core protein comprises a sequence encoding a polypeptide having an amino acid sequence of residues 23 to 4381 SEQ ID NO: 21, an optional signal sequence and an optional affinity tag.

In one embodiment, the nucleic acid encoding the core protein comprises a sequence encoding a polypeptide having an amino acid sequence comprising a fragment of SEQ ID NO: 21 and one or more GAG attachment sites, an optional signal sequence and an optional affinity tag. In certain aspects, at least one GAG attachment site is contained in the fragment of SEQ ID NO: 21. In certain aspects, the fragment of SEQ ID NO: 21 is from 20 to 500 amino acids in length, from 100 to 700 amino acids in length, from 20 to 100 amino acids in length or from 50 to 200 amino acids in length. In certain aspects, the signal sequence has the sequence of SEQ ID NOS: 16 to 20. In certain aspects, the one or more GAG attachment sites have the sequence of one of Sequences A to M above. In certain aspects, the signal sequence has the sequence of SEQ ID NO: 19 and the one or more GAG attachment sites have the sequence of Sequences, H, I or J (SEQ ID NOS: 14 or 15).

In one embodiment, the nucleic acid encoding the core protein comprises a sequence encoding a polypeptide having an amino acid sequence that is at least 80%, 85%, 90%, 95% or 99% identical to the amino acid sequence of SEQ ID NO: 21, one or more GAG attachment sites, an optional signal sequence and an optional affinity tag. In certain aspects, at least one GAG attachment site is contained in the amino acid sequence that is at least 80%, 85%, 90%, 95% or 99% identical to the amino acid sequence of SEQ ID NO: 21. In certain aspects, the signal sequence has the sequence of SEQ ID NOS: 16 to 20. In certain aspects, the one or more GAG attachment sites have the sequence of one of Sequences A to M above. In certain aspects, the signal sequence has the sequence of SEQ ID NO: 19 and the one or more GAG attachment sites have the sequence of Sequences, H, I or J (SEQ ID NOS: 14 or 15).

The nucleic acid encoding the core protein is typically operably linked to regulatory elements in order to achieve expression in the cell. The expression "operably linked" refers to the placement of a regulatory element in such a manner as to influence the expression of the core from the nucleic acid encoding the core protein. In some embodiments, other nucleic acid sequences including, for example, 5' untranslated region, 3' untranslated regions, cap structure, poly A tail, translational initiators, sequences encoding signalling peptides, translational enhancers, transcriptional enhancers, translational terminators, transcriptional terminators, transcriptional promoters, and/or nucleic acid sequence encoding fusion peptides for isolation of the protein, may be operably linked with the nucleic acid encoding the protein (see, for example, "Molecular Cloning: A Laboratory Manual", Sambrook et al., Cold Spring Harbor Laboratory, 3rd edition (2001)). Depending on the cell and/or vector utilized, any one of a number of suitable regulatory elements may be used. The regulatory elements may be normally associated with the nucleic acid encoding the core protein in vivo. Alternatively, the regulatory elements may be heterologous elements that are not normally associated with the nucleic acid encoding the core protein in vivo. Examples are: tissue specific expression elements, including distinct promoter and enhancer sequences that are derived from different sources and engineered to produce an expression element to regulate the expression of the nucleic acid in specific cell types. Expression elements isolated from the genome of viruses that grow in mammalian cells, (e.g., RSV, vaccinia virus 7.5K, SV40, HSV, adenoviruses MLP, MMTV LTR and CMV promoters) may be used, as well as promoters produced by recombinant DNA or synthetic techniques.

Vectors

As used herein, the term "vector" means any mechanism for the transfer of a nucleic acid into a host cell, either in vitro, ex vivo or in vivo. The term vector includes both viral and non-viral mechanisms for introducing the nucleic acid into a cell of a subject in vitro, ex vivo, or in vivo. Non-viral vectors include but are not limited to plasmids, liposomes, electrically charged lipids (such as cytofectins), DNA-protein complexes, and biopolymers.

Viral vectors include but are not limited to vectors derived from adenoviral vectors, retroviral vectors, lentiviral vectors, bovine papilloma viruses, Epstein-Barr virus, adeno-associated, viruses, pox viruses, baculovirus, vaccinia virus, herpes simplex virus, and hybrids of two or more viral vector types. Such non-viral vectors may be transferred into cells using any of the methods known in the art, including calcium phosphate coprecipitation, lipofection, protoplast fusion, receptor-mediated gene delivery, naked DNA injection, electroporation and bioballistic or particle acceleration. A vector may contain regulatory elements required for expression of the nucleic acid encoding the core protein, such as discussed herein. The regulatory elements may be optimized based on a particular cell type or tissue. In addition, a vector may contain one or more selectable markers useful in selecting, measuring, and monitoring nucleic acid transfer results (transfer to which cells, duration of expression, etc.).

Suitable plasmids for use as vectors include, but are not limited to, the vectors described in the Examples, pCELF, pCELP, pcDNA3, pMClneo, pXT1, pSG5, EBO-pSV2, pBPV-1, pBPV-MMTneo, pRSVgpt, pRSVneo, pSV2-dhfr, pUCTag, IZD35, pHB-Apr-1-neo, EBO-pcD-XN, pcDNA1/amp, pcDNA1/neo, pRc/CMV, pSV2gpt, pSV2neo, pSV2dhfr, pTk2, pMSG, pSVT7, pKoneo and pHyg. Such plasmids may contain an origin of replication for autonomous replication in host cells, selectable markers, a number of useful restriction enzyme sites, a potential for high copy number, and promoters active in a particular cell type.

Typically, the nucleic acid encoding the core protein is introduced into the host cell in a vector, such as an expression vector. Vectors may be commercially obtained from companies such as Promega, Stratagene or InVitrogen. Vectors can also be individually constructed or modified using standard molecular biology techniques. In carrying out the nucleic acid manipulations described herein, including production of vectors, many techniques for manipulating and modifying nucleic acids may be used. Merely exemplifying such techniques are the following: Gene Probes for Bacteria (Macario and De Marcario, editors, Academic Press Inc., 1990); Genetic Analysis, Principles Scope and Objectives (John R. S. Ficham, Blackwell Science Ltd., 1994); Recombinant DNA Methodology II (Ray Wu, editor, Academic Press, 1995); Molecular Cloning. A Laboratory Manual (Maniatis, Fritsch, and Sambrook, editors, Cold Spring Harbor Laboratory, 1982); PCR (Polymerase Chain Reaction), (Newton and Graham, editors, Bios Scientific Publishers, 1994). Each of the foregoing references cited herein are incorporated by reference as if fully set forth in this disclosure.

A vector may contain any number of nucleotide sequences encoding desired elements that may be operably linked to a nucleotide sequence encoding a polypeptide or fusion polypeptide comprising a protein transduction domain. Such nucleotide sequences encoding desired elements, include, for example, transcriptional promoters, transcriptional enhancers, transcriptional terminators, translational initiators, translational, terminators, ribosome binding sites, 5' untranslated region, 3' untranslated regions, cap structure, poly A tail, origin of replication, detectable markers, affinity tags, signal or target peptide. It will be understood that the selection and/or construction of a suitable vector may depend upon several factors, including, for example, the type of cell or host cell, the type of transcriptional and translational control elements desired, the means of isolation of the protein desired, whether chromosomal integration is desired, the type of selection process that is desired.

One or more of the enzymes necessary for synthesis of heparin and/or HS GAG polymer, and/or the linkage tetrasaccharide (e.g. xyl-Gal-Gal-GlcA) which links the heparin/HS molecule to the protein, may also be encoded by one or more nucleic acids that are introduced into the host cell. In certain embodiments, no such enzymes are provided.

In certain embodiments, the vector contains the functional domains, such as a signal sequence and/or an affinity tag, and the nucleic acid encoding the core protein may a functional domain with the functional domain being provided by the vector. In such instances, the recombinant protein/polypeptide produced will contain such functional domains by virtue of their inclusion in the vectors (for example, a plasmid vector).

Cell Culture Medium

In one embodiment, the method of producing a proteoglycan as described herein and/or heparin and/or HS comprises incubating the cell into which the nucleic acid encoding the core protein has been introduced in medium under conditions to promote production of a glycoprotein comprising the core protein linked to heparin and/or HS.

In one embodiment, the method of producing a proteoglycan as described herein and/or heparin and/or HS comprises incubating the cell in medium under conditions which permit expression of the core protein, wherein the medium comprises glucose at a concentration which promotes production of a proteoglycan comprising the core protein linked to heparin and/or HS in an amount that is greater than the amount of other GAGs linked to the core protein.

Typically, the heparin and/or HS is linked to one or more of the attachment sites of the core protein.

The cells are incubated under conditions which promote production of proteoglycan comprising the core protein linked to heparin and/or HS. Typically, the cells are incubated in medium which permits expression of the core protein and promotes linkage of heparin and/or HS, and optionally other GAGs, to the core protein.

In certain embodiments, the conditions to promote the production of a proteoglycan result in a proteoglycan having a specific or desired amount of heparin and/or HS linked thereto, including an increased amount of heparin and/or HS as compared to other GAGs present, and/or a specific distribution of tri, di- and mono-sulfated disaccharide units on the proteoglycan.

The step of incubating the cells in medium which permits expression of the core protein may be accomplished by incubating the cells in a medium which provides sufficient carbon, nitrogen, oxygen and other nutrients, growth factors, buffers, co-factors and any other substance as required to at least maintain the viability of the cells and allow expression of the core protein. For example, cells may be cultured in tissue culture medium such as, for example, RPMI or DMEM supplemented with 10% fetal calf-serum (FCS) and other supplements such as antimicrobial agents, growth factors, other cytokines (see, for example, Cell Biology (Third Edition) A Laboratory Handbook, vol. 1, 2006, Elsevier Inc.). Examples of suitable medium include medium formulations that are known to those skilled in the art such as, for example, RPMI, IMDM, DMEM, DMEM/F12, EMEM with or without serum or with reduced serum, and further optionally including antibiotics, lipids, transferrin, insulin, additional nutrient supplements such as amino acids and co-factors as required. In embodiments in which the nucleic acid encoding the core protein is under the control of an inducible promoter or comprises an inducible promoter, the medium may further include the inducer. The medium may be supplemented with glucose to provide a glucose concentration which promotes production of proteoglycan comprising heparin and/or HS and optionally, sulfate and/or phosphate to provide a sulfate and/or phosphate concentration which promotes production of proteoglycan comprising heparin and/or HS. Generally, cultured cells are incubated at 37° C. in a 5% $CO_2$ atmosphere.

As described in the Examples, the inventors have found that the attachment of heparin and/or HS to a core protein, for example serglycin, can be promoted by culturing the cells in medium containing glucose at a concentration that favours attachment of heparin and/or HS over attachment of other GAGs. As described in the Examples, culturing of HEK293 cells expressing a nucleic acid encoding serglycin in medium comprising glucose at a concentration of 5 mM resulted in production of serglycin having a high proportion of chondroitin sulfate and low amounts of heparin and HS, whereas culturing the same cells in medium comprising 25 mM or 50 mM glucose resulted in production of serglycin having a high proportion of heparin and/or HS. Moreover, the cells cultured in medium comprising 25 mM glucose resulted in production of serglycin with a higher proportion of heparin and/or HS relative to chondroitin sulfate or other GAGs. Moreover, as described in the Examples, the heparin and/or HS linked to the serglycin exhibits anticoagulant activity. As described herein, culturing of the cells in medium comprising 50 mM glucose resulted in production of serglycin with similar amounts of heparin and/or HS and chondroitin sulfate attached to the protein.

Accordingly, the inventors have found that the concentration of glucose in the culture medium influences the type of GAGs that are synthesized on the core protein.

In one embodiment, the medium comprises glucose at a concentration which promotes production of the protein with heparin and/or HS linked to the core protein, typically linked to the attachment site of the core protein, in an amount that is greater than the amount of other GAGs linked to the core protein.

In various embodiments, the concentration of glucose in the medium is in the range of from 5 mM to 75 mM, 5 mM to 60 mM, 5 mM to 50 mM, 10 mM to 45 mM, 15 mM to 35 mM, 20 mM to 30 mM. In other embodiments, the concentration of glucose in the medium is in the range of 20 mM to 30 mM, 21 mM to 29 mM, 22 mM to 27 mM, 23 mM to 26 mM or 24 mM to 25 mM.

In still other embodiments, the concentration of glucose in the medium is in the range of 15 mM to 35 mM, 16 mM to 34 mM, 17 mM to 33 mM, 18 mM to 32 mM, or 19 to 31 mM.

In one embodiment, the medium comprises sulfate at a concentration which promotes the production of the core protein with heparin and/or HS linked to the core protein, typically linked to the attachment site of the core protein, in an amount that is greater than the amount of other GAGs linked to the core protein.

In various embodiments, the concentration of sulfate in the medium is in the range of from 0.5 mM to 50 mM, 0.5 mM to 45 mM, 0.5 mM to 40 mM, 1 mM to 50 mM, 1.5 mM to 50 mM, 2 mM to 50 mM, 5 mM to 50 mM, 10 mM to 50 mM, 20 mM to 50 mM, 30 mM to 50 mM, 40 mM to 50 mM.

In one embodiment, the medium comprises phosphate at a concentration which promotes the production of the protein with heparin and/or HS linked to the core protein, typically linked to the attachment site of the core protein, in an amount that is greater than the amount of other GAGs linked to the core protein.

In various embodiments, the concentration of phosphate in the medium is in the range of from 0.5 mM to 50 mM, 0.5 mM to 45 mM, 0.5 mM to 40 mM, 1 mM to 50 mM, 1.5 mM to 50 mM, 2 mM to 50 mM, 5 mM to 50 mM, 10 mM to 50 mM, 20 mM to 50 mM, 30 mM to 50 mM, 40 mM to 50 mM.

In one embodiment, the medium comprises glucose, sulfate and phosphate at a concentration which promotes the production of the core protein with heparin and/or HS linked to the core protein, typically linked to the attachment site of the core protein, in an amount that is greater than the amount of other GAGs linked to the core protein.

In various embodiments:
(a) the concentration of glucose in the medium is in the range of from 5 mM to 75 mM, 5 mM to 60 mM, 5 mM to 50 mM, 10 mM to 45 mM, 15 mM to 35 mM, 20 mM to 30 mM;
(b) the concentration of sulfate in the medium is in the range of from 0.5 mM to 50 mM, 0.5 mM to 45 mM, 0.5 mM to 40 mM, 1 mM to 50 mM, 1.5 mM to 50 mM, 2 mM to 50 mM, 5 mM to 50 mM, 10 mM to 50 mM, 20 mM to 50 mM, 30 mM to 50 mM, 40 mM to 50 mM; and (c) the concentration of phosphate in the medium is in the range of from 0.5 mM to 50 mM, 0.5 mM to 45 mM, 0.5 mM to 40 mM, 1 mM to 50 mM, 1.5 mM to 50 mM, 2 mM to 50 mM, 5 mM to 50 mM, 10 mM to 50 mM, 20 mM to 50 mM, 30 mM to 50 mM, 40 mM to 50 mM.

In additional embodiments:

(a) the concentration of glucose in the medium is in the range of from 20 mM to 30 mM, 21 mM to 29 mM, 22 mM to 27 mM, 23 mM to 26 mM or 24 mM to 25 mM;

(b) the concentration of sulfate in the medium is in the range of from 0.5 mM to 50 mM, 0.5 mM to 45 mM, 0.5 mM to 40 mM, 1 mM to 50 mM, 1.5 mM to 50 mM, 2 mM to 50 mM, 5 mM to 50 mM, 10 mM to 50 mM, 20 mM to 50 mM, 30 mM to 50 mM, 40 mM to 50 mM; and (c) the concentration of phosphate in the medium is in the range of from 0.5 mM to 50 mM, 0.5 mM to 45 mM, 0.5 mM to 40 mM, 1 mM to 50 mM, 1.5 mM to 50 mM, 2 mM to 50 mM, 5 mM to 50 mM, 10 mM to 50 mM, 20 mM to 50 mM, 30 mM to 50 mM, 40 mM to 50 mM.

In still additional embodiments:

(a) the concentration of glucose in the medium is in the range of from 15 mM to 35 mM, 16 mM to 34 mM, 17 mM to 33 mM, 18 mM to 32 mM, or 19 to 31 mM;

(b) the concentration of sulfate in the medium is in the range of from 0.5 mM to 50 mM, 0.5 mM to 45 mM, 0.5 mM to 40 mM, 1 mM to 50 mM, 1.5 mM to 50 mM, 2 mM to 50 mM, 5 mM to 50 mM, 10 mM to 50 mM, 20 mM to 50 mM, 30 mM to 50 mM, 40 mM to 50 mM; and (c) the concentration of phosphate in the medium is in the range of from 0.5 mM to 50 mM, 0.5 mM to 45 mM, 0.5 mM to 40 mM, 1 mM to 50 mM, 1.5 mM to 50 mM, 2 mM to 50 mM, 5 mM to 50 mM, 10 mM to 50 mM, 20 mM to 50 mM, 30 mM to 50 mM, 40 mM to 50 mM.

Heparin and/or Heparan Sulfate Proteoglycans

The methods described allow the production of a core protein linked, typically to the GAG attachment site of the core protein, to heparin and/or HS and optionally other GAGs (i.e., a proteoglycan). In one embodiment, the methods described allow the production of a core protein linked, typically to the GAG attachment site of the core protein, to heparin and/or HS wherein the amount of heparin and/or HS is greater than the amount of other GAGs linked to the core protein.

As discussed herein, the core protein may comprise an amino acid sequence of a proteoglycan, or a fragment thereof, containing one or more GAG attachment sites. A variety of proteoglycan amino acid sequences may be used.

In one embodiment, the core protein comprises the amino acid sequence of serglycin (whether from human, rat or mouse), or a fragment thereof, containing one or more GAG attachment sites. In a particular embodiment, the core protein comprises the amino acid sequence of mature human serglycin (SEQ ID NO: 2), or a fragment thereof, containing one or more GAG attachment sites (such as, for example a GAG attachment site of sequences A to M, or particularly sequence E) and an optional signal sequence (such as, for example a signal sequence of SEQ ID NOS: 16-19, or particularly SEQ ID NO: 16) and/or optional affinity tag. In another particular embodiment, the core protein comprises the amino acid sequence of mature human serglycin (SEQ ID NO: 3), or a fragment thereof, containing one or more GAG attachment sites (such as, for example a GAG attachment site of sequences A to M, or particularly sequence E) and an optional signal sequence (such as, for example a signal sequence of SEQ ID NOS: 16-19, or particularly SEQ ID NO: 16) and/or optional affinity tag.

When the core protein is to be used in methods of preparing heparin and/or HS, the core protein typically contains an affinity tag to allow for the efficient purification of the core protein, although the affinity tag may be absent. When the core protein is used directly as an anticoagulant, the core protein may have an affinity tag or may lack an affinity tag.

In certain embodiments, the heparin and/or HS linked to the core protein comprises: a) 10-50% tri-sulfated disaccharides, 30-50% di-sulfated disaccharides, and 10-30% mono-sulfated disaccharides; b) 10-40% tri-sulfated disaccharides, 35-45% di-sulfated disaccharides, and 10-25% mono-sulfated disaccharides; c) 15-40% tri-sulfated disaccharides, 35-45% di-sulfated disaccharides, and 10-25% mono-sulfated disaccharides; d) 5-25% tri-sulfated disaccharides, 30-50% di-sulfated disaccharides, and 10-20% mono-sulfated disaccharides; or e) 1-30% tri-sulfated disaccharides, 25-55% di-sulfated disaccharides, and 5-40% mono-sulfated disaccharides.

In certain embodiments, the heparin and/or HS linked to the core protein comprises: a) 15-40% tri-sulfated disaccharides; b) 35-45% di-sulfated disaccharides; c) 10-25% mono-sulfated disaccharides; d) 10-50% tri-sulfated disaccharides; e) 30-50% di-sulfated disaccharides; f) 10-30% mono-sulfated disaccharides; g) 15-30% tri-sulfated disaccharides; h) 40-45% di-sulfated disaccharides; i) 10-15% mono-sulfated disaccharides; j) 5-25% tri-sulfated disaccharides; k) 1-30% tri-sulfated disaccharides; l) 30-50% di-sulfated disaccharides; m) 25-55% di-sulfated disaccharides; n) 10-20% mono-sulfated disaccharides; or p) 5-40% mono-sulfated disaccharides.

The heparin and/or HS linked to the core protein may contain disaccharide repeats of varying lengths. A heparin disaccharide includes any of the following, wherein the disaccharides may be present in any order in the heparin and/or HS chains: UA-GlcNAc; UA-GlcNAc(6S); UA(2S)-GlcNAc; UA-(2S)-ClcNAc(6S); UA-GlcNS; UA-GlcNS(6S); UA(2S)-GlcNS; and UA(2S)-GlcNS(6S), wherein UA is a uronic acid residue (i.e., glucuronic acid or iduronic acid);

Ac is acetyl;

GlcNAc is N-acetyl glucosamine;

GlcNS is glucosamine-N-sulfate;

2S is 2-O-sulfate;

6S is 6-O-sulfate.

In various embodiments, the heparin/HS comprises disaccharides which are at least 50% sulfated, at least 60% sulfated, at least 70% sulfated or at least 80% sulphated.

In certain embodiments, the heparin and/or HS linked to the core protein comprises heparin and/or HS in the range of from 20% to 100%, 30% to 90%, 40% to 80% or 50% to 80% of the total GAG attached to the core protein. In one embodiment, the recombinant proteoglycan comprises heparin and/or HS in the range from 1% to 30%, from 1% to 25%, from 1% to 20%, from 1% to 15% or from 1% to 10% of the total GAG attached to the core protein.

In a particular embodiment, recombinant proteoglycan is serglycin, or a fragment thereof, linked to one or more heparin and/or HS chains.

In certain embodiments, the heparin and/or HS linked to the recombinant serglycin, or fragment thereof, comprises: a) 10-50% tri-sulfated disaccharides, 30-50% di-sulfated disaccharides, and 10-30% mono-sulfated disaccharides; b) 10-40% tri-sulfated disaccharides, 35-45% di-sulfated disaccharides, and 10-25% mono-sulfated disaccharides; c) 15-40% tri-sulfated disaccharides, 35-45% di-sulfated disaccharides, and 10-25% mono-sulfated disaccharides; d) 5-25% tri-sulfated disaccharides, 30-50% di-sulfated disaccharides, and 10-20% mono-sulfated disaccharides; or e) 1-30% tri-sulfated disaccharides, 25-55% di-sulfated disaccharides, and 5-40% mono-sulfated disaccharides.

In certain embodiments, the heparin and/or HS linked to the recombinant serglycin, or fragment thereof, comprises: a) 15-40% tri-sulfated disaccharides; b) 35-45% di-sulfated disaccharides; c) 10-25% mono-sulfated disaccharides; d) 10-50% tri-sulfated disaccharides; e) 30-50% di-sulfated disaccharides; f) 10-30% mono-sulfated disaccharides; g) 15-30% tri-sulfated disaccharides; h) 40-45% di-sulfated disaccharides; i) 10-15% mono-sulfated disaccharides; j) 5-25% tri-sulfated disaccharides; k) 1-30% tri-sulfated disaccharides; l) 30-50% di-sulfated disaccharides; m) 25-55% di-sulfated disaccharides; n) 10-20% mono-sulfated disaccharides; or p) 5-40% mono-sulfated disaccharides.

The heparin and/or HS linked to the recombinant serglycin, or fragment thereof, may contain disaccharide repeats of varying lengths. A heparin disaccharide includes any of the following, wherein the disaccharides may be present in any order in the heparin and/or HS chains: UA-GlcNAc; UA-GlcNAc(6S); UA(2S)-GlcNAc; UA-(2S)-ClcNAc(6S); UA-GlcNS; UA-GlcNS(6S); UA(2S)-GlcNS; and UA(2S)-GlcNS(6S), wherein the variables are as defined above.

In various embodiments, the heparin/HS linked to the recombinant serglycin, or fragment thereof, comprises disaccharides which are at least 50% sulfated, at least 60% sulfated, at least 70% sulfated or at least 80% sulphated.

In certain embodiments, the heparin and/or HS linked to the recombinant serglycin, or fragment thereof, comprises heparin and/or HS in the range of from 20% to 100%, 30% to 90%, 40% to 80% or 50% to 80% of the total GAG attached to the core protein. In one embodiment, the recombinant serglycin, or fragment thereof, comprises heparin and/or HS in the range from 1% to 30%, from 1% to 25%, from 1% to 20%, from 1% to 15% or from 1% to 10% of the total GAG attached to the core protein.

Therefore, the present disclosure provides for a recombinant serglycin, or fragment thereof, having the above characteristics. The recombinant serglycin, or fragment thereof, comprising heparin and/or HS typically has anticoagulant activity.

In one embodiment, the recombinant serglycin, or fragment thereof, comprises heparin, and optionally other GAGs. In one embodiment, the recombinant serglycin, or fragment thereof, comprises HS, and optionally other GAGs. In one embodiment, the recombinant serglycin, or fragment thereof, comprises heparin and HS, and optionally other GAGs.

Once expressed, the recombinant proteoglycan (i.e., the core protein linked to heparin and/or HS and optionally other GAGs) may be isolated using methods known in the art for the isolation of proteins. For example, the recombinant proteoglycan may be expressed with a tag which facilitates isolation of the proteoglycan, such as an affinity tag, as discussed above. Examples of affinity tags include polyhistidine (His6) tag which allow isolation using metal matrices such as nickel matrices, chitin binding protein (CBP), maltose binding protein (MBP), glutathione-S-transferase (GST), FLAG tag, or epitope tag. Methods for protein isolation using affinity tags are known in the art.

As described in the Examples, the inventors have found that recombinant proteoglycan produced as described herein comprises heparin and/or HS which comprises up to 80% of its disaccharides sulfated. This level of sulfation is comparable to the level of sulfation observed in the disaccharides of heparin derived from animal tissue used in pharmaceutical preparations.

The isolated recombinant proteoglycans, including recombinant serglycin, linked to heparin and/or HS, may be used in the pharmaceutical compositions and methods of the present disclosure.

Isolated Heparin and/or Heparan Sulfate

Typically, once a proteoglycan comprising a core protein, such as serglycin or a fragment thereof, linked to heparin and/or HS, is produced, the heparin and/or HS may be isolated from the core protein. The heparin and/or HS is isolated from the core protein typically by detaching the heparin/HS from the core protein. Methods for the detachment of heparin and/or HS from core proteins are known in the art and include, for example, enzymatic digestion with, for example, heparinase. Heparinases are commercially available from, for example, Sigma Aldrich (St. Louis, USA), R&D Systems, Inc. (Minneapolis, USA). Heparinases may be used in partial digests of the proteoglycans to produce short chains of heparin and/or HS. Methods for the detachment of GAGs from core proteins are known in the art and include, for example, treatment with sodium hydroxide or alkaline borohydride.

Thus, another aspect provides isolated heparin and/or HS derived from the recombinant proteoglycans of the present disclosure produced by the methods described herein. The isolated heparin and/or HS will have generally the same characteristics as the heparin and/or HS present on the recombinant proteoglycan.

In various embodiments, the isolated heparin/HS comprises disaccharides which are at least 50% sulfated, at least 60% sulfated, at least 70% sulfated, at least 80% sulphated.

In various embodiments, the isolated heparin/heparan sulphate comprises:
(a) 10-50% tri-sulfated disaccharides, 30-50% di-sulfated disaccharides, and 10-30% mono-sulfated disaccharides;
(b) 10-40% tri-sulfated disaccharides, 35-45% di-sulfated disaccharides, and 10-25% mono-sulfated disaccharides;
(c) 15-40% tri-sulfated disaccharides, 35-45% di-sulfated disaccharides, and 10-25% mono-sulfated disaccharides;
(d) 5-25% tri-sulfated disaccharides, 30-50% di-sulfated disaccharides, and 10-20% mono-sulfated disaccharides;
(e) 1-30% tri-sulfated disaccharides, 25-55% di-sulfated disaccharides, and 5-40% mono-sulfated disaccharides;
(f) 15-40% tri-sulfated disaccharides;
(g) 35-45% di-sulfated disaccharides;
(h) 10-25% mono-sulfated disaccharides;
(i) 10-50% tri-sulfated disaccharides;
(j) 30-50% di-sulfated disaccharides;
(k) 10-30% mono-sulfated disaccharides;
(l) 15-30% tri-sulfated disaccharides;
(m) 40-45% di-sulfated disaccharides;
(n) 10-15% mono-sulfated disaccharides;
(o) 5-25% tri-sulfated disaccharides;
(p) 1-30% tri-sulfated disaccharides;
(q) 30-50% di-sulfated disaccharides;
(r) 25-55% di-sulfated disaccharides;

(s) 10-20% mono-sulfated disaccharides; and (t) 5-40% mono-sulfated disaccharides.

The isolated heparin and/or HS may contain disaccharide repeats of varying lengths, depending, at least in part on the conditions under which the A heparin and/or HS chains are removed. A heparin disaccharide includes any of the following, wherein the disaccharides may be present in any order in the heparin and/or HS chains: Δ-UA-GlcNAc; Δ-UA-GlcNAc(6S); Δ-UA(2S)-GlcNAc; Δ-UA-(2S)-ClcNAc(6S); Δ-UA-GlcNS; Δ-UA-GlcNS(6S); Δ-UA(2S)-GlcNS; and Δ-UA(2S)-GlcNS(6S), wherein Δ-UA is 4,5 unsaturated uronic acid residue (i.e., glucuronic acid or iduronic acid);

Ac is acetyl;

GlcNAc is N-acetyl glucosamine;

GlcNS is glucosamine-N-sulfate;

2S is 2-O-sulfate;

6S is 6-O-sulfate.

In certain aspects, the 4,5 unsaturated uronic acid residue is treated so that the double bond between the C-4 and C-5 carbons is removed. In certain aspects, the 4,5 unsaturated uronic acid residue is removed from the disaccharide chain. The foregoing may be beneficial to remove the 4,5 unsaturated uronic acid residue as such molecules do not occur naturally.

Another aspect provides heparin and/or HS comprising about 10-20% tri-sulfated disaccharides, 30-50% di-sulfated disaccharides and about 20-30% mono-sulfated disaccharides. In one embodiment, the heparin and/or heparin sulphate comprises about 15-20% tri-sulfated disaccharides, about 35-45% di-sulfated disaccharides and about 20-30% mono-sulfated disaccharides, typically about 15% tri-sulfated disaccharides, about 40% di-sulfated disaccharides and about 25% mono-sulfated disaccharides.

The isolated heparin and/or HS may be used in the pharmaceutical compositions and methods of the present disclosure.

Pharmaceutical Compositions

The present disclosure also relates to a pharmaceutical composition comprising recombinant proteoglycan comprising a core protein linked to heparin and/or HS produced by the methods described herein.

The present disclosure also relates to a pharmaceutical composition comprising recombinant proteoglycan comprising serglycin or a fragment thereof linked to heparin and/or HS produced by the methods described herein.

The present disclosure also relates to a pharmaceutical composition comprising heparin and/or HS produced by the methods described herein.

Another aspect provides a pharmaceutical composition comprising a recombinant proteoglycan comprising a core protein linked to heparin and/or HS produced by the methods described herein, a recombinant proteoglycan comprising serglycin or a fragment thereof linked to heparin and/or HS and/or a heparin and/or HS as describe herein, and a pharmaceutically acceptable carrier. A "pharmaceutically acceptable carrier" is a carrier that it is compatible with the other ingredients of the composition and is not deleterious to a subject.

The composition may contain other therapeutic agents as described below, and may be formulated, for example, by employing conventional vehicles or diluents, as well as pharmaceutical additives of a type appropriate to the mode of desired administration (for example, excipients, binders, preservatives, stabilizers, antioxidants, etc.) according to techniques such as those well known in the art of pharmaceutical formulation (See, for example, Remington: The Science and Practice of Pharmacy, 21st Ed., 2005, Lippincott Williams & Wilkins).

The pharmaceutical compositions may be in the form of a sterile injectable aqueous. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution.

The pharmaceutical compositions can be administered in a wide variety of dosage forms for administration. For example, the compositions can be administered in forms, such as, but not limited to, tablets, capsules, sachets, lozenges, troches, pills, powders, granules, elixirs, tinctures, solutions, suspensions, elixirs, syrups, ointments, creams, pastes, emulsions, or solutions for intravenous administration or injection. Other dosage forms include administration transdermally, via patch mechanism or ointment. Any of the foregoing may be modified to provide for timed release and/or sustained release formulations.

In certain aspects, the pharmaceutical compositions contain at least one nucleic acid encoding a core protein, an expressed recombinant proteoglycan or heparin and/or HS, each of the foregoing as described herein, as an active ingredient, and are typically administered with a pharmaceutically acceptable carrier. The nucleic acid encoding the core protein may be administered with or as a part of a vector. Such pharmaceutically acceptable carriers include, but are not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, for oral administration in solid form, such as but not limited to, tablets, capsules, sachets, lozenges, troches, pills, powders, or granules, the nucleic acid molecules of the present disclosure may be combined with an oral, non-toxic pharmaceutically acceptable inert carrier, such as, but not limited to, inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarnellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art. For oral liquid forms, such as but not limited to, tinctures, solutions, suspensions, elixirs, syrups, the active ingredients may be dissolved in diluents, such as water, saline, or alcohols. Furthermore, the oral liquid forms may comprise suitably flavored suspending or dispersing agents such as the synthetic and natural gums, for example, tragacanth, acacia, methylcellulose and the like. Moreover, when desired or necessary, suitable and coloring agents or other accessory agents can also be incorporated into the mixture. Other dispersing agents that may be employed include glycerin and the like. Regardless of the form, the compositions of the present disclosure may comprise sodium N-(8-(2-hydroxybenzoyl)amino)caprylate, particularly when heparin and/or HS is the active ingredient.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The nucleic acid molecules of the present disclosure can be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as, but not limited to, a soap, an oil or a detergent, suspending agent, such as, but not limited to, pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkylbeta-aminopropionates, and 2-alkylimidazoline quaternary ammonium salts, and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight.

Topical dosage forms, such as, but not limited to, ointments, creams, pastes, emulsions, containing the nucleic acid molecule of the present disclosure, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery or may be applied to a bandage or dressing.

The compounds of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

Methods of Treatment and Prevention

Another aspect provides a method of treating or preventing blood coagulation or a condition associated with, or caused by blood coagulation, in a subject in need thereof, comprising administering an effective amount of heparin and/or HS isolated from a recombinant proteoglycan comprising a core protein, for example serglycin or a fragment thereof, linked to heparin and/or HS, or an effective amount of the pharmaceutical composition comprising heparin and/or HS as described herein.

Another aspect provides a method of treating or preventing blood coagulation or a condition associated with, or caused by blood coagulation, in a subject in need thereof, comprising administering an effective amount of a recombinant proteoglycan comprising a core protein linked to heparin and/or HS, or an effective amount of a pharmaceutical composition comprising a recombinant proteoglycan comprising a core protein linked to heparin and/or HS as described herein.

Another aspect provides a method of treating or preventing blood coagulation or a condition associated with, or caused by blood coagulation, in a subject in need thereof, comprising administering an effective amount of a recombinant proteoglycan comprising serglycin, or a fragment thereof, linked to heparin and/or HS, or an effective amount of a pharmaceutical composition comprising a recombinant proteoglycan comprising serglycin, or a fragment thereof, linked to heparin and/or HS as described herein.

As used herein, "treating" means affecting a subject, tissue or cell to obtain a desired pharmacological and/or physiological effect and includes inhibiting the condition, i.e. arresting its development; or relieving or ameliorating the effects of the condition i.e., cause reversal or regression of the effects of the condition; such treating need not be 100% effective. As used herein, "preventing" means preventing a condition from occurring in a cell or subject that may be at risk of having the condition, but does not necessarily mean that condition will not eventually develop, or that a subject will not eventually develop a condition. Preventing includes delaying the onset of a condition in a cell or subject. In one embodiment, treating achieves the result of reversing blood coagulation or reversing or improving a condition associated with or caused, at least in part, by blood coagulation in the recipient subject. In one embodiment, preventing achieves the result of preventing or delaying the onset of blood coagulation or a condition associated with or caused, at least in part, by blood coagulation in a recipient subject.

As used herein, the term "subject" refers to a mammal. The mammal may, for example, be a human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Typically the mammal is a human or primate. More typically, the mammal is a human.

A condition associated with or caused, at least in part, by blood coagulation includes, for example, acute coronary syndrome, atrial fibrillation, deep-vein thrombosis or pulmonary embolism.

The term "administering" should be understood to mean providing a compound of the invention to a subject in need of treatment.

As used herein, an "effective amount" refer to an amount that provides a therapeutic benefit in the treatment, prevention, or management of blood coagulation or a condition associated with blood coagulation. The specific amount that is effective can be readily determined by an ordinary medical practitioner, and may vary depending on factors known in the art, such as, e.g. the type of condition, the patient's history, size, weight and age etc.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual molecules encompassed by the invention can be made using conventional methodologies or on the basis of in vivo testing using an appropriate animal model, as described elsewhere herein.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

In the specification and the appended claims, singular forms, including the singular forms "a", "an" and "the", specifically also encompass the plural referents of the terms to which they refer unless the context clearly dictates otherwise.

The disclosure will now be described by way of reference only to the following non-limiting examples. It should be understood, however, that the examples following are illustrative only, and should not be taken in any way as a restriction on the generality of the invention described herein.

Materials and Methods

Vector Construction and Expression Plasmids

Total RNA was extracted from the human mast cell line, HMC-1 using Trizol® (guanidinium thiocyanate). First strand cDNA synthesis was carried out using the ProtoScript® First Strand cDNA synthesis kit (New England Biolabs, Ipswich, Mass., USA) according to the manufacturer's protocol. Amplification was carried out using the PCR master mix (Promega, Madison, Wis., USA). The primers, forward: 5'-ATGGATCCACCATGATGCA-GAAGCTACTCAAATGC-3' (SEQ ID NO: 22) and reverse: 5'-ATGAATTCTAACATAAAATCCTCTTCTAATC-CATGT-3' SEQ ID NO: 23) were designed to amplify the 477 bp coding sequence that contained both the signal and mature peptides of serglycin (FIG. 1A). The forward primer contained a Kozak sequence (bold) between the start codon and the BamHI site at the 5' end. The reverse primer contains a Hind111 site at the 5' end and an EcoRI site. The stop codon in the reverse primer was changed to TAA that would be translated into leucine (underlined). The PCR products were cloned into the CELF and CEFL2 vectors between the BamHI and EcoRI restriction sites using T4 DNA ligase (Promega, Madison, Wis., USA). The CEFL2 vector contained the mammalian promoter, huEF1 alpha, polyhistidine (His6) tag as well as a geneticin (G418) resistant gene. CEFLP vector contained the mammalian promoter, huEF1 alpha, His6 tag, mCherry tag and puromycin resistance gene. The mCherry and His6 tags were located downstream of the serglycin cDNA enabling these features to be translated on the C-terminus of the expressed serglycin (FIGS. 1B and C). The plasmid was amplified in *E. coli* JM-109 cells and the maintenance of the correct reading frame after cloning was verified by sequencing.

Establishment of the serglycin expressing cell lines HEK-293 and HEK-293T cell lines producing recombinant human serglycin (SRGN) were established by transfection of plasmid DNA into cells using Lipofectamine® 2000 (Life Technologies). The HEK-293T cell line is G418 resistant so the CELFP-SRGN was transfected into this cell line while the HEK-293 cell line was transfected with the CEFL2-SRGN. The HEK-293T and HEK-293 cell lines expressing serglycin were selected using 2 µg/mL puromycin and 400 µg/mL geneticin (G418), respectively. The HEK-293 cells transfected with CEFL2-SRGN (designated HEK-293-SRGN) expressed a serglycin that was modified with a C-terminal His6 tag. The HEK-293T cells transfected with CELFP-SRGN (designated HEK-293T-SRGN) expressed a serglycin modified with a C-terminal mCherryHis6 tag.

Culture Conditions

Cells were cultured in DMEM culture medium containing 5.5, 25 or 50 mM glucose, 10% (v/v) fetal bovine serum and 100 µg/mL antibiotics at 37° C., 5% $CO_2$ in a humidified incubator.

Immunofluorescence

Cells were seeded onto microscope slides (SuperFrost® Ultraplus, Lomb Scientific, Taren Point, Australia) at a density of $1 \times 10^5$ cells/mL and cultured for 3 days. Slides were rinsed twice with 50 mM Tris-HCl, pH 7.6, containing 0.15 M NaCl (TBS), 4% (w/v) paraformaldehyde for 15 min at room temperature and permeabilized with 300 mM sucrose, 50 mM NaCl, 3 mM MgCl2, 2 mM HEPES, 0.5% Triton™ X-100 (CAS No. 9002-93-1), pH 7.2, for 5 min on ice. Slides were then blocked with 1% (w/v) BSA in TBS containing 0.05% (w/v) Tween® 20 (CAS Number: 9005-64-5) (TBST) for 1 h at room temperature, followed by incubation rabbit polyclonal anti-serglycin antibody (ascites 1:1000) (Theocharis et al. 2006), diluted in 1% (w/v) BSA in TBST for 16 h at 4° C. The slides were then rinsed three times in TBST and incubated with biotinylated anti-rabbit Ig secondary antibody (1:500 dilution) for 1 h at room temperature. The slides were then rinsed again with TBST before incubation with streptavidin-FITC (GE Healthcare, 1:250 dilution) for 30 min at room temperature, followed by four rinses in TBST. The slides were then counterstained with 4-,6-diamidino-2-phenylindole, dilactate (DAPI) (Life Technologies, Mulgrave, VIC, Australia, 1 µg/mL) in DPBS for 10 min in the dark and rinsed four times with the deionized water before imaging using fluorescence microscopy (Zeiss Axioskop Mot Mat 2, Sydney, Australia).

Isolation of Serglycin

Serglycin was isolated by either immobilized metal affinity chromatography (IMAC) or anion exchange chromatography. IMAC was performed using a HiTrap® chelating high performance column attached to a FPLC system (AKTA purifier, GE Healthcare, Australia). Briefly, the HiTrap® chelating column was equilibrated at 1 mL/min with running buffer (0.02M sodium phosphate, 0.5M NaCl, 40 mM imidazole, pH 7.4) before the addition of medium conditioned by cells and baseline absorbance re-established with the running buffer. Molecules of interest were eluted using 0.02M sodium phosphate, 0.5M NaCl, 0.5 M imidazole, pH 7.4 and concentrated. Anion exchange chromatography using a diethylaminoethyl column (50 mL DEAE Sepharose® Fast Flow, GE Healthcare, Sydney, Australia) attached to a FPLC (Biologic, Biorad, Sydney, Australia) was used to enrich the medium for recombinantly expressed serglycin. The DEAE column was equilibrated at 1 mL/min with running buffer (250 mM NaCl, 20 mM Tris, 10 mM EDTA, pH 7.5) before the addition of medium conditioned by cells and baseline absorbance re-established with running buffer. Molecules of interest were eluted using an eluting buffer (1 M NaCl, 20 mM Tris, 10 mM EDTA, pH 7.5) and concentrated. Serglycin-enriched fractions were subsequently concentrated and analyzed for protein concentration using a Coomassie Blue protein assay (Thermo Scientific, Scoresby, Australia).

Endoglycosidase Digestion

Samples were digested with 50 mU/mL proteinase-free chondroitinase (C'ase) ABC, ACII or B ((Seikagaku Corp., Tokyo, Japan) in 0.1 M Tris acetate, pH 8 at 37° C. for 16 h to confirm the presence and structure of the CS/DS. Samples were digested with 10 mU/mL of heparinase (Hep) III (Seikagaku Corp., Tokyo, Japan) diluted in 10 mM Tris-HCl, pH 7.4 at 37° C. for 16 h to determine the presence of HS.

ELISA

Serglycin-enriched samples (10 µg/ml based on Coomassie Blue protein assay) with and without endoglycosidase digestion were coated onto high binding 96-well ELISA plates (Greiner, Australia) for 2 h at 25° C. Wells were rinsed twice with Dulbecco's phosphate-buffered saline, pH 7.4 (DPBS) followed by blocking with 0.1% (w/v) casein in DPBS for 1 h at 25° C. Wells were rinsed twice with DPBS with 1% (v/v) Tween® 20 (PBST) followed by incubation with primary antibodies diluted in 0.1% (w/v) casein in DPBS for 2 h at 25° C. Primary antibodies used included a rabbit polyclonal anti-serglycin antibody (ascites 1:500), mouse monoclonal anti-polyhistidine tag antibody (Life Technologies, Mulgrave, VIC, Australia; 1:1000), mouse monoclonal anti-CS types A and C (clone CS-56, Sigma Aldrich, St. Louis, Mo., USA; ascites 1:1000), mouse monoclonal anti-CS types A and D (clone LY-111, Seikagaku Corp., Tokyo, Japan; 2 µg/mL); mouse monoclonal anti-CS type D (clone MO-225, Seikagaku Corp., Tokyo, Japan; 2 µg/mL), mouse monoclonal anti-HS (clone 10E4, Seikagaku Corp., Tokyo, Japan; 1 µg/mL), mouse monoclonal antibodies reactive to the linkage regions of CS stubs that remain after chondroitinase ABC digestion (clones 1B5, 2B6 and 3B3 were gifts from Prof. Bruce Caterson, Cardiff University, UK; ascites 1:1000) and mouse monoclonal anti-HS/heparin linkage region generated after Hep III digestion (clone 3G10, Seikagaku Corp., Tokyo, Japan; 1 µg/mL). Wells were rinsed twice with PBST followed by incubation with biotinylated secondary antibodies (1:1000) diluted in 0.1% (w/v) casein in DPBS for 1 h at 25° C., rinsed again twice with PBST, and then incubated with streptavidin-HRP (1:500) for 30 min at 25° C. Binding of the antibodies to the samples was detected using the colorimetric substrate, 2,2-azinodi-(3-ethylbenzthiazoline sulfonic acid), and absorbance was measured at 405 nm.

Western Blot Analysis

Serglycin-enriched samples (50 µg/mL based on Coomassie protein assay) with and without endoglycosidase digestion were electrophoresed in 4-12% (w/v) BisTris gels (Life Technologies, Mulgrave, VIC, Australia) under non-reducing conditions using MES buffer (50 mM MES, 50 mM Tris, 0.1% (w/v) SDS, 1 mM EDTA, pH 7.3) at 200 V for 45 min. A series of molecular mass markers (Precision Plus All Blue, Biorad, Sydney, Australia) were electrophoresed on each gel. Samples were then transferred to polyvinylidene difluoride (PVDF) membrane using transfer buffer (5 mM Bicine, 5 mM BisTris, 0.2 mM EDTA, 50 µg/mL SDS, 10% (v/v) methanol, pH 7.2) in a semidry blotter at 300 mA and 20 V for 60 min. The membrane was blocked with 1% (w/v) bovine serum albumin (BSA) in Tris-buffered saline (TBS) (20 mM Tris base, 136 mM NaCl, pH 7.6) with 0.1% (v/v) Tween® 20 (TBST) for 2 h at 25° C. followed by incubation with a rabbit polyclonal anti-serglycin antibody (ascites 1:5000) diluted in 1% (w/v) BSA in TBST for 2 h at 25° C. Membranes were subsequently rinsed with TBST, incubated with secondary HRP-conjugated antibodies (1:50,000) for 45 min at 25° C., and rinsed with TBST and TBS before being imaged using chemiluminescence reagent (Femto reagent kit, Pierce) and x-ray film.

Fluorophore-Assisted Carbohydrate Electrophoresis

The disaccharide composition of the heparin/HS attached to serglycin was compared low molecular weight heparin. DEAE enriched serglycin was digested with 100 µg/mL Pronase at 60° C. for 16 h. The sample was boiled for 5 min and 4 volumes of 96% ethanol per sample volume were added and incubate at −20° C. for 16 h. Ethanol precipitated GAGs were centrifuged at 11000 g at 4° C. for 30 min. Pellet was dried and dissolved in 100 µL of 100 mM ammonium acetate, pH 7.0. Sample was digested with 10 mU/mL HepII at 37° C. for 16 h. At the end of the digestion, 4 volumes of 96% ethanol per sample volume were added and incubate at −20° C. overnight. Sample was centrifuged at 11000×g at 4° C. for 30 min. GAGs were precipitated, and the unsaturated disaccharides were recovered in supernatant and lyopholized.

Commercial heparin was dissolved in 10 mg/mL in MilliQ water and digested with Hep II at 10 mU/mL at 37° C. overnight. At the end of the digestion, 4 volumes of 96% ethanol per sample volume were added and incubate at −20° C. overnight. Sample was centrifuged at 11000 g at 4° C. for 30 min. GAGs were precipitated, and the unsaturated disaccharides were recovered in supernatant and lyopholized.

Standard and sample disaccharides created by bacterial endoglycosidases were prepared at 250 nM in MilliQ water and labelled with 5 µL of 100 mM 2-aminoacridone hydrochloride in DMSO with 15% (v/v) glacial acetic acid followed by 5 µL of 1 M sodium cyanoborohydride in DMSO. The solution was mixed gently and incubated for 16 h at 37° C. before the addition of 500 µL of 50% (v/v) filter-sterilized (0.22 µm) glycerol. Equal volumes of samples were combined with the glycerol solution containing 0.001% (w/v) bromphenol blue immediately prior to loading the gel for electrophoresis. Samples were electrophoresed on acrylamide gels consisting of a resolving gel (23.1% (w/v) acrylamide, 1.9% (w/v) bisacrylamide, 187.5 mM Tris borate, pH 8.8, 187.5 mM Tris, pH 8.8, 2.5% (w/w) glycerol, 0.05% (w/v) APS,0.05% (v/v) TEMED) and a stacking gel (4.25% (w/v) acrylamide, 0.75% (w/v) bisacrylamide, 0.36 M Tris, pH 6.3-6.8, 4.4% (w/v) PEG8000, 0.1% (w/v) APS,0.1% (v/v) TEMED). The running buffer was 89 mM Tris, 89 mM Boric acid and 2 mM EDTA pH 8.8. All equipment and buffers were maintained at 4° C. throughout the experiment. Pre-electrophoresis was performed at 300 V per gel for 30 min. Samples and standards were loaded and electrophoresed for 3 h at 350 V per gel until the dye front was approximately 10-15 mm from the bottom of the gel. Gels were imaged by UV light using a Gel Doc™ EZ System (Biorad, Australia). Analysis of the bands was performed by comparing pixel intensity with those of the standard heparin/HS disaccharides that were run on each gel.

Activated Partial Thromboplastin Time (aPTT) Assay

The activated partial thromboplastin time (aPTT) assay was performed using human plasma collected from human donors under ethics approval from the University of New South Wales. The aPTT reagents including phospholin ES and $CaCl_2$ were purchased as a kit from $r^2$ Diagnostics Inc. (South Bend, Ind., USA). Heparin (H3393, Sigma Aldrich, St. Louis, Mo., USA) and recombinant serglycin were diluted in plasma to final concentrations of GAGs of 1-20 μg/mL. Plasma in the presence or absence of heparin or serglycin (100 μL) was incubated at 37° C. for 5 min prior to the addition of 100 μL of phospholin ES in 0.1 mM ellagic acid and incubated at 37° C. for a further 2 min. A volume of 100 μL of $CaCl_2$ was then added to each sample and the time taken for a fibrin clot to form was recorded.

Statistical Analysis

A one-way analysis of variance (ANOVA) was performed. Results of p<0.05 were considered significant. Experiments were performed in triplicate and experiments were repeated.

EXAMPLES

Example 1—Characterization of Recombinantly Expressed Serglycin

In order to produce heparin, human serglycin was recombinantly expressed in mammalian cells, and the effect of medium glucose concentration on GAG structure and also anticoagulant function determined.

Figure 2:
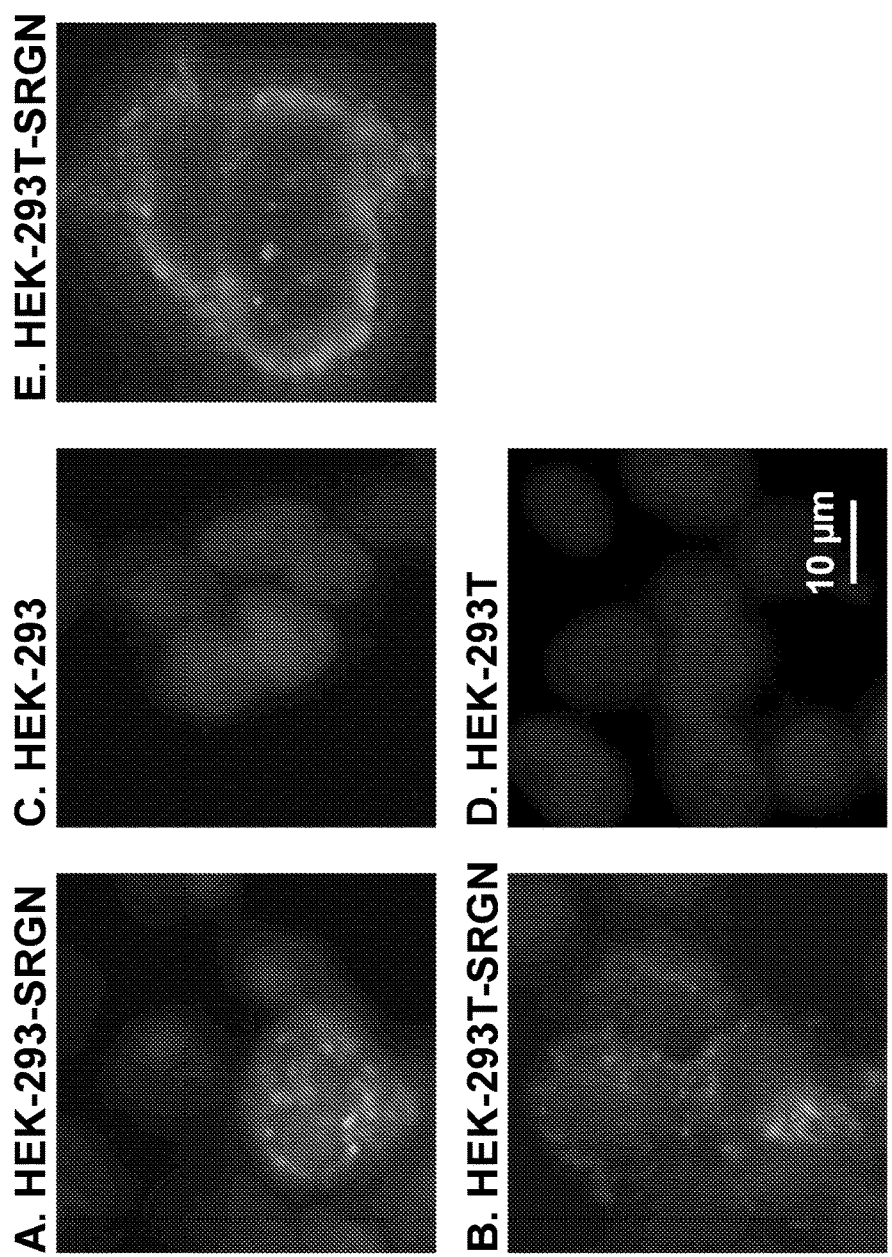
FIG. 2 shows immunolocalisation of serglycin (light area-green) in (A) HEK-293-SRGN, (B) HEK-293T-SRGN, (C) HEK-293 and (D) HEK-293T cells. Immunolocalisation of mCherry (light area-purple) is shown in (E) HEK-293T-SRGN cells. Cell nuclei are stained with DAPI (blue). Scale bar represents 10 µm.
Figure 3:
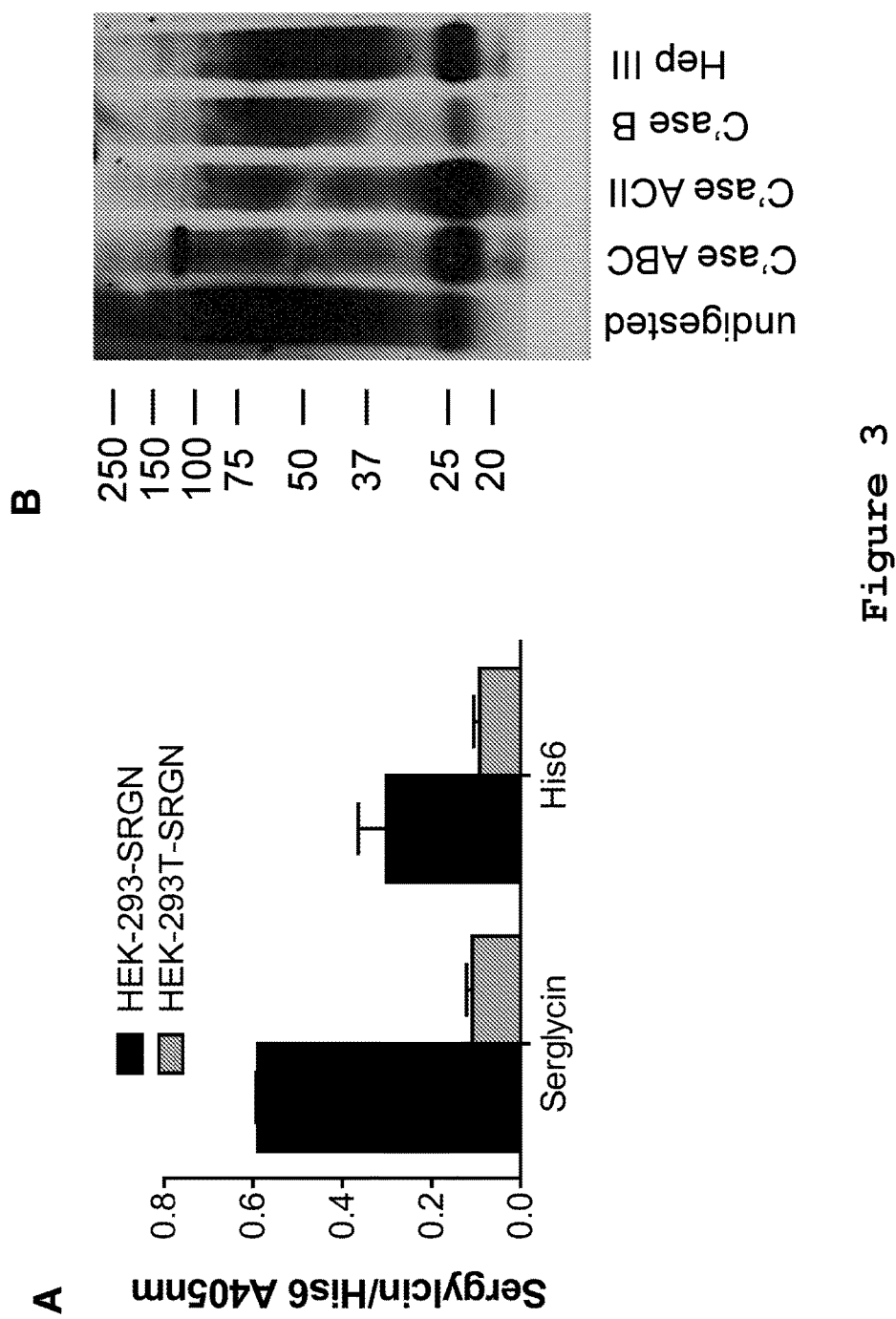
FIG. 3A is a graph showing the results of an ELISA test of recombinant serglycin for the presence of serglycin and His6 in proteoglycan-enriched medium conditioned by HEK-293-SRGN and HEK-293T-SRGN cells.
FIG. 3B is a photograph of a Western blot of serglycin-enriched medium conditioned by HEK-293-SRGN cells probed for the presence of serglycin using a rabbit polyclonal antibody. Samples were analyzed either without (−) or with (+) chondroitinase (C'ase) ABC, ACII or B digestion or heparinase III (Hep III) digestion.

After the two serglycin expression vectors were successfully constructed (see FIGS. 1B and 1C), cell transfection was performed with two different cell lines; HEK-293 and HEK-293T. Expression of serglycin by both transfected cell lines was confirmed by immunocytochemistry. Serglycin was detected intracellularly in both HEK-293-SRGN (FIG. 2A) and HEK-293T-SRGN (FIG. 2B), while serglycin was not detected in either HEK-293 or HEK-293T cells that had not been transfected (FIGS. 2C and D). Expression of the mCherry tag encoded by the CEFLP vector in the HEK-293T-SRGN cells was confirmed (FIG. 2E). The mCherry tag was predominately localized near the cell membrane, suggesting that it was being secreted into the surrounding medium. The yield from the HEK-293-SRGN and HEK-293T-SRGN cells after enrichment for the recombinantly expressed serglycin by a nickel-chelating column was approximately 1.8 mg/L and 0.5 mg/L, respectively. These serglycin-enriched fractions from each cell line were confirmed to contain serglycin and His6 by ELISA (FIG. 3A). HEK-293-SGRN was selected for further investigation.

Serglycin expressed in HEK-293-SRGN cells was characterized with respect to $M_r$ and GAG composition. Serglycin-enriched medium from these cells was analyzed by Western blotting after endoglycosidase digestion and probed with a polyclonal serglycin antibody (FIG. 3B). Recombinant serglycin was found to contain immunoreactive bands which gave a smear between 30,000 Da and more than 250,000 Da, which corresponded to the expected size of serglycin decorated with GAGs as well as a band at 25,000 Da (FIG. 3B, lane 1) representing the protein core. Densitometry of the immunoreactive bands in lane 1 indicated that approximately 15% of the serglycin was secreted as a protein core alone with the remainder (85%) being produced as a proteoglycan. The type of GAGs that decorated recombinant serglycin was analyzed by treating the sample with C'ase ABC, C'ase ACII, C'ase B or Hep III. The $M_r$ of the smear between 30,000 and >250,000 reduced to a smear between 30,000 and 100,000 as well as band at 25,000 after digestion with either C'ase ABC, ACII, B or Hep III indicating that serglycin contained CS, DS and HS/heparin (FIG. 3B, lanes 2-5).

Figure 4:
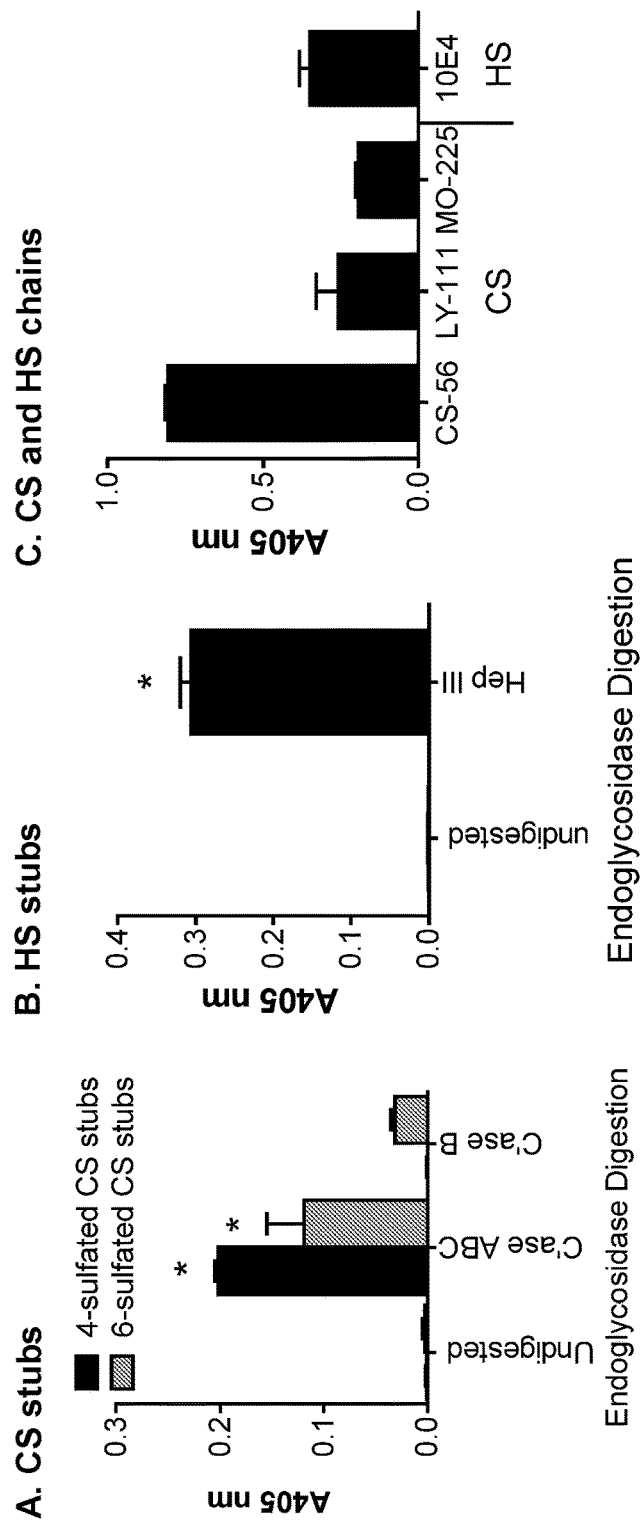
FIG. 4A is a graph showing the results of ELISA for the presence of 4- and 6-sulfated CS stubs in the serglycin-enriched medium conditioned by HEK-293-SRGN cells or in the serglycin-enriched medium following digestion with either C'ase ABC or B. Data are presented as mean±S.D. (error bars) (n=3). * indicated significant differences ($p<0.05$)
FIG. 4B is a graph showing the results of ELISA for the presence of HS stubs in the serglycin-enriched medium conditioned by HEK-293-SRGN cells following digestion with either Hep III or undigested. Data are presented as mean±S.D. (error bars) (n=3). * indicated significant differences ($p<0.05$)
FIG. 4C is a graph showing the results of ELISA for the presence of CS chain structures types A and C (clone CS-56), CS types A and D (clone LY-111), CS type D (clone MO-225) or HS chain structures (clone 10E4). Data are presented as mean±S.D. (error bars) (n=3).

The recombinant serglycin was also analyzed for the presence of sulfated CS linkage regions (un-, 4-, and 6-sulfated) after digestion with C'ase ABC or B. Samples were found to contain the 4- and 6-sulfated CS linkage regions after C'ase ABC digestion, but not C'ase B digestion indicating that serglycin was decorated with 4- and 6-sulfated CS stubs (FIG. 4A). Un-sulfated CS stubs could not be detected after C'ase ABC or B digestion (data not shown). The recombinant serglycin was also found to contain the HS/heparin stub following digestion with Hep III (FIG. 4B). Analysis of the CS chain structures by ELISA indicated that the recombinant serglycin contained CS types A, C and D as detected by the anti-CS chain antibodies CS-56, LY-111 and MO-225, respectively. HS was detected by antibody clone 10E4 (FIG. 4C).

Figure 5:
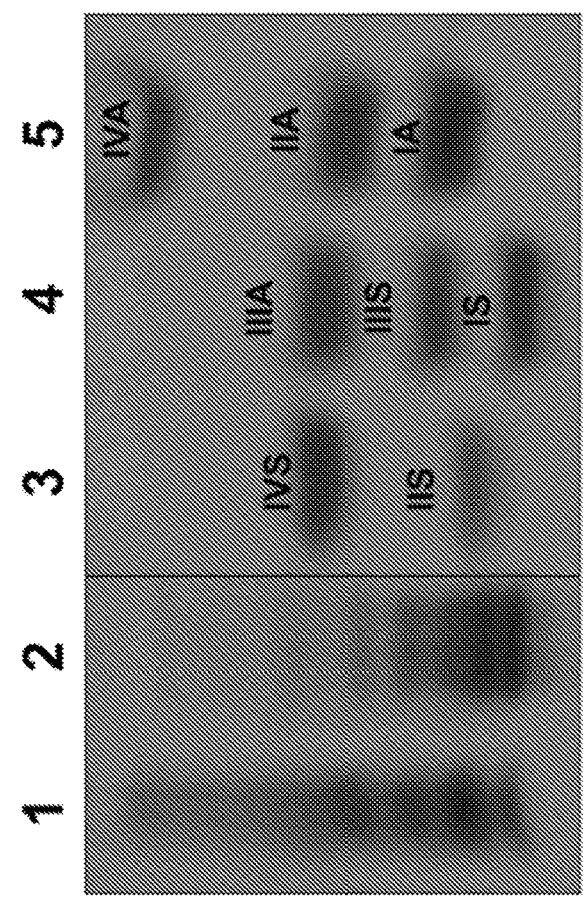
FIG. 5 is the results of fluorophore-assisted carbohydrate electrophoresis of HS/heparin disaccharides present in 1. recombinant serglycin produced by the method described herein, and 2. low molecular weight porcine heparin. The Table on the right hand side gives the name and structure of HS/heparin disaccharide standards used in the analysis.

The disaccharide composition of heparin that decorated recombinant serglycin produced by cells exposed to 25 mM glucose in the culture medium was investigated and compared to that of low molecular weight porcine heparin by fluorophore-assisted carbohydrate electrophoresis. Heparin disaccharide standards were electrophoresed on the same gel and used to determine composition. Heparin disaccharide structures are indicated in FIG. 5 by both their abbreviated name and structure. The disaccharides identified and indicated in FIG. 5 are as follows: IA (Δ-UA,2S-GlcNAc,6S): a disaccharide of 2-O-sulfated 4,5 unsaturated uronic acid and 6-O-sulfated N-acetylglucosamine; IS (Δ-UA,2S-GlcNS, 6S): a disaccharide of 2-O-sulfated 4,5 unsaturated uronic acid and 6-O-sulfated, N-sulfated glucosamine; IIA(Δ-UA-GlcNAc,6s): a disaccharide of 4,5 unsaturated uronic acid and 6-O-sulfated N-acetylglucosamine; IIS (Δ-UA-GlcNS, 6S): a disaccharide of 4,5 unsaturated uronic acid and 6-O-sulfated, N-sulfated glucosamine; IIIA (Δ-UA,2S-GlcNAc): a disaccharide of 2-O-sulfated 4,5 unsaturated uronic acid and N-acetylglucosamine; IIIS (Δ-UA,2S-GlcNS): a disaccharide of 2-O-sulfated 4,5 unsaturated uronic acid and N-sulfated glucosamine; IVA (Δ-UA-GlcNAc): a disaccharide of 4,5 unsaturated uronic acid and N-acetylglucosamine; IVS (Δ-UA-GlcNS): a disaccharide of 4,5 unsaturated uronic acid and N-sulfated glucosamine.

The heparin that decorated the recombinantly expressed serglycin contained 15% tri-sulfated disaccharides as well as 40% di-sulfated, 25% monosulfated and 20% unsulfated disaccharides (FIG. 5). Low molecular weight porcine heparin contained a higher proportion of sulfated disaccharides than the recombinantly expressed heparin being 40% trisulfated, 45% disulfated, 10% monsulfated and 5% unsulfated disaacharides (FIG. 5).

Figure 6:
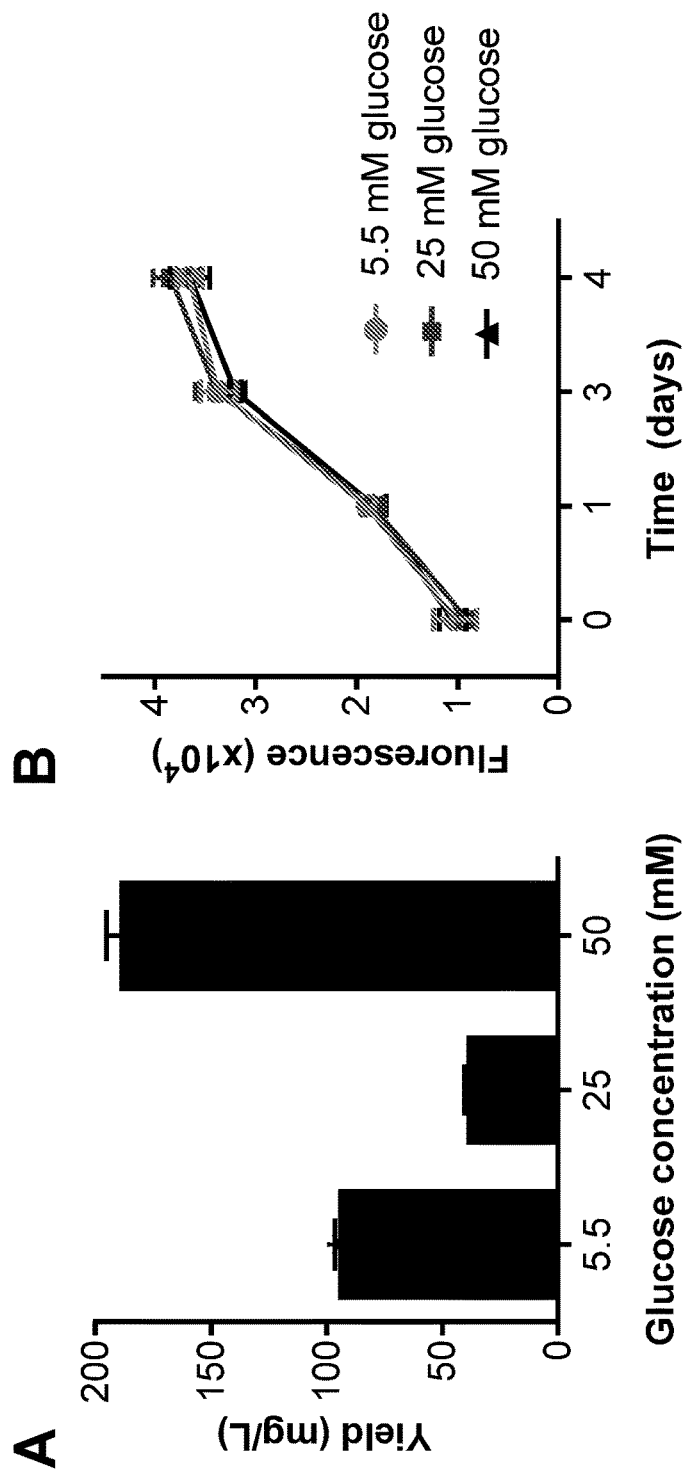
FIG. 6A is a graph showing the yield of proteoglycans from HEK-293-SRGN cells cultured in different glucose concentrations (5.5, 25 and 50 mM).
FIG. 6B is a graph showing the relative number of HEK-293 cells measured over a period of 4 days exposed to medium containing 5.5, 25 or 50 mM glucose measured by the Cyquant assay. Data presented at mean±standard deviation (n=3) for the fluorescence measured for each condition which is directly proportional to the number of cells in each condition.

Example 2—Effect of Culture Conditions on the Yield and Structure of the Recombinantly Expressed Serglycin The yield from the HEK-293-SRGN cells grown in normal medium having a glucose concentration of 25 mM after enrichment for the recombinantly expressed serglycin by an anion exchange column was found to be 39 mg/L, which was significantly higher than after enrichment in the nickel-chelating column (FIG. 6A). Interestingly, when the medium contained either 5.5 or 50 mM glucose, the yield of proteoglycans was higher than when 25 mM glucose was used (FIG. 6A). The possibility that this was due to increased proliferation of the cells grown in higher concentrations of glucose was explored by measuring cell proliferation over a period of 14 days. The glucose concentration in the medium was found not to affect cell proliferation over this time period (FIG. 6B).

Figure 7:
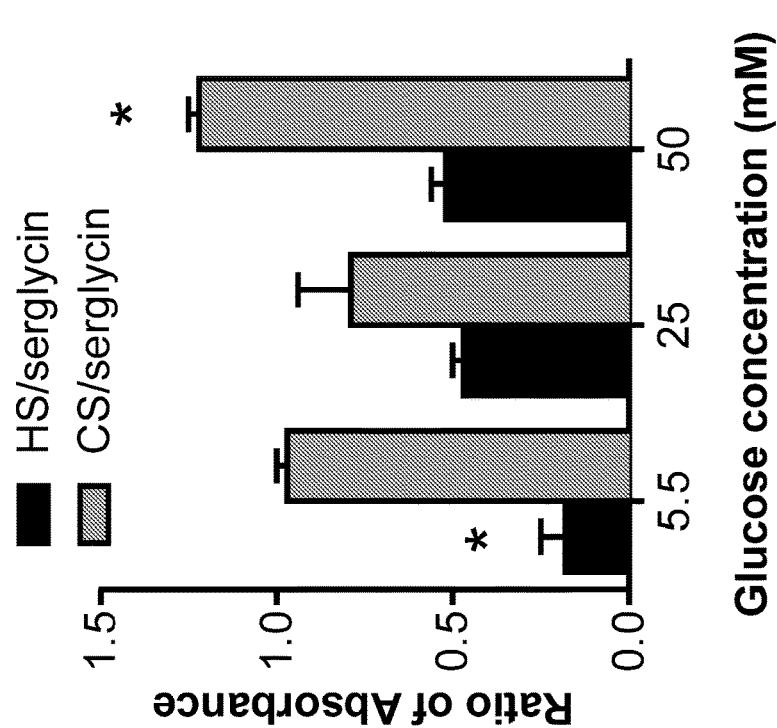
FIG. 7 illustrates the effect of medium glucose concentration on serglycin expression utilizing an ELISA assay.

The effect of glucose concentration in the culture medium on serglycin, CS and HS expression was analysed by ELISA after enrichment of the conditioned medium for serglycin by anion exchange chromatography. When the ratio of serglycin to either CS or HS was analyzed, the data indicated that cells exposed to 5.5 mM glucose in the medium produced serglycin with significantly ($p<0.05$) less HS than cells exposed to 25 mM glucose in the medium, however there was no difference in the amount of CS (FIG. 7). Cells exposed to 50 mM glucose in the medium produced serglycin with no difference in the amount of HS compared to cells exposed to 25 mM glucose in the medium, however there was significantly ($p<0.05$) more CS (FIG. 7).

Example 3—Anticoagulant Activity of Recombinantly Expressed Serglycin

Figure 8:
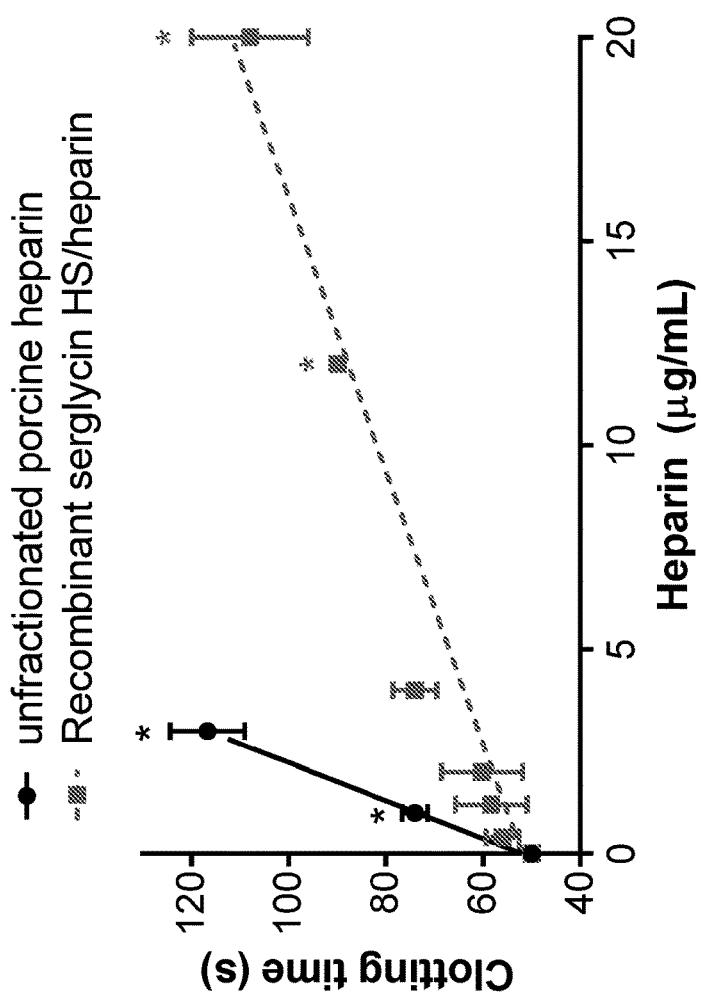
FIG. 8 is a graph showing anticoagulant activity of recombinant serglycin compared to heparin measured by the aPTT assay. Data is presented as mean±standard deviation (n=3). The line of best fit was determined by linear regression. * indicated significant differences ($p<0.05$) compared to plasma in the absence of GAGs analyzed by one-way ANOVA.

The aPTT assay is used clinically to monitor heparin doses in patients and was used in this study to determine the anticoagulant activity of the recombinantly expressed serglycin. The anticoagulant activity of the recombinantly expressed serglycin produced by cells with the highest level of HS as produced in cells exposed to 25 mM glucose in the culture medium was investigated and compared to the activity of porcine heparin. The addition of porcine heparin over the range of 1.2-3.5 µg/mL, which is equivalent to 0.2-0.7 USP, was found to significantly ($p<0.05$) delay fibrin clot formation compared to the absence of heparin (FIG. 8). Heparin/HS decorating the recombinant serglycin was also found to significantly ($p<0.05$) delay fibrin clot formation in the therapeutic range with the glycosaminoglycan concentration range of 8.4-25.1 µg/mL, which was estimated based on the length of heparin/HS attached to serglycin determined by Western blotting. A linear regression of heparin concentration versus clotting time indicated that the unfractionated porcine heparin was approximately 7 times more potent in its anticoagulant activity than the heparin/HS from recombinant serglycin on a weight basis.

The invention claimed is:

1. A method of producing a proteoglycan having anticoagulant activity, comprising:
   a. providing a cell comprising a recombinant nucleic acid encoding a core protein having one or more glycosaminoglycan attachment sites, wherein the core protein comprises SEQ ID NO: 1; and
   b. incubating the cell under conditions to promote the production of a proteoglycan comprising the core protein linked to heparin or heparin and heparan sulfate such that the proteoglycan comprising the core protein linked to heparin or heparin and heparan sulfate is produced.

2. The method of claim 1, wherein the core protein further comprises SEQ ID NO: 2 or a fragment thereof having one or more glycosaminoglycan attachment sites or SEQ ID NO: 3 or a fragment thereof having one or more glycosaminoglycan attachment sites.

3. The method of claim 1, wherein the core protein comprises a functional domain.

4. The method of claim 1, wherein the core protein comprises a signal sequence for secretion of the proteoglycan, an affinity tag or both a signal sequence for the secretion of the proteoglycan and an affinity tag.

5. The method of claim 1, wherein the core protein comprises a signal sequence selected from the group consisting of SEQ ID NOS: 16 to 20.

6. The method of claim 5, wherein the core protein comprises an affinity tag.

7. The method of claim 1, wherein the core protein comprises a signal sequence of SEQ ID NO: 16.

8. The method of claim 1, wherein step (b) comprises incubating the cell in medium under conditions which permit expression of the core protein, wherein the medium comprises glucose at a concentration which promotes production of a proteoglycan comprising the core protein linked to heparin or heparin and heparan sulfate.

9. The method of claim 8, wherein the glucose is at a concentration of from 5 mM to 50 mM.

10. The method of claim 9, wherein the medium further comprises sulfate at a concentration in the range of from 0.5 mM to 50 mM, phosphate at a concentration in the range of from 0.5 mM to 50 mM or sulfate at a concentration in the range of from 0.5 mM to 50 mM and phosphate at a concentration in the range of from 0.5 mM to 50 mM.

11. The method of claim 1, wherein step (b) comprises incubating the cell in medium which comprises glucose at a concentration which promotes production of proteoglycan comprising the core protein linked to heparin or heparin and heparan sulfate in an amount that is greater than the amount of other glycosaminoglycans linked to the core protein.

12. The method of claim 11, wherein the glucose is at a concentration of from 5 mM to 50 mM.

13. The method of claim 12, wherein the medium further comprises sulfate at a concentration in the range of from 0.5 mM to 50 mM, phosphate at a concentration in the range of from 0.5 mM to 50 mM, or sulfate at a concentration in the range of from 0.5 mM to 50 mM and phosphate at a concentration in the range of from 0.5 mM to 50 mM.

14. The method of claim 1, wherein the cell is human embryonic kidney (HEK-293).

15. A method of producing heparin, heparan sulfate or both heparin and heparan sulfate, comprising:
   a. providing a cell comprising a recombinant nucleic acid encoding a core protein having one or more glycosaminoglycan attachment sites, wherein the core protein comprises SEQ ID NO: 1;
   b. incubating the cell under conditions to promote production of a proteoglycan comprising the core protein linked to heparin or heparin and heparan sulfate such that the proteoglycan comprising the core protein linked to heparin or heparin and heparan sulfate is produced; and c. isolating the heparin, heparan sulfate or both heparin and heparan sulfate.

16. The method of claim 15, wherein the core protein comprises SEQ ID NO: 2 or a fragment thereof having one or more glycosaminoglycan attachment sites or SEQ ID NO: 3 or a fragment thereof having one or more glycosaminoglycan attachment sites.

17. The method of claim 15, wherein the core protein comprises a functional domain.

18. The method of claim 15, wherein the core protein comprises a signal sequence for secretion of the proteoglycan, an affinity tag or both a signal sequence for the secretion of the proteoglycan and an affinity tag.

19. The method of claim 15, wherein the core protein comprises a signal sequence selected from the group consisting of SEQ ID NOS: 16 to 20.

20. The method of claim 19, wherein the core protein comprises an affinity tag.

21. The method of claim 15, wherein the core protein comprises a signal sequence of SEQ ID NO: 16.

22. The method of claim 15, wherein step (b) comprises incubating the cell in medium under conditions which permit expression of the core protein, wherein the medium comprises glucose at a concentration which promotes production of a proteoglycan comprising the core protein linked to heparin or heparin and heparan sulfate.

23. The method of claim 22, wherein the glucose is at a concentration of from 5 mM to 50 mM.

24. The method of claim 23, wherein the medium further comprises sulfate at a concentration in the range of from 0.5 mM to 50 mM, phosphate at a concentration in the range of from 0.5 mM to 50 mM, or sulfate at a concentration in the range of from 0.5 mM to 50 mM and phosphate at a concentration in the range of from 0.5 mM to 50 mM.

25. The method of claim 15, wherein step (b) comprises incubating the cell in medium which comprises glucose at a concentration which promotes production of proteoglycan comprising the core protein linked to heparin or heparin and heparan sulfate in an amount that is greater than the amount of other glycosaminoglycans linked to the core protein.

26. The method of claim 25, wherein the glucose is at a concentration of from 5 mM to 50 mM.

27. The method of claim 26, wherein the medium further comprises sulfate at a concentration in the range of from 0.5 mM to 50 mM, phosphate at a concentration in the range of from 0.5 mM to 50 mM, or sulfate at a concentration in the range of from 0.5 mM to 50 mM and phosphate at a concentration in the range of from 0.5 mM to 50 mM.

28. The method of claim 15, wherein the cell is human embryonic kidney (HEK-293).

* * * * *